(12) United States Patent
Millar et al.

(10) Patent No.: US 8,269,082 B2
(45) Date of Patent: Sep. 18, 2012

(54) CEREALS WITH ALTERED DORMANCY

(75) Inventors: Anthony Alan Millar, O'Connor (AU); John Viggo Jacobsen, Weetangera (AU); Franz Jacques Marie Gubler, Lyneham (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 768 days.

(21) Appl. No.: 12/083,898

(22) PCT Filed: Oct. 19, 2006

(86) PCT No.: PCT/AU2006/001556
§ 371 (c)(1),
(2), (4) Date: Feb. 27, 2009

(87) PCT Pub. No.: WO2007/045040
PCT Pub. Date: Apr. 26, 2007

(65) Prior Publication Data
US 2009/0291193 A1   Nov. 26, 2009

Related U.S. Application Data

(60) Provisional application No. 60/729,460, filed on Oct. 20, 2005.

(51) Int. Cl.
*A01H 5/00* (2006.01)
*C12N 5/04* (2006.01)
(52) U.S. Cl. ..................... 800/320.3; 435/410
(58) Field of Classification Search .................. None
See application file for complete search history.

(56) References Cited

U.S. PATENT DOCUMENTS

| | | | |
|---|---|---|---|
| 5,004,863 | A | 4/1991 | Umbeck et al. |
| 5,104,310 | A | 4/1992 | Saltin |
| 5,159,135 | A | 10/1992 | Umbeck et al. |
| 5,177,010 | A | 1/1993 | Goldman et al. |
| 5,384,253 | A | 1/1995 | Krzyzek et al. |
| 5,472,869 | A | 12/1995 | Krzyzek et al. |
| 5,589,617 | A | 12/1996 | Nehra et al. |
| 5,925,517 | A | 7/1999 | Tyagi et al. |
| 6,100,447 | A | 8/2000 | Wu et al. |
| 6,541,527 | B1 | 4/2003 | Ihm et al. |
| 6,982,321 | B2 | 1/2006 | Winter et al. |
| 2003/0233670 | A1 | 12/2003 | Edgerton et al. |
| 2004/0216190 | A1* | 10/2004 | Kovalic ............... 800/289 |

FOREIGN PATENT DOCUMENTS

| | | |
|---|---|---|
| AU | 2006303820 A1 | 4/2007 |
| CA | 2626304 A1 | 4/2007 |
| EP | 1586652 A1 | 12/2005 |
| EP | 1947925 | 4/2007 |
| WO | WO 87/06614 | 11/1987 |
| WO | WO 90/11682 | 10/1990 |
| WO | WO 92/09696 | 6/1992 |
| WO | WO 93/21335 | 10/1993 |
| WO | WO 94/00977 | 1/1994 |
| WO | WO 94/19930 | 9/1994 |
| WO | WO 97/48814 | 12/1997 |
| WO | WO 99/14314 | 3/1999 |
| WO | WO 97/20936 | 6/1999 |
| WO | WO 99/32619 | 7/1999 |
| WO | WO 99/49029 | 9/1999 |
| WO | WO 99/53050 | 10/1999 |
| WO | WO 01/34815 | 5/2001 |
| WO | WO 02/46377 A2 | 6/2002 |
| WO | WO 2004/113527 | 12/2004 |
| WO | WO 2006/138012 A1 | 12/2006 |
| WO | WO 2007/045040 A1 | 4/2007 |

OTHER PUBLICATIONS

Kushiro et al, The EMBO Journal, 2004, col. 23, pp. 1647-1656, cited in the IDS filed Jul. 24, 2008.*
Francki and Appels, Genome Biology, Apr. 2002, vol. 3, No. 5, reviews, pp. 1013.1-1013.5.*
BLAST results from SEQ ID No. 10.*
Berrie, Alex, Possible Role of Volatile Fatty Acids and Abscisic Acid in the Dormancy of Oats. Plant Physiol. 1979, 63:758-764.
Colot et al., Localization of Sequences in Wheat Endosperm Protein Genes which Confer Tissue-Specific Expression in Tobacco. The EMBO Journal. 1987, 6(12):3559-356.
Gubler et al., Dormancy release, ABA and pre-harvest sprouting. Current Opinion in Plant Biology. 2005, 8:183-187.
Himi et al., Effect of grain colour gene (R) on grain dormancy and sensitivity of the embryo to abscisic acid (ABA) in wheat. Journal of Experimental Botany. 2002, 53(374):1569-1574.
Karssen et al., Induction of dormancy during seed development by endogenous abscisic acid: studies on abscisic acid deficient genotypes of *Arabidopsis thaliana* (L.) Heynh. Planta 1983, 157:158-165.
King, R.W., Preharvest Field Sprouting in Cereals. Editor: Derera, N.F., CRC Press Inc. 1989, Chapter 3: pp. 27-61.
Koorneef, et al., Dormancy in Plants From Whole Plant Behaviour to Cellular Control. Editors: Viemont, J.-D., and Crabbe, J., CABI Publishing. 2000, Chapter 3, pp. 364-373. Kulwal et al., Genetic basis of pre-harvest sprouting tolerance using single-locus and two-locus QTL analyses in bread wheat. Funct Integr Genomics. 2004, 4:94-101.
Li et al., Genes controlling seed dormancy and pre-harvest sprouting in a rice-wheat-barley comparison. Funct Integr Genomics. 2004, 4:84-93.
Mares et al., A QTL located on chromosome 4A associated with dormancy in white- and red-grained wheats of diverse origin. Theor Appl Genet. 2005, pp. 1-8.
McCarty, D.R., Genetic Control and Integration of Maturation and Germination Pathways in Seed Development. Annu Rev Plant Physiol Plant Mol Biol. 1995, 46:71-93.
Morris et al., Seed Dormancy and Responses of Caryopses, Embryos, and Calli to Abscisic Acid in Wheat. Plant Physiol. 1989, 90:643-647.
Qin and Zeevaart, Overexpression of a 9-cis-Epoxycarotenoid Dioxygenase Gene in *Nicotiana plumbaginifolia* Increases Abscisic Acid and Phaseic Acid Levels and Enhances Drought Tolerance. Plant Physiology. 2002, 128:544-551.

(Continued)

*Primary Examiner* — Eileen B O Hara
(74) *Attorney, Agent, or Firm* — John P. White; Cooper & Dunham LLP

(57) ABSTRACT

The present invention relates to polypeptides, and polynucleotides encoding therefor, which influence seed dormancy in cereals such as wheat and barley. In particular, the present invention relates to polypeptides with ABA 8'-hydroxylase activity, and polynucleotides encoding these proteins. Also provided are cereal plants which produce seeds that have altered rates of germination, and/or levels of dormancy, when compared to seeds from wild-type plants, as well as methods of producing such plants.

15 Claims, 22 Drawing Sheets

OTHER PUBLICATIONS

Figure 1:
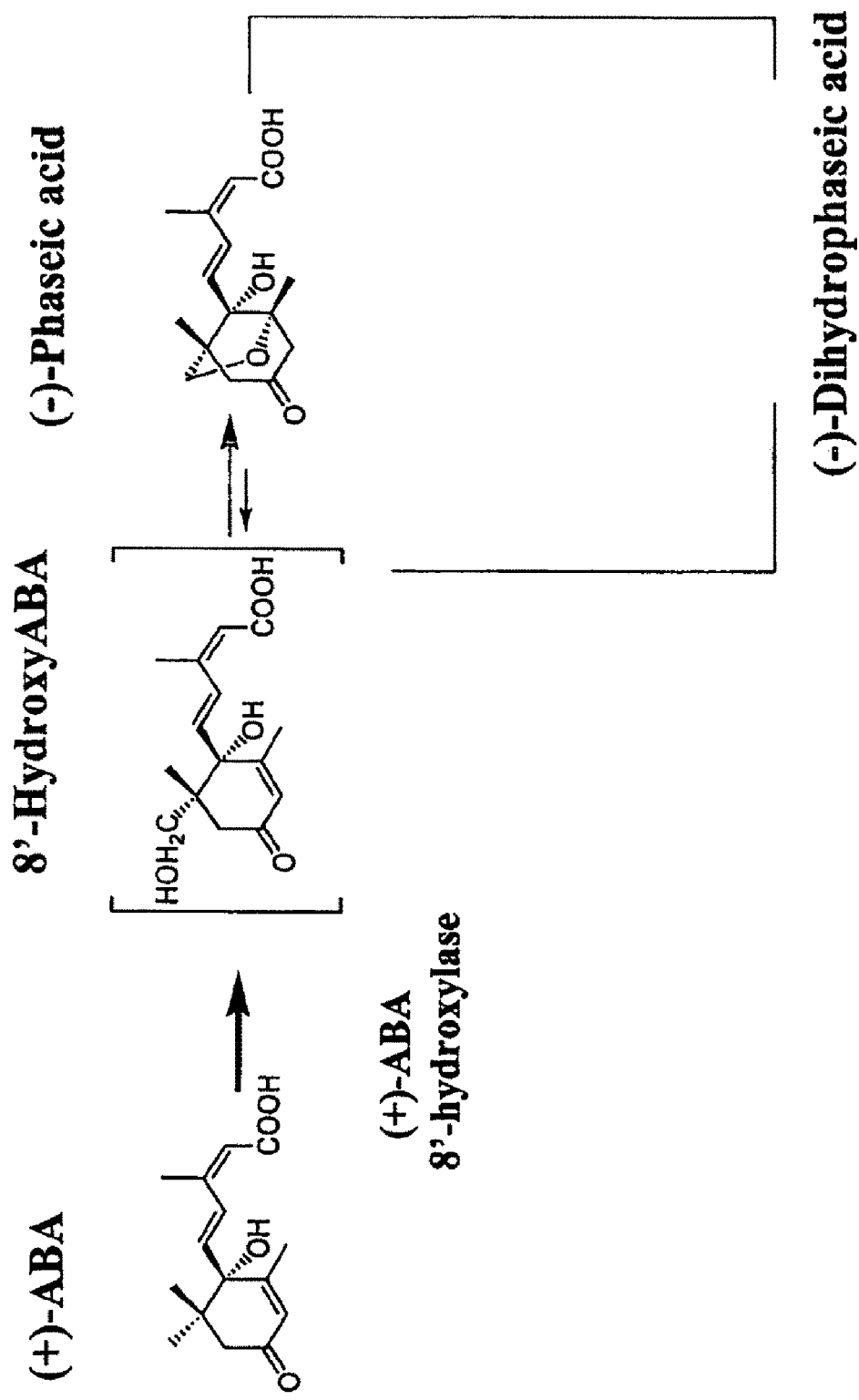

Senior, I.J., Biotechnology & Genetic Engineering Reviews. Editor: Tombs, M.P., Intercept ltd. 1998, vol. 15, pp. 78-119.

Thompson et al., Ectopic expression of a tomato 9-*cis*-epoxycarotenoid dioxygenase gene causes over-production of abscisic acid. The plant Journal. 2000, 23(3):363-374.

Walker-Simmons, M., ABA Levels and Sensitivity in Developing Wheat Embryos of Sprouting Resistant and Susceptible Cultivars. Plant Physiol. 1987, 84:61-66.

Supplemental European Search Report, issued Aug. 3, 2009 in connection with European Patent Application No. 2006804419.

Communication from the Examining Division, issued Nov. 19, 2009 in connection with European Patent Application No. 2006804419.

Request for Further Processing, filed Sep. 13, 2010 in connection with European Patent Application No. 2006804419.

Communication from the Examining Division, issued Nov. 17, 2010 in connection with European Patent Application No. 2006804419.

Response to communication from the Examining Division, filed May 27, 2011 in connection with European patent Application No. 2006804419.

US 5,962,233, 10/1999, Livak et al. (withdrawn).

Supplementary European Search Report, issued Aug. 3, 2009 in connection with European Patent Application No. 06804419.7.

Preliminary Report on Patentability, issued Aug. 3, 2009 in connection with European Patent Application No. 06804419.7.

Communication from the Examining Division, issued Nov. 17, 2010 in connection with European Patent Application No. 06804419.7.

Response to Communication from the Examining Division, filed May 27, 2011 in connection with European Patent Application No. 06804419.7.

Response to Communication from the Examining Division, filed Sep. 13, 2010 in connection with European Patent Application No. 06804419.7.

Ackerson, R.C., Abscisic Acid and Precocious Germination in Soybeans. Journal of Experimental Botany, 1984, 35(3):414-421.

Ali-Rachedi et al., Changes in endogenous abscisic acid levels furing dormancy release and maintenance of mature seeds: studies with the Cape Verde Islands ecotype, the dormant model of *Arabidopsis thaliana*. Planta, 2004, 219:479-488.

Beaudoin et al., Interactions between Abscisic Acid and Ethylene Signaling Cascades. The Plant Cell, 2000, 12:1103-1115.

Bewley, J.D., Seed Germination and Dormancy. The Plant Cell, 1997, 9:1055-1066.

Black, M., The Role of Endogenous Hormones in Germination and Dormancy. Israel Journal of Botany, 1980/1, 29:181-192.

Chiwocha et al., The *etr1-2* mutation in *Arabidopsis thaliana* affects the abscisic acid, auxin, cytokinin and gibberellin metabolic pathways during maintenance of seed dormancy, moist-chilling and germination. The Plant Journal, 2005, 42:35-48.

Cutler and Krochko, Formation and breakdown of ABA. Trends in Plant Science, 1999, 4(12):472-478.

Iuchi et al., Regulation of drought tolerance by gene manipulation of 9-*cis*-epoxycarotenoid dioxygenase, a key enzyme in abscisic acid biosynthesis in *Arabidopsis*. The Plant Journal, 2001, 27(4)325-333.

Jacobsen et al., Abscisic acid, phaseic acid anggibberelin contents associated with dormancy and germination in barley. Physiologia Plantarum, 2002, 115:428-441.

Jager et al., The brassinosteroid growth response in pea is not mediated by changes in gibberellin content. Planta, 2005, 221:141-148.

Kato et al., Detection of loci controlling seed dormancy on group 4 chromosomes of wheat and comparative mapping with rice and barley genomes. Theor Appl Genet, 2001, 102:980-985.

Koornneef et al., Seed dormancy and germination. Current Opinion in Plant Biology, 2002, 5:33-36.

Koornneef and Jorna, The Isolation of Abscisic Acid (ABA) Deficient Mutants by Selection of Induced Revertants in Non-germinating Gibberellin Sensitive Lines of *Arabidopsis thaliana* (L.) Heynh. Theor Appl Genet, 1982, 61:385-393.

Krochko et al., (+)-Abscisic Acid 8'-Hydroxylase Is a Cytochrome P450 Monooxygenase. Plant Physiol, 1998, 118:849-860.

Kushiro et al., The *Arabidopsis* cytochrome P450 CYP707A encodes ABA 8'-hydroxylases: key enxymes in ABA catabolism. The EMBO Journal, 2004, 23:1647-1656.

Mares and Campbell, Mapping components of flour and noodle colour in Australian wheat. Aust J Agric Res, 2001, 52: 1297-1309.

Matthews et al., Maize phytoene desaturase and ζ-carotene desaturase catalyse a poly-Z desaturation pathway: implications for genetic engineering of carotenoid content among cereal crops. Journal of Experimental Botany, 2003, 54(391):2215-2230.

McKibbin et al., Transcripts of *Vp-1* homeologues are misspliced in modern wheat and ancestral species. PNAS, 2002, 99(15):10203-10208.

Millar et al., Seed dormancy and ABA metabolism in *Arabidopsis* and barley: the role of ABA 8'-hydroxylase. The Plant Journal, 2006, 45:942-954.

Mori et al., Mapping QTLs for grain dormancy on wheat chromosome 3A and the group 4 chromosomes, and their combined effect. Theor Appl Genet, 2005, 110:1315-1323.

Prada et al., Genetic control of dormancy in a Triumph/Morex cross in barley. Theor Appl Genet, 2004, 109:62-70.

Qin and Zeevaart, The 9-*cis*-epoxycarotenoid cleavage reaction is the key regulatory step of abscisic acid biosynthesis in water-stressed bean. PNAS, 1999, 96(26):15354-15361.

Saito et al., *Arabidopsis* CYP707As Encode (+)-Abscisic Acid 8'Hydroxylase, a Key Enzyme in the Oxidative Catabolism of Abscisic Acid. Plant Physiology, 2004, 134:1439-1449.

Schwartz et al., Specific Oxidative Cleavage of Carotenoids by VP14 of Maize. Science, 1997, 276:1872-1874.

Seo and Koshiba, Complex regulation of ABA biosynthesis in plants. Trends in Plant Science, 2002, 7(1):41-48.

Sharp et al., Validation of molecular markers for wheat breeding. Aust J Agric Res, 2001, 52:1357-1366.

Symons et al., The *bushy* pea mutant is IAA-deficient. Physiologia Plantarum, 2002, 116:389-397.

Walton, D.C., Does ABA Play a Role in Seed Germination? Israel Journal of Botany, 1980/81, 29:168-180.

Wang et al., Modulation of germination of embryos isolated from dormant and nondormant barley grains by manipulation of endogenous abscisic acid. Planta, 1995, 195:586-592.

Zhou et al., A New Abscisic Acid Catabolic Pathway. Plant Physiology, 2004, 134:361-369.

International Preliminary Report on Patentability issued by the International Bureau of WIPO dated Apr. 22, 2008 in connection with PCT International Application No. PCT/AU2006/001556.

Written Opinion issued by the International Searching Authority (ISA/AU) on Jan. 24, 2007 in connection with PCT International Application No. PCT/AU2006/001556.

International Search Report issued by the International Searching Authority (ISA/AU) on Jan. 24, 2007 in connection with International Application No. PCT/AU2006/001556.

WO 2004/113527 A1 (Riken) Dec. 29, 2004.

Saito, S. et al., *Arabidopsis* CYP707As Encode (+)-Abscisic Acid 8'-; Hydroxylase, a Key Enzyme in the Oxidative Catabolism of Abscisic Acid, *Plant Physiology*, 2004, 134: 1439-1449.

Kushiro, T. et al., The *Arabidopsis* cyctochrome P450 CYP707A encodes ABA 8'-hydroxylases: key enzymes in ABA catabolism, The EMBO Journal, 2004, 23: 1647-1656.

Genpept Accession #Q6YVJ4 (Putative cytochrome 450) Jul. 5, 2004.

Supplementary European Search Report and Opinion, issued Aug. 3, 2009, in connection with European Patent Application No. 06804419.7.

Chono M., et al. Field studies on the regulation of abscisic acid content and germinability during grain development of barley: molecular and chemical analysis of pre-harvest sprouting. J Exp Bot. 2006;57(10):2421-34. Epub Jun. 23, 2006.

Krochko JE, et al. (+)-Abscisic acid 8'-hydroxylase is a cytochrome P450 monooxygenase. Plant Physiol. Nov. 1988;118(3):849-60.

Millar AA,. et al. Seed dormancy and ABA metabolism in *Arabidopsis* and barley: the role of ABA 8'-hydroxylase. Plant J. Mar. 2006;45(6):942-54.

Nambara E and Marion-Poll A. Abscisic Acid Biosynthesis and Catabolism. Annu. Rev. Plant Biol. 2005; 56:165-185.

Yang SH and Choi D. Characterization of genes encoding ABA 8'-hydroxylase in ethylene-induced stem growth of deepwater rice (*Oryza sativa* L.). Biochem Biophys Res Commun. Nov. 24, 2006;350(3):685-90. Epub Sep. 27, 2006.

Preliminary Opinion of the Examiner on Patentability issued on Aug. 3, 2009 by the European Patent Office in connection with European Patent Application No. EP 06804419.7.

Supplementary European Search Report issued on Aug. 3, 2009 by the European Patent Office in connection with European Patent Application No. EP 06804419.7.

Communication from the Examining Division issued on Nov. 19, 2009 by the European Patent Office in connection with European Patent Application No. EP 06804419.7.

Sep. 13, 2010 Response to Examination Report and Request for Further Processing filed with the European Patent Office in connection with European Patent Application No. EP 06804419.7.

Communication from the Examining Division issued on Nov. 17, 2010 by the European Patent Office in connection with European Patent Application No. EP 06804419.7.

May 27, 2011 Response to Examination Report and Request for Further Processing filed with the European Patent Office in connection with European Patent Application No. EP 0684419.7.

Communication from the Examining Division issued on Oct. 10, 2011 by the European Patent Office in connection with European Patent Application No. EP 06804419.7.

First Examination Report issued on Aug. 30, 2011 by the Australian Patent Office in connection with Australian Patent Application No. 2006303820.

Ackerson R.C., Abscisic Acid and Precocious Germination in Soybeans. Journal of Experimental Botany. (1984) 35(3):414-421.

Berrie A., Possible Role of Volatile Fatty Acids and Abscisic Acid in the Dormancy of Oats. Plant Physiol. (1979) 63:758-764.

Black M., The Role of Endogenous Hormones in Germination and Dormancy. Israel Journal of Botany. (1980/1981) 29:181-192.

Feurtado et al., A merging of paths: abscisic acid and hormonal cross-talk in the control of seed dormancy maintenance and alleviation. Seed Development, Dormancy and Germination. Eds. Bradford, K.J., and Nonogaki, H., Blackwell Publishing (2007) Chapter 8, 176-222.

Grubler et al., Dormancy release, ABA and pre-harvest sprouting. Current Opinion in Plant Biology (2005) 8:183-187.

Karssen et al., Induction of dormancy during seed development by endogenous abscisic acid: studies on abscisic acid deficient genotypes of *Arabidopsis thaliana* (L.) Heynh. Planta (1983) 157:158-165.

King, R.W., Physiology of Sprouting Resistance. Preharvest Field Sprouting in Cereals. Ed. Derera, N.F., CRC Press, Inc. (1989) Chapter 3, pp. 28-61.

Qin and Zeevaart, Overexpression of a 9-cis-Epoxycarotenoid Dioxygenase Gene in *Nocotiana plumbaginifolia* Increases Abscisic Acid and Phaseic Acid Levels and Enhances Drought Tolerance. Plant Physiology (2002) 128:544-551.

Thompson et al., Ectopic expression of a tomato 9-cis-epoxycarotenoid dioxygenase gene causes over-production of abscisic acid. The Plant Journal (2000) 23(3):363-374.

Walton, D.C. Does ABA Plat A Role in Seed Germination? Israel Journal of Botany (1980/1981) 29:168-180.

Yamaguchi et al., Regulation of ABA and GA levels during seed development and germination in *Arabidopsis*. Seed Development, Dormancy and Germination. Eds. Bradford, K.J., and Nonogaki, H., Blackwell Publishing (2007) Chapter 9, pp. 224-247.

\* cited by examiner

```
   1  CCGGTTGATT TTAATATTTT TCGAAAATTT AAGACACGGA GGTGCATGCT
  51  CGCGACAATT TCCTTGACGA CGGACCAAAA GGTCAGTTCA ACACCTGTCA
 101  TTCCGCATGC ATTCCTACTG AACGGCTGCT TTAAACCGTT CAGTGTTTCA
 151  CCCCCAAGAA TCACGTAGAG AATGACTCAC ATTAGTCTTA GACGGAACGA
 201  AGAATGAGAG GACATAAATA ACCGGCCCAA TCAGTAGACA TGCGGGCCAA
 251  TGAAAATATC TGGAGGCCAA CTGAGCTAGT GCTACGTGAC GATGCCGTGG
 301  CCAGGCCAGG AGGACGGGGC TGGGATATTA TAGGAGAGGG AAGAGTATAT
 351  ATCTGAGTAA TCAATCGAGC ATGCGGCCAA ATGCTACAGC AGAATTACAG
 401  GAGAGGGAAG CATCAGTCGT CTCGTACGAG AGCGTGTGCA GCGCTGAGAG
 451  GAGACGGGAC GTGGGCCGAA AGAGAGATGG ATGGGTGAGC TGTTGGTGTT
 501  GCGACCTCCC GCGCTGGAAA GCTGGACTGG ACTGGACTGG ACTGCGTGGA
 551  TTGGGCAATT GATTAGTGGC TCGGTCCAGC TCTTGCCCGA TTAAACTGCG
 601  CAATAATTCG CTGAGCCTCA CAGCTCCTAG TTTAGTTTAG ATCTTTAGGC
 651  AGGGGCCGGG AGACCGGCAA CGAGGAGAGA GCGGGAGCGG CGCATCACCG
 701  CCAATCTATA AATACCTGCC ACGCCGCTCG CATTTCCCTC CACACCCAGG
 751  CACCACCAAC CCACCACCCA TCTCCCCTCC TCTCCTCCTC GTCTTCCTCC
 801  TTCGGGCCTC CGTTGCAGGT TGCAGGTAAC AGAACCGAAG AAATCCTTTT
 851  GGAATGGGTG CCTTCATCCT CCTCCTCTGC TTGCTCGTGC CGTTGGTGCT
 901  CGTGTGCGCC GTCCGCGCCA GGAAGGGCGC CGGCGGGCGG TCGTCGTCGG
 951  GCGGCGGCAA GAAGGGCAGG CTGCCGCCGG GGTCCATGGG GTGGCCGTAC
1001  GTGGGCGAGA CCACGCAGCT CTACTCCTCC AAGAACCCCA ACGTCTTCTT
1051  CGCCAGGAAG CGTAACAAGT ACGGGCCCAT CTTCAAGACG CACATCCTCG
1101  GGTGCCCCTG CGTCATGGTG TCCAGCCCGG AGGCCGCCAA GTTCGTGCTC
1151  GTCACGCAGG CGCACCTCTT CAAGCCTACC TTCCCGGCCA GCAAGGAGCG
1201  GATGCTGGGC CGCCAGGCCA TCTTCTTCCA GCAGGGGAC TACCACACCC
1251  ACCTCCGCCG TCTCGTCTCC CGCGCCTTCT CCCCGAGGC CATCCGCGGC
1301  TCCGTCTCAT CCATCGAGGC CATCGCCCTC CGCTCCCTCG GCTCATGGGA
1351  AGGCCATGAA GTCAACACCT TCAAGAAAT GAAGACTGTA AGTTCTTCTT
1401  CTTCTTCCAT TCCTGCCTCC TCTGTTTTCA TCTGCTCTGC TCTGCTCTGC
1451  GGCTAAATGC TTAGAAATGG TCACTGATGG TTTTGTTGGT GTCATTGCGC
```

FIG. 6

```
1501  AGTACGCTCT GAATGTGGCA TTGCTGTCCA TCTTCGGGGA GGAGGAGATG
1551  CAGTACATCG AGGAGCTGAA GCAGTGCTAC CTGACGCTGG AGAAGGGGTA
1601  CAACTCGATG CCGGTGAACC TGCCGGGCAC GCTGTTCCAC AAGGCCATGA
1651  AGGCCCGGAA GCGGCTGGGC GCCATTGTGG CCCACATCAT CTCAGCCCGG
1701  CGCGAGCGGG AGCGCGGAG CGACCTCCTG GCTCCTTCA TGGACGGCCG
1751  CGAGGCGCTC ACCGACGACC AGATCGCCGA CAACGCCATC GGCGTCATCT
1801  TCGCCGCGCG GGACACCACC GCCAGCGTGC TCACGTGGAT GGTCAAGTTC
1851  CTCGGCGACA ACCCCGCCGT CCTCAAAGCC GTCACCGTAA GTCGCCATCA
1901  AACCGACCAG CTGACCCGCT TTGGCACCCC GGCATGTCGA AAGGCAGTGT
1951  CTCTGACCCG CGCGCGTGAA ACGATTGACA ACAGGAAGAG CACGCCGAGA
2001  TCGCGAGGGA GAAGGCGTTG TCCGGCGAGC CGCTGTCGTG GGCAGACACG
2051  CGGCGGATGC GGGTGACGGG CCGGGTGATC CAGGAGACGA TGCGGGTGGC
2101  GTCCATCCTC TCCTTCACCT TCAGAGAGGC CGTCGAGGAC GTGGAGTACC
2151  AAGGTGAGCA CTGAGCTCTG AGCAGAGACA TCAATCAACT TCGCTTTGGT
2201  CGTTTGCGGC AGCGCACTGC TGTACCGTGC TGTACCTCTC GGAGTACAGC
2251  TACAGCAGTG CGCTGCCTGC GCATGAACTG GCTCGGAAAG GACGTGCTCC
2301  TAACCGAACG GACGAAATAG ACCAACAACT CGAACTCGCA ACTCACCTCG
2351  GCTCGGCTCG CTCCTCCGTG CAGGGTACCT GATCCCCAAG GGCTGGAAAG
2401  TGCTTCCCCT GTTCGGAAC ATCCACCACA ACCCCGACCA CTTCCCCTCC
2451  CCCGAAAAGT TCGATCCTTC ACGATTCGAG GTCAGCATCA TCACATCTTC
2501  TTCTTCTACT GTTTTTTTT TCCTTGGATG ATGATGATGA TAGGCTTGAG
2551  AGTCCCCCGT TGTTCATTAG CTGATTGCGT TTTTGTTCTT GGTGACTGCA
2601  GGTGGCCCCC AAGCCCAACA CGTTCATGCC GTTCGGGAAC GGGACCCACT
2651  CGTGCCCCGG CAACGAGCTG GCCAAGCTGG AGATGCTCGT CCTCTGCCAC
2701  CACCTCGCCA CCAAGTACAG ATGGTCTACC TCCAAGTCCG AGAGCGGCGT
2751  GCAGTTCGGC CCCTTCGCCC TGCCCATCAA CGGCCTCCCC ATGACCTTCA
2801  CCCGCAAGGC TGATCTATGT CTTCCTCCTT CGGAAAATCA ACAGCACGAT
2851  AGAGGCAACG GCGTGGCGCA TGCGAACCGG ATCGGTTCTC CATCCGTCAG
2901  TGTCCGTGCC GGTCGCCGTC GGAGGGGACA CTTGTAGCGG TGGGCGCCGC
2951  GGCGGGAGCT GGCGATGGAT CGGATCGGAG CACGGACCGT CAAAGTCCTT
```

FIG. 6 Continued

```
3001  TGTACAGATT CTTCTTCAGC TAGGACCATG ACGGCCGGGC GAGACAAGAC
3051  CAGGAAAAAA TTCCTGCCCT TCACAAACAC ACACCAGTCA GTGGTAGCAC
3101  TACGTAGGCA TTCTCAGCTA GGGAGATCCG GCGCCACAAA GAAGTGGCGC
3151  CCAACTGTAA AACCAACCAT TTTTTATCCT TTTCTTTCAG
```

FIG. 6 Continued

```
   1  CGAAGAAAGC CTTTCGTTGA CATGGCTGCT TTCATCCTCT TCCTCTGCTT
  51  GCTCGTGCCG CTCGTCCTCG CGTGCGCCGT CCGCGCCAGG AAGGGCGCCA
 101  CCGGGCGGGC GTCGTCGGGC AGCGGCGGCA AAAAGGGCGG CACCAGCCTG
 151  CCGCTGCCGC CGGGGTCGAT GGGCTGGCCG TACGTGGGCG AGACCACGCA
 201  GCTCTACTCC TCCAAGAACC CCAACGTCTT CTTCGCCAGG AAGCGGAACA
 251  AGTACGGGCC CATCTTCAAG ACGCACATCC TCGGGTGCCC CTGCGTCATG
 301  GTGTCCAGCC CGGAGGCCGC CAAGTTCGTG CTCGTCACTC AGGCGCACCT
 351  CTTCAAGCCT ACCTTCCCGG CCAGCAAGGA GCGGATGCTG GGCCCCCAGG
 401  CCATCTTCTT CCAGCAGGGG GACTACCATG CCCACCTCCG CCGTCTCGTC
 451  TCACGCGCCT TCTCTCCCGA GGCCATCCGC GGTTCCGTCC CTGCCATCGA
 501  GGCTATCGCC CTCCGCTCCC CCGGCTCCTG GAAGACCTG CAAGTCAACA
 551  CCTTCCAAGA GATGAAGACT GTGAGTGCTT CTTCCTCTTC CATTCCCGCT
 601  TGCTCTGCTT TCCTCTGCTC TGCTCTACTG CTAAATGATT GGAGCTCGAG
 651  GCTGATCCTT CTCTTGGTGT CGTGGCGCAG TACGCTCTGA ATGTGGCATT
 701  GCTGTCCATC TTCGGCGACG AGGAGATGCA GTACATCGAG GAGCTGAAGC
 751  AGTGCTACCT GACGCTGGAG AAGGGGTACA ACTCGATGCC GGTGAACCTG
 801  CCGGGCACGC TGTTCCACAA GGCCATGAAG GCCCGAAAGC GGCTGGGCGC
 851  CATTGTGGCC CACATCATCT CGGCCCGGCG CGAGCGCGAG CGCGGGAGCG
 901  ACCTCCTGGG CTCCTTCATG GACGGCCGCG AGGCGCTCAC CGACGACCAG
 951  ATCGCCGACA ACGCCATCGG CGTCATCTTC GCCGCGCGCG ACACCACCGC
1001  CAGCGTGCTC ACGTGGATGG TCAAGTTCCT CGGCGACAAC CCCGCCGTCC
1051  TCAAAGCCGT CACCGTAAGT CGCCATCAAC CAGCTGACCC GCTTGGTACC
1101  CGATCGAAAA GCAGTGGCTG ACCCGTGCGT CGTACGATTA ACAGGAAGAG
1151  CACGCTGAGA TCGCGAGGGA GAAGGCGTTG TCCGGCGAGC CACTGTCGTG
1201  GGCCGACACG CGGCGGATGC GGATGACGGG CCGGGTGATC CAGGAGACGA
1251  TGCGGGTGGC GTCCATCCTC TCCTTCACCT TCAGGCAGGC CGTGGAGGAC
1301  GTGGAGTACC AAGGTGAGCA GAGCAGAGAC ATCAATCGCT TTGGTCGTTT
1351  GTGGCAGCGC AGCGCTGTAC TCCGCTGTCC CTCTCGGAGT ACAGCAGTGA
1401  GCTGCCTGCC TGCCTGCGCA TGAACTGGCT CGGAAAGGAC GCGCTCCTAA
1451  CCGAACGAAC GAAATAGACC AACTCAAACT CGCAACTCAC CTCGGCTTGC
1501  TCTCCTCTGT GCGTGCAGGG TACCTGATTC CCAAGGGCTG GAAAGTGCTT
```

FIG. 12

```
1551  CCCCTGTTCC GGAACATCCA CCACAACCCC GACCACTTCC CCTCCCCTGA
1601  AAAGTTCGAT CCTTCACGAT TCGAGGTCAG CATCATCACA GCCCTCTGTT
1651  TGACGAGTCT GCTTCGATTC GGTTGATCAT TATCTGATTA TACGTTTTGG
1701  TTGCTGACTG CAGGTGGCCC CCAAGCCCAA CACGTTCATG CCGTTCGGGA
1751  ACGGGACCCA CTCGTGCCCC GGCAACGAGC TGGCCAAGCT GGAGATGCTC
1801  GTCCTCTGCC ACCACCTCGC CACCAAGTAC AGATGGTCCA CCTCCAAGTC
1851  CGAGAGCGGC GTCCAGTTCG GCCCCTTCGC CCTCCCCATC AACGGCCTCC
1901  CCATGACCTT CACCCGCAAG GACGACAAGA ACAAAGCCTG AGCCATCCAT
1951  CCATCCATCC ATCCATCGCC TCCTCCTCGT TCCCAAAGGG AAAT
```

FIG. 12 Continued

```
Sequence  1         11         21         31         41         51
fgt1871   GCTCACGTGGATGGTCAAGTTCCTCGGCGACAACCCCGCCGTGCTCAAAGCCGTCACCGT
fgt1886   GCTCACGTGGATGGTCAAGTTCCTCGGCGACAACCCCGCCGTGCTCAAAGCCGTCACCGT
fgt1880   GCTCACGTGGATGGTCAAGTTCCTCGGCGACAACCCCGCCGTGCTCAAAGCCGTCACCGT
fgt1868   GCTCACGTGGATGGTCAAGTTCCTCGGCGACAACCCCGCCGTCCTCAAAGCCGTCACCGT
fgt1882   GCTCACGTGGATGGTCAAGTTCCTCGGCGACAACCCCGCCGTCCTCAAAGCCGTCACCGT
fgt1864   GCTCACGTGGATGGTCAAGTTCCTCGGCGACAACCCCGCCGTCCTCAAAGCCGTCACCGT
fgt1865   GCTCACGTGGATGGTCAAGTTCCTCGGCGACAACCCCGCCGTCCTCAAAGCCGTCACCGT
fgt1878   GCTCACGTGGATGGTCAAGTTCCTCGGCGACAACCCCGCCGTCCTCAAAGCCGTCACCGT
fgt1876   GCTCACGTGGATGGTCAAGTTCCTCGGCGACAACCCCGCCGTGCTCAAAGCCGTCACCGT
fgt1873   GCTCACGTGGATGGTCAAGTTCCTCGGCGACAACCCCGCCGTCCTCAAAGCCGTCACCGT
fgt1870   GCTCACGTGGATGGTCAAGTTCCTCGGCGACAACCCCGCCGTCCTCAAAGCCGTCACCGT 61         71         81         91         101        111
fgt1871   AAGTCGCCATC.........AACCAGCTGACCCGCTTGGTACCCGATCGAAAAGCAGCGA
fgt1886   AAGTCGCCATC.........AACCAGCTGACCCGCTTGGTACCCGATCGAAAAGCAGCGA
fgt1880   AAGTCGCCATC.........AACCAGCTGACCCGCTTGGTACCCGATCGAAAAGCAGCGA
fgt1868   AAGTCGCCATC.........AACCAGCTGACCCGCTTGGTACCCGATCGAAAAGCAGTGG
fgt1882   AAGTCGCCATC.........AACCAGCTGACCCGCTTGGTACCCGATCGAAAAGCAGTGG
fgt1864   AAGTCGCCATC.........AACCAGCTGACCCGCTTGGTACCCGATCGAAAAGCAGTGG
fgt1865   AAGTCGCCATC.........AACCAGCTGACCCGCTTGGTACCCGATCGAAAAGCAGTGG
fgt1878   AAGTCGCCATC.........AACCAGCTGACCCGCTTGGTACCCGATCGAAAAGCAGTGG
fgt1876   AAGTCGCCATC.........AACCAGCTGACCCGCTTGGTACCCGATCGAAAAGCAGCGA
fgt1873   AAGTCGCCGTCATTTCATGAACCCAGCTGACCCGCTAGGCACCCGATCGAAAAGCAGCGA
fgt1870   AAGTCGCCGTCATTTCATGAACCCAGCTGACCCGCTAGGCACCCGATCGAAAAGCAGCGA 121        131        141        151        161        171
fgt1871   CTGACCCGTGCATCCAACAATTAACAGGAAGAGCATGCCGAGATCGCGAGGGAGAAGGCG
fgt1886   CTGACCCGTGCATCCAACAATTAACAGGAAGAGCATGCCGAGATCGCGAGGGAGAAGGCG
fgt1880   CTGACCCGTGCATCCAACAATTAACAGGAAGAGCATGCCGAGATCGCGAGGGAGAAGGCG
fgt1868   CTGACCCGTGCGTCGTACAATTAACAGGAAGAGCACGCTGAGATCGCGAGGGAGAAGGCG
fgt1882   CTGACCCGTGCGTCGTACAATTAACAGGAAGAGCACGCTGAGATCGCGAGGGAGAAGGCG
fgt1864   CTGACCCGTGCGTCGTACAATTAACAGGAAGAGCACGCTGAGATCGCGAGGGAGAAGGCG
fgt1865   CTGACCCGTGCGTCGTACAATTAACAGGAAGAGCACGCTGAGATCGCGAGGGAGAAGGCG
fgt1878   CTGACCCGTGCGTCGTACAATTAACAGGAAGAGCACGCTGAGATCGCGAGGGAGAAGGCG
fgt1876   CTGACCCGTGCATCCAACAATTAGCAGGAAGAGCATGCCGAGATCGCGAGGGAGAAGGCG
fgt1873   CTGACTCGTTCATCATACAATCAACAGGAAGGGCACGCCGAGATCGCGAGGGAGAAGGCG
fgt1870   CTGACTCGTTCATCATACAATCAACAGGAAGAGCACGCCGAGATCGCGAGGGAGAAGGCG 181        191        201        211        221        231
fgt1871   TTGTCCGGCGAGCCGCTGTCGTGGGCCGACACGCGGCGGATGCGGATGACGGGCCGGGTG
fgt1886   TTGTCCGGCGAGCCGCTGTCGTGGGCCGACACGCGGCGGATGCGGATGACGGGCCGGGTG
fgt1880   TTGACCGGCGAGCCGCTGTCGTGGGCCGACACGCGGCGGATGCGGATGACGGGCCGGGTG
fgt1868   TTGTCCGGCGAGCCACTGTCGTGGGCCGACACGCGGCGGATGCGGATGACGGGCCGGGTG
fgt1882   TTGTCCGGCGAGCCACTGTCGTGGGCCGACACGCGGCGGATGCGGATGACGGGCCGGGTG
fgt1864   TTGTCCGGCGAGCCACTGTCGTGGGCCGACACGCGGCGGATGCGGATGACGGGCCGGGTG
fgt1865   TTGTCCGGCGAGCCACTGTCGTGGGCCGACACGCGGCGGATGCGGATGACGGGCCGGGTG
fgt1878   TTGTCCGGCGAGCCGCTGTCGTGGGCCGACACGCGGCGGATGCGGATGACGGGCCGGGTG
fgt1876   TTGTCCGGCGAGCCGCTGTCGTGGGCCGACACGCGGCGGATGCGGATGACGGGCCGGGTG
fgt1873   TTGTCCGGCGAGCCACTGTCGTGGGCCGACACGCGGCGGATGCGGATGACGGGCCGGGTG
fgt1870   TTGTCCGGCGAGGCGCTGTCGTGGGCCGACACGCGGCGGATGCGGTTGACGGGCCGGGTG 241        251        261        271        281        291
fgt1871   ATCCAGGAGACGATGCGGGTGGCGTCCATCCTCTCCTTCACCTTCAGGGAGGCCGTGGAG
fgt1886   ATCCAGGAGACGATGCGGGTGGCGTCCATCCTCTCCTTCACCTTCAGGGAGGCCGTGGAG
fgt1880   ATCCAGGAGACGATGCGGGTGGCGTCCATCCTCTCCTTCACCTTCAGGGAGGCCGTGGAG
fgt1868   ATCCAGGAGACGATGCGGGTGGCGTCCATCCTCTCCTTCACCTTCAGGGAGGCCGTGGAG
fgt1882   ATCCAGGAGACGATGCGGGTGGTGTCCATCCTCTCCTTCACCTTCAGGGAGGCCGTGGAG
fgt1864   ATCCAGGAGACGATGCGGGTGGCGTCCATCCTCTCTCTTCACCTTCAGGGAGGCCGTGGAG
fgt1865   ATCCAGGAGACGATGCGGGTGGCGTCCATCCTCTCCTTCACCTTCAGGGAGGCCGTGGAG
fgt1878   ATCCAGGAGACGATGCGGGTGGCGTCCATCCTCTCCTTCACCTTCAGGGAGGCCGTGGAG
```

FIG. 13

```
fgt1876   ATCCAGGAGACGATGCGGGTGGCGTCCATCCTCTCCTTCACCTTCAGGGAGGCCGTGGAG
fgt1873   ATCCAGGAGACGATGCGGGTGGCGTCCATCCTCTCCTTCACCTTCAGGGAGGCCGTGGAG
fgt1870   ATCCAGGAGACGATGCGGGTGGCGTCCATCCTCTCCTTCACCTTCAGGGAGGCCGTGGAG 301       311       321       331       341       351
fgt1871   GACGTGGAGTACCAAGGTGAGACATCAATCAACTTCGCGCGCGCGCGCGCTTTGGTCGTT
fgt1886   GACGTGGAGTACCAAGGTGAGACATCAATCAACTTCGCGCGCGCGCGCGCTTTGGTCGTT
fgt1880   GACGTGGAGTACCAAGGTGAGACATCAATCAACTT....CGCGCGCGCGCTTTGGTCGTT
fgt1868   GACGTGGAGTACCAAGGTGAGCAGAGCAGAGACAT........CAATCGCTTTGGTCGTT
fgt1882   GACGTGGAGTACCAAGGTGAGCAGAGCAGAGACAT........CAATCGCTTTGGTCGTT
fgt1864   GACGTGGAGTACCAAGGTGAGCAGAGCAGAGACAT........CAATCGCTTTGGTCGTT
fgt1865   GACGTGGAGTACCAAGGTGAGCAGAGCAGAGACAT........CAATCGCTTTGGTCGTT
fgt1878   GACGTGGAGTACCAAGGTGAGCAGAGCAGAGACAT........CAATCGCTTTGGTCGTT
fgt1876   GACGTGGAGTACCAAGGTGAGCAGAGCAGAGACAT........CAATCGCTTTGGTCGTT
fgt1873   GACGTGGAGTACCAAGGTGAGCAGAGCAGAGACAT........CAATCGCTTTGGTCGTT
fgt1870   GACGTGGAGTACCAAGGTGAGCAGAGCAGAGGCAT........CAATCGCTTTGGTCGTT 361       371       381       391       401       411
fgt1871   TGCGGCAGCGCAGCGCCGTACTGTGCTGTCCCTCTCGGAGTACAGCAGTGCGCTGCCTGC
fgt1886   TGCGGCAGCGCAGCGCCGTACTGTGCTGTCCCTCTCGGAGTACAGCAGTGCGCTGCCTGC
fgt1880   TGCGGCAGCGCAGCGCCGTACTGTGCTGTCCCTCTCGGAGTACAGCAGTGCGCTGCCTGC
fgt1868   TGTGGCAGCGCAGTGCTGTACTCCGCTGTCCCTCTCGGAGTACAGCAGTGAGCTGCCTGC
fgt1882   TGTGGCAGCGCAGTGCTGTACTCCGCTGTCCCTCTCGGAGTACAGCAGTGAGCTGCCTGC
fgt1864   TGTGGCAGCGCAGTGCTGTACTCCGCTGTCCCTCTCGGAGTACAGCAGTGAGCTGCCTGC
fgt1865   TGTGGCAGCGCAGTGCTGTACTCCGCTGTCCCTCTCGGAGTACAGCAGTGAGCTGCCTGC
fgt1878   TGTGGCAGCGCAGTGCTGTACTCCGCTGTCCCTCTCGGAGTACAGCAGTGAGCTGCCTGC
fgt1876   TGTGGCAGCGCAGTGCTGTACTCCGCTGTCCCTCTCGGAGTACAGCAGTGAGCTGCCTGC
fgt1873   TGTGGCAGCGCAGTGCTGTACTCCGCTGTCCCTCTCGGAGTACAGCAGTGAGCTGCCTGC
fgt1870   TGAGGCAGCGCAGTGCTGTGCTCCGCTGTCCTTCTCGGAGCACAGCAGTGCGCTGCCTGC 421       431       441       451       461       471
fgt1871   CTGCCTGCGCATGAACTGGCTCGGAAAGGACGTGCTCCTAACCGAACG...GGAATAGAC
fgt1886   CTGCCTGCGCATGAACTGGCTCGGAAAGGACGTGCTCCTAACCGAACG...GGAATAGAC
fgt1880   CTGCCTGCGCATGAACTGGCTCGGAAAGGACGTGCTCCTAACCGAACG...GGAATAGAC
fgt1868   CTGCCTGCGCATGAACTGGCTCGGAAAGGACGCGCTCCTAACCGAACGAACGAAATAGAC
fgt1882   CTGCCTGCGCATGAACTGGCTCGGAAAGGACGCGCTCCTAACCGAACGAACGAAATAGAC
fgt1864   CTGCCTGCGCATGAACTGGCTCGGAAAGGACGCGCTCCTAACCGAACGAACGAAATAGAC
fgt1865   CTGCCTGCGCATGAACTGGCTCGGAAAGGACGCGCTCCTAACCGAACGAACGAAATAGAC
fgt1878   CTGCCTGCGCATGAACTGGCTCGGAAAGGACGCGCTCCTAACCGAACGAACGAAATAGAC
fgt1876   CTGCCTGCGCATGAACTGGCTCGGAAAGGACGCGCTCCTAACCGAACGAACGAAATAGAC
fgt1873   CTGCCTGCGCATGAACTGGCTCGGAAAGGACGCGCTCCTAACCGAACGAACGAAATAGAC
fgt1870   CCGCCTGC.......CTGCCTGCGCATGAACTGGCTCGGAAAGGA...CGCGCTCCTAACT 481       491       501       511       521       531
fgt1871   CAACTCGAACTCGCAACTCACCTCGACTCGCTCTCTTCTGTGCGTGCAGGGTACCTGATT
fgt1886   CAACTCGAACTCGCAACTCACCTCGACTCGCTCTCTTCTGTGCGTGCAGGGTACCTGATT
fgt1880   CAACTCGAACTCGCAACTCACCTCGACTCGCTCTCTTCTGTGCGTGCAGGGTACCTGATT
fgt1868   CAACTCAAACTCGCAACTCACCTCGACTTGCTCTCCTCTGTGCGTGCAGGGTACCTGATT
fgt1882   CAACTCAAACTCGCAACTCACCTCGACTTGCTCTCCTCTGTGCGTGCAGGGTACCTGATT
fgt1864   CAACTCAAACTCGCAACTCACCTCGACTTGCTCTCCTCTGTGCGTGCAGGGTACCTGATT
fgt1865   CAACTCAAACTCGCAACTCACCTCGACTTGCTCTCCTCTGTGCGTGCAGGGTACCTGATT
fgt1878   CAACTCAAACTCGCAACTCACCTCGACTTGCTCTCCTCTGTGCGTGCAGGGTACCTGATT
fgt1876   CAACTCAAACTCGCAACTCACCTCGACTTGCTCTCCTCTGTGCGTGCAGGGTACCTGATT
fgt1873   CAACTCAAACTCGCAACTCACCTCGACTTGCTCTCCTCTGTGCGTGCAGGGTACCTGATT
fgt1870   CAAGGGAAACTCGCAACTCACCTCGACTTGCTCTCCTCTGTGCGTGCAGGGTACCTGATT 541       551       561       571       581       591
fgt1871   CCCAAGGGCTGGAAAGTGCTTCCCCTGTTCCGGAACATCCACCACAACCCCGACCACTTC
fgt1886   CCCAAGGGCCGGAAAGTGCTTCCCCTGTTCCGGAACATCCACCACAACCCCGACCACTTC
fgt1880   CCCAAGGGCTGGAAAGTGCTTCCCCTGTTCCGGAACATCCACCACAACCCCGACCACTTC
fgt1868   CCCAAGGGCTGGAAAGTGCTTCCCCTGTTCCGGAACATCCACCACAACCCCGACCACTTC
```

FIG. 13 Continued

```
fgt1882   CCCAAGGGCTGGAAAGTGCTTCCCCTGTTCCGGAACATCCACCACAACCCCGACCACTTC
fgt1864   CCCAAGGGCTGGAAAGTGCTTCCCCTGTCCGGAACATCCACCACAACCCCGACCACTTC
fgt1865   CCCAAGGGCTGGAAAGTGCTTCCCCTGTTCCGGAACATCCACCACAACCCCGACCACTTC
fgt1878   CCCAAGGGCTGGAAAGTGCTTCCCCTGTTCCGGAACATCCACCACAACCCCGACCACTTC
fgt1876   CCCAAGGGCTGGAAAGTGCTTCCCCTGTTCCGGAACATCCACCACAACCCCGACCACTTC
fgt1873   CCCAAGGGCTGGAAAGTGCTTCCCCTGTTCCGGAACATCCACCACAACCCCGACCACTTC
fgt1870   CCCAAGGGCTGGAAAGTGCTTCCCCTGTTCCGGAACATCCACCACAACCCCGACCACTTC 601       611       621       631       641       651
fgt1871   CCCTCCCCCGAAAAGTTCGATCCTTCACGATTCGAGGTCAGCATCA....TCACAGCCCT
fgt1886   CCCTCCCCCGAAAAGTTCGATCCTTCACGATTCGAGGTCAGCATCA....TAACAACCCT
fgt1880   CCCTCCCCCGAAAAGTTCGATCCTTCACGATTCGAGGTCAGCATCA....TAACAACCCT
fgt1868   CCCTCCCCTGAAAAGTTCGATCCTTCACGATTCGAGGTCAGCATCA....TCACAGCCCT
fgt1882   CCCTCCCCTGAAAAGTTCGATCCTTCACGATTCGAGGTCAGCATCA....TCACAGCCCT
fgt1864   CCCTCCCCTGAAAAGTTCGATCCTTCACGATTCGAGGTCAGCATCA....TCACAGCCCT
fgt1865   CCCTCCCCTGAAAAGTTCGATCCTTCACGATTCGAGGTCAGCATCA....TCACAGCCCT
fgt1878   CCCTCCCCTGAAAAGTTCGATCCTTCACGATTCGAGGTCAGCATCA....TCACAGCCCT
fgt1876   CCCTCCCCTGAAAAGTTCGATCCTTCACGATTCGAGGTCAGCATCA....TCACAGCCCT
fgt1873   CCCTCCCCTGAAAAGTTCGATCCTTCACGATTCGAGGTCAGCATCA....TCACAGCCCT
fgt1870   CCCTCCCCCGAAAAGTTCGACCCTTCACGATTCGAGGTCAGCATCATCATTCACAGCCCT 661       671       681       691       701       711
fgt1871   CTGTTTGACGAGTC...TGCTTCGATTCGATTGATCATTATCTG...ATTATACGTTTTG
fgt1886   CTATTTGACGAGCC...TGCTTCGATTCGATTGATCATTATCTG...ATTATACGTTTTG
fgt1880   CTATTTGACGAGCC...TGCTTCGATTCGATTGATCATTATCTG...ATTATACGTTTTG
fgt1868   CTGTTTGACGAGTC...TGCTTCGATTCGATTGATCATTATCTG...ATTATACGTTTTG
fgt1882   CTGTTTGACGAGTC...TGCTTCGATTCGATTGATCATTATCTG...ATTATACGTTTTG
fgt1864   CTGTTTGACGAGTC...TGCTTCGATTCGATTGATCATTATCTG...ATTATACGTTTTG
fgt1865   CTGTTTGACGAGTC...TGCTTCGATTCGATTGATCATTATCTG...ATTATACGTTTTG
fgt1878   CTGTTTGACGAGTC...TGCTTCGATTCGGTTGATCATTATCTG...ATTATACGTTTTG
fgt1876   CTGTTTGACGAGTC...TGCTTCGATTCGATTGATCATTATCTG...ATTATACGTTTTG
fgt1873   CTGTTTGACGAGTC...TGCTTCGATTCGATTGATCATTATCTG...ATTATACGTTTTG
fgt1870   CTGTTTGACGAGTCTCTTCTTCGATTTCGATTGATCGTTATCTGATTATTATACGTCTTG 721       731       741       751       761       771
fgt1871   GTTCGTGACTGCAGGTGGCCCCCAAGCCCAACACGTTCATGCCGTTCGGGAA
fgt1886   GTTCGTGACTGCAGGTGGCCCCCAAGCCCAACACGTTCATGCCGTTCGGGAA
fgt1880   GTTCGTGACTGCAGGT.GCCCCCAAGCCCAACACGTTCATGCCGTTCGGGAA
fgt1868   GTTGCTGACTGCAGGTGGCCCCCAAGCCCAACACGTTCATGCCGTTCGGGAA
fgt1882   GTTGCTGACTGCAGGTGGCCCCCAAGCCCAACACGTTCATGCCGTTCGGGAA
fgt1864   GTTGCTGACTGCAGGTGGCCCCCAAGCCCAACACGTTCATGCCGTTCGGGAA
fgt1865   GTTGCTGTCTGCAGGTGGCCGCCAAGCCCAACACGTTCATGCCGTTCGGGAA
fgt1878   GTTGCTGACTGCAGGTGGCCCCCAAGCCCAACACGTTCATGCCGTTCGGGAA
fgt1876   GTTGCTGACTGCAGGTGGCCCCCAAGCCCAACACGTTCATGCCGTTCGGGA~
fgt1873   GTTGCTGACTGCAGGTGGCCCCCAAGCCCAACACGTTCATGCCGTTCGGGAA
fgt1870   GTTCGTGACTGCAGGTGGCCCCCAAGCCCAACACGTTCATGCCGTTCGGGAA
```

FIG. 13 Continued

(a)
(b)
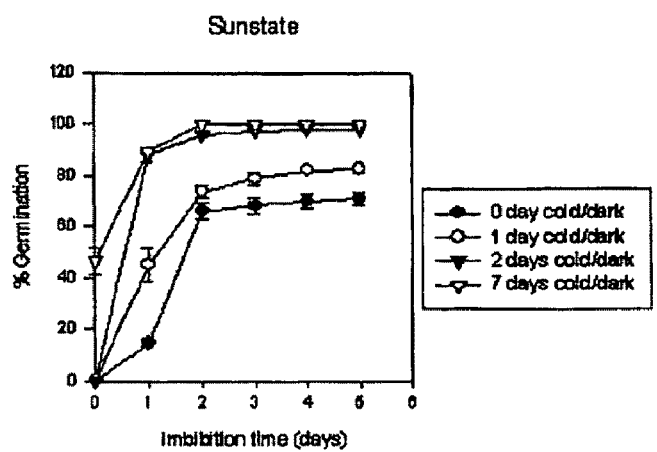
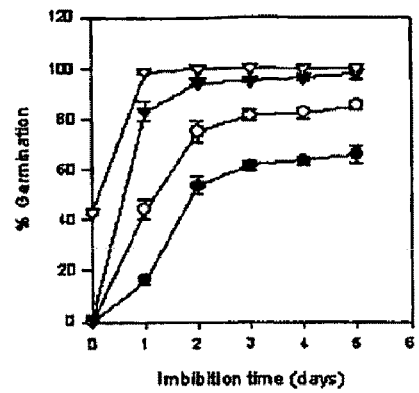
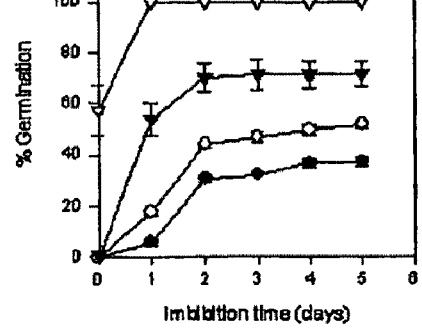
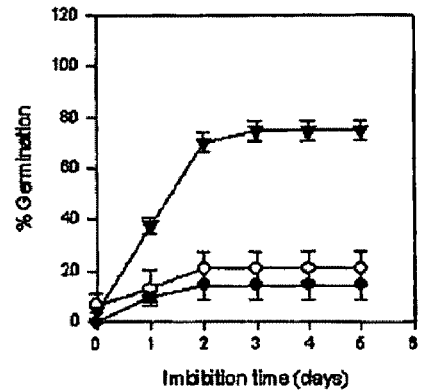
(c)
(d)
Figure 17

CEREALS WITH ALTERED DORMANCY

This application is a §371 national stage of PCT International Application No. PCT/AU2006/001556, filed Oct. 19, 2006, and claims the benefit of U.S. Provisional Application No. 60/729,460, filed Oct. 20, 2005, the contents of all of which are hereby incorporated by reference into this application.

FIELD OF THE INVENTION

The present invention relates to polypeptides, and polynucleotides encoding therefor, which influence seed dormancy in cereals such as wheat and barley. In particular, the present invention relates to polypeptides with ABA 8'-hydroxylase activity, and polynucleotides encoding these proteins. Also provided are cereal plants, obtained from plant breeding programs and/or through genetic manipulation, which produce seeds that have altered rates of germination, and/or levels of dormancy, when compared to seeds from wild-type plants.

BACKGROUND OF THE INVENTION

Germination is one of the most important "decisions" in the life-history of a plant, as it sets in motion the growth of the seedling. Therefore it is not surprising that seed dormancy is a complex trait, influenced by a myriad of genetic and environmental factors that interact to maximize the long-term chance of survival of the seed (Koornneef et al., 2002). Many of these factors are mediated by hormones, with gibberellic acid (GA), ethylene and brassinosteriods all known to promote germination, and abscisic acid (ABA) known to promote dormancy (Koornneef et al., 2002).

During seed development, ABA content increases and regulates many key processes including the imposition and maintenance of dormancy (Bewley, 1997). This is illustrated by ABA-deficient mutants of maize that display vivipary (McCarty, 1995) and by ABA-deficient mutants of *Arabidopsis* that can germinate in the absence of GA (Koornneef et al., 1982). Upon imbibition, this high level of ABA must be reduced in order for the seeds to germinate, and recent studies have shown that this occurs when dormancy is broken by after-ripening, stratification, dark or treatment with smoke water (for review see Gubler et al., 2005). For example, in after-ripened non-dormant (ND) *Arabidopsis* seeds, upon imbibition ABA levels decline rapidly after which germination proceeds (Ali-Rachedi et al., 2004). In contrast, although the ABA level also declines in imbibed dormant (D) seed, it does so to a lesser extent and only transiently, with ABA content again increasing to levels similar to that observed in the non-imbibed seeds (Ali-Rachedi et al., 2004).

Physiological processes mediated by ABA are usually correlated with fluctuating endogenous levels of the hormone. These levels may be regulated through the balance of biosynthesis and catabolism, with biosynthesis dominating when levels are increasing and catabolism dominating when levels are decreasing. In plants, ABA is synthesized indirectly from carotenoids (Seo and Koshiba, 2002), with the first committed step being catalyzed by the enzyme, 9-cis epoxycarotenoid dioxygenase (NCED), which cleaves 9-cis xanthophylls to xanthoxin, an ABA precursor (Schwartz et al., 1997). A direct correlation between NCED mRNA levels, NCED protein and ABA levels in water-stressed tissues suggest that this step plays a strong regulatory role in many plant species (Qin and Zeevaart, 1999). Additional evidence comes from several instances of over-expression of this enzyme in transgenic plants which leads to higher ABA levels that direct physiological processes (Iuchi et al., 2001) including increasing seed dormancy (Thompson et al., 2000; Qin and Zeevaart, 2002).

ABA levels may not be controlled solely by NCED, as overexpression of a gene encoding zeaxanthin epoxidase (ZEP) in transgenic tobacco resulted in increased ABA levels in mature seed and greater seed dormancy, although the effect of ZEP overexpression was limited (Frey et al., 1999). Furthermore, treatment with the ABA biosynthesis inhibitor fluridone (Grappin et al., 2000) can reduce seed dormancy, indicating that ABA biosynthesis is active in the imbibing seed. Together these experiments indicate that increased ABA biosynthesis can lead to greater seed dormancy.

Several alternative catabolic pathways exist for the inactivation of ABA (Cutler and Krochko, 1999; Zhou et al., 2004). One pathway is the hydroxylation of ABA at the 8'-position to produce 8'-hydroxy ABA, which spontaneously isomerizes to phaseic acid (PA) (Cutler and Krochko, 1999). PA may be further catabolised by a reductase to dihydrophaseic acid (FIG. 1).

In both barley and *Arabidopsis*, the decrease in ABA during seed imbibition is associated with increases in PA, consistent with this catabolism pathway (Jacobsen et al., 2002; Kushiro et al., 2004). The first reaction is catalysed by a cytochrome P450 monooxygenase known as ABA 8'-hydroxylase (ABA8'OH, Krochko et al., 1998). The AtCYP707A1-AtCYP707A4 gene subfamily of *Arabidopsis* has recently been shown to encode ABA8'OH activity via heterologous expression in yeast (Kushiro et al., 2004) or insect cells (Saito et al., 2004). Expression studies in *Arabidopsis* showed that AtCYP707A2 was associated with the rapid decline of ABA in germinating seeds (Kushiro et al., 2004). Furthermore, seeds of cyp707a2 mutants accumulated more than six-fold greater ABA content than wild type seeds and consequently were hyperdormant (Kushiro et al., 2004).

Dormancy is an important agricultural trait, with too little dormancy leading to pre-harvest sprouting in cereals (early germination of grains in the head in moist conditions), or too much dormancy causing inability to germinate, delayed or non-uniform germination, all of which would give rise to poor establishment of crops in the field and poor grain performance in processes such as malting of barley. Two proteins have been identified from rice which are involved in inactivation of ABA (WO2004/113527). However, there is a need for cereals with modified dormancy, in particular of barley and wheat.

SUMMARY OF THE INVENTION

In previous studies, it was concluded that no clear relationship existed between the ABA content of the mature seed/grain of cereals and its level of dormancy (King, 1989). However, the present inventors have identified an association between ABA dynamics in cereal grains and dormancy. Furthermore, many proteins, including proteins with a similar function encoded by separate genes, have been suggested to be involved in ABA synthesis and catabolism in plants. Of these proteins, the present inventors have identified specific molecules that can be manipulated by a variety of techniques to modulate dormancy traits in cereals.

Thus, in a first aspect, the present invention provides a cereal plant comprising a genetic variation which modifies ABA 8'-hydroxylase activity in the seed of said cereal plant, wherein said variation is an introduced mutation in a gene encoding a ABA 8'-hydroxylase, a combination of mutations in at least two ABA 8'-hydroxylase genes, a transgene encoding wheat or barley ABA 8'-hydroxylase or mutant thereof, or a molecule which down-regulates the level of ABA 8'-hydroxylase activity in the seed.

Preferably, the plant is wheat or barley. In a further preferred embodiment, the plant is not rice.

In another preferred embodiment, the ABA 8'-hydroxylase activity is encoded by one, two or three ABA8'OH-1 genes which have been found to be preferentially expressed in the embryo of cereal grain, particularly in the coleorhiza of the germinating grain.

Preferably, the modified ABA 8'-hydroxylase activity is increased or decreased in at least the embryo, endosperm or seed of said plant.

Preferably, the ABA 8'-hydroxylase activity is modified in at least the developing grain, the mature grain, or the grain following imbibition.

Preferably, the mutant ABA 8'-hydroxylase comprises a sequence which is at least 88% identical to SEQ ID NO:4, 72% identical to SEQ ID NO:7, 89% identical to SEQ ID NO:10, or is a biologically active fragment thereof. Furthermore, it is preferred that the mutant has ABA 8'-hydroxylase activity.

In another aspect, the present invention provides a substantially purified polypeptide comprising a sequence which is:
  i) an amino acid sequence as provided in SEQ ID NO:4,
  ii) an amino acid sequence as provided in SEQ ID NO:7,
  iii) an amino acid sequence as provided in SEQ ID NO: 10,
  iv) an amino acid sequence which is at least 88% identical to i),
  v) an amino acid sequence which is at least 72% identical to ii),
  vi) an amino acid sequence which is at least 89% identical to iii), or a polypeptide which is a biologically active fragment thereof, wherein the polypeptide has ABA 8'-hydroxylase activity.

In a preferred embodiment, the polypeptide can be purified from wheat or barley.

Preferably, the polypeptide comprises a sequence which is:
  i) an amino acid sequence as provided in SEQ ID NO:4,
  ii) an amino acid sequence as provided in SEQ ID NO:10,
  iii) an amino acid sequence which is at least 88% identical to i),
  iv) an amino acid sequence which is at least 89% identical to ii), or a polypeptide which is a biologically active fragment thereof, wherein the polypeptide has ABA 8'-hydroxylase activity.

In a further embodiment, the invention provides a fusion protein further comprising at least one other polypeptide sequence.

The at least one other polypeptide may be, for example, a polypeptide that enhances the stability of a polypeptide of the present invention, or a polypeptide that assists in the purification of the fusion protein.

In a further aspect, the present invention provides an isolated polynucleotide comprising a sequence which is:
  i) a sequence of nucleotides as provided in SEQ ID NO:1,
  ii) a sequence of nucleotides as provided in SEQ ID NO:3,
  iii) a sequence of nucleotides as provided in SEQ ID NO:6,
  iv) a sequence of nucleotides as provided in SEQ ID NO:9,
  v) a sequence of nucleotides as provided in SEQ ID NO:11,
  vi) a sequence of nucleotides encoding a polypeptide of the invention,
  vii) a sequence of nucleotides which is at least 89% identical to ii),
  viii) a sequence of nucleotides which is at least 80% identical to iii),
  ix) a sequence of nucleotides which is at least 89% identical to iv), or a polynucleotide which hybridises to any one of i) to viii) under stringent conditions.

In a preferred embodiment, the polynucleotide is not an isolated polynucleotide provided as Genbank Accession Numbers CX627697.1, BJ485293.1, BJ483016.1, BJ480761.1, BU974868.1, CA022484.1, CA008406.1, CA002179.1, CA001959.1, CA001009.1, CA592321.1, BQ767999.1, BQ763782.1, BQ763339.1, BQ662339.1, BQ466895.1, AJ461576.1, BM370919.2, BE438953.1, AL508120.1, BG416181.1, CA639805.1, CA642118.1, CA659956.1, CA670869.1, CA673250.1, CA677544.1, CA721849.1, CA735611.1, CA735813.1, CD882263.1, CD901822.1, CD902795.1, CD925850.1, CD933992.1, CD939659.1, CK154783.1, CN011303.1, CV769573.1, CV776255.1, BG313865.1, BE517968.1, BE405680.1, BE414902.1, BJ268697.1, BJ273630.1, BJ278008.1, BJ279470.1, BJ283064.1, BJ284456.1, BJ291883.1, BJ298504.1, BQ162853.1, BI750697.1, BI751849.1, AL817135.1, AL821926.1, BQ838458.1, CA612654.1, BE195625.3, BG415006.1, DB159953.1, or a polynucleotide comprising a sequence of nucleotides provided as SEQ ID NO:90 or SEQ ID NO:91.

In a further preferred embodiment, a polynucleotide which hybridises to any one of i) to viii) under stringent conditions must hybridize substantially along the full length of SEQ ID NO:3, SEQ ID NO:6 and/or SEQ ID NO:9.

Preferably, the polynucleotide is operably linked to a promoter capable of directing expression of the polynucleotide in a cell of a cereal plant. Preferably, the plant is wheat or barley. Preferably, the cell is in the seed of the plant.

Also provided is an isolated oligonucleotide which comprises at least 19 contiguous nucleotides of a polynucleotide of the invention.

Preferably, the oligonucleotide comprises at least 19 contiguous nucleotides of SEQ ID NO:3, SEQ ID NO:6 or SEQ ID NO:9.

In another aspect, the present invention provides an isolated polynucleotide which, when present in a cell of a cereal plant, down-regulates the level of ABA 8'-hydroxylase activity in the cell when compared to a cell that lacks said polynucleotide.

In a preferred embodiment, the polynucleotide is recombinant or non-naturally occurring.

As discussed below, such polynucleotides can be produced in transgenic plants to reduce the level of ABA 8'-hydroxylase activity in the seed of the plant, thus altering the rate of germination, and/or dormancy of the seed when compared to a wild-type plant.

Preferably, the polynucleotide is operably linked to a promoter capable of directing expression of the polynucleotide in a cell of a cereal plant. Preferably, the plant is wheat or barley. Preferably, the cell is in the seed of the plant.

Preferably, the polynucleotides down-regulates expression of at least one ABA 8'-hydroxylase gene, or at least one ABA 8'-hydroxylase-1 and at least one ABA 8'-hydroxylase-2 gene.

Preferably, the polynucleotide is selected from, but not limited to, an antisense polynucleotide, a sense polynucleotide (used for cosuppression), a catalytic polynucleotide, a microRNA and a double stranded RNA.

In one embodiment, the polynucleotide is an antisense polynucleotide which hybridises under physiological conditions to a polynucleotide comprising a sequence of nucleotides as provided in SEQ ID NO:3, SEQ ID NO:6 or SEQ ID NO:9.

In another embodiment, the polynucleotide is a catalytic polynucleotide capable of cleaving a polynucleotide according to the invention.

Examples of such catalytic polynucleotides include, but are not limited to, ribozymes and DNAzymes.

Preferably, the polynucleotide according to the invention which can be cleaved by the catalytic polynucleotide is RNA.

In a further embodiment, the polynucleotide is a double stranded RNA (dsRNA) molecule comprising an oligonucleotide of the invention, wherein the portion of the molecule that is double stranded is at least 19 basepairs in length and comprises said oligonucleotide.

Preferably, the dsRNA is expressed from a single promoter, wherein the strands of the double stranded portion are linked by a single stranded portion.

Examples of a suitable dsRNA's of the invention are provided in Example 7 and Example 10 herein.

In another aspect, the present invention provides a vector comprising or encoding a polynucleotide of the invention.

Preferably, the polynucleotide, or sequence encoding the polynucleotide, is operably linked to a promoter.

Preferably, the promoter confers expression of the polynucleotide preferentially in the embryo, endosperm or developing seed of a cereal plant relative to at least one other tissue or organ of said plant.

In a further aspect, the present invention provides a host cell comprising a vector of the invention, and/or a polynucleotide of the invention.

The present inventors have determined that altering ABA 8'-hydroxylase activity in plants results in modified rates of germination and/or altered dormancy in the grain of the genetically modified plants relative to non-modified grain. The genetically modified plant may be transgenic or non-transgenic.

Accordingly, in another aspect, the present invention provides a genetically modified plant, wherein the plant has increased expression of a polypeptide having ABA 8'-hydroxylase activity relative to a corresponding non-modified plant.

In one embodiment, the plant has been transformed with a polynucleotide of the invention, or the plant is a progeny thereof comprising said polynucleotide. Preferably, the polynucleotide is capable of being expressed to produce a polypeptide of the invention.

In another embodiment, the expression level of at least one endogenous ABA 8'-hydroxylase gene has been increased relative to a corresponding non-modified plant. Preferably, the ABA 8'-hydroxylase gene is a ABA 8'-hydroxylase-1 gene. More preferably, the ABA 8'-hydroxylase-1 gene is a wheat or barley ABA 8'-hydroxylase-1 gene.

In an embodiment, the time taken after the beginning of imbibition for 90% of the viable grain to germinate is altered by at least one day.

In one embodiment, the plant is a barley plant, wherein the rate of germination of grain of the plant is increased relative to a corresponding non-modified barley plant. In a preferred embodiment, the time taken after the beginning of imbibition for 90% of the viable barley grain to germinate is decreased by at least one day.

In yet another aspect, the present invention provides a modified plant, which may be transgenic or non-transgenic, wherein the plant has decreased expression of a polypeptide having ABA 8'-hydroxylase activity relative to a corresponding non-modified plant.

The plant, which may be a cereal plant such as wheat or barley, may be modified to comprise an introduced mutation in an ABA8'-hydroxylase gene, preferably an ABA 8'-hydroxylase-1 gene. The mutation may have been introduced into the plant directly by mutagenesis or indirectly by crossing of two parental plants, one of which comprised the introduced mutation.

In another embodiment, the plant, which may be a polyploid cereal plant such as hexaploid wheat or durum (tetraploid) wheat, may comprise a combination of mutations in at least two or three ABA8'-hydroxylase genes, preferably ABA8'-hydroxylase-1 genes, which mutations may have been introduced or naturally occurring as individual mutations but which combination is not naturally occurring in commercially grown cultivars of the cereal. The two or three mutations may be in the A and B, A and D, B and D, or all three genomes of wheat.

Preferably, the mutations include a D genome mutation and more preferably a D genome null mutation in the ABA8'OH-1 gene. As shown herein, the inventors have identified wheat lines having single null alleles of ABA8'-hydroxylase-1 genes occurring at low frequency after an extensive screening of wheat lines but did not identify any naturally occurring lines comprising two or more mutant alleles. Such mutations may be null mutations.

In an embodiment, the plant is a wheat plant, wherein the rate of germination of grain of the plant is decreased relative to a corresponding non-modified wheat plant. In a preferred embodiment, the time taken after the beginning of imbibition for 90% of the viable wheat grains of the plant to germinate is increased by at least one day.

In an embodiment, the plant is a wheat plant, wherein the dormancy of grain of the plant is increased relative to a corresponding non-modified wheat plant. In a preferred embodiment, less than 90% of the viable grains of the plant have germinated under favourable conditions (including a temperature of 20° C.) five days after the beginning of imbibition. More preferably, less than 90% of the grain have germinated seven days after the beginning of imbibition.

In one embodiment, the plant having been transformed such that it produces a polynucleotide of the invention that down-regulates ABA 8'-hydroxylase activity in a cell, or a progeny plant thereof which produces said polynucleotide, or the plant is a progeny thereof comprising said polynucleotide.

In another embodiment, the plant is a barley plant, which may be transgenic or non-transgenic, wherein the rate of germination of grain of the plant is decreased relative to a corresponding non-modified barley plant. In a preferred embodiment, the time taken after the beginning of imbibition for 90% of the viable barley grains of the plant to germinate is increased by at least one day.

In another aspect, the present invention provides a method of altering the rate of germination and/or dormancy of a seed of a plant, preferable a cereal plant, the method comprising genetically manipulating said plant such that the production of a polypeptide is modified when compared to a wild-type plant, wherein the polypeptide has ABA 8'-hydroxylase activity. The rate of germination may be assessed by determining the percentage of grains that have germinated over time after the beginning of imbibition. Preferably, the rate of germination is determined up to about 21 days after the beginning of imbibition. More preferably, the percentage germination is determined at one or more time points about 1, 2, 3, 5 or 7 days after the beginning of imbibition.

In an embodiment, the time taken after the beginning of imbibition for 90% of the viable seed to germinate is altered by at least one day.

Preferably, the polypeptide comprises a sequence which is:
  i) an amino acid sequence as provided in SEQ ID NO:4,
  ii) an amino acid sequence as provided in SEQ ID NO:10, iii) an amino acid sequence which is at least 88% identical to i), iv) an amino acid sequence which is at least 89% identical to ii), or a polypeptide which is a biologically active fragment thereof, wherein the polypeptide has ABA 8'-hydroxylase activity.

The method may comprise a step of introducing a polynucleotide of the invention into a plant cell, tissue or organ, also termed transformation, regenerating a transformed plant, and producing progeny comprising the polynucleotide. The method may comprise a step of crossing two parental plants to combine one or more genetic variations in a progeny plant. The method may also comprise a step of determining the rate of germination and/or dormancy of seed obtained from the plant, or a step of selecting a plant capable of producing seed with an altered rate of germination and/or dormancy relative to a non-modified plant, either step may use a method of detecting one or more genotypic variations in the plant or assessing the phenotype of the plant or its seed.

The present invention also provides methods of identifying alleles of ABA 8'-hydroxylase genes from cereal plants, such as wheat and barley, that confer upon the seeds of the plant a desired rate of germination, and/or level of dormancy.

Thus, in another aspect, the present invention provides a method of genotyping a cereal plant, the method comprising detecting a nucleic acid of the plant or a polypeptide encoded thereby, wherein the nucleic acid molecule is linked to, and/or comprises at least part of, an ABA 8'-hydroxylase gene.

Preferably, the ABA 8'-hydroxylase gene is an ABA 8'-hydroxylase-1 gene.

In one embodiment, the method comprises determining the level of expression, and/or sequence, of a nucleic acid molecule of the plant encoding a polypeptide having ABA 8'-hydroxylase activity. Any suitable technique known in the art can be used such as, but not limited to, restriction fragment length polymorphism analysis, amplification fragment length polymorphism analysis, microsatellite amplification and/or nucleic acid sequencing.

In another embodiment, the method comprises determining the level and/or activity, of a polypeptide having ABA 8'-hydroxylase activity. Again, any suitable technique known in the art can be used such as, but not limited to, detection of ABA 8'-hydroxylase protein levels using an antibody of the invention.

The markers of the invention can be used in cereal plant breeding programs to select progeny plants which possess an allele of an ABA 8'-hydroxylase gene of interest.

Thus, in another aspect the present invention provides a method of selecting a cereal plant from a population of cereal plants, the method comprising;

i) genotyping said population of plants using a method of the invention, wherein said population of plants was obtained from a cross between two plants of which at least one plant comprises an allele of an ABA 8'-hydroxylase gene which confers upon seed of said plant an altered rate of germination, altered dormancy and/or an altered level of ABA 8'-hydroxylase activity, when compared to seed of the cereal plant lacking said allele, and ii) selecting said cereal plant on the basis of the presence or absence of said allele.

Preferably, the ABA 8'-hydroxylase gene is an ABA 8'-hydroxylase-1 gene.

Preferably, the population is at least 10 plants, more preferably at least 20 to 50 plants.

Preferably, the allele of an ABA 8'-hydroxylase gene which confers upon seed of said plant an altered rate of germination, altered dormancy and/or an altered level of ABA 8'-hydroxylase activity comprises a deletion of at least one part of an exon of the gene, resulting in the gene not encoding a protein with ABA 8'-hydroxylase activity. In certain embodiments, the deletion (which may include a non-coding region) is less than about 1,000, 500, or 300 base pairs in length.

In a further aspect, the present invention provides a method of introducing an allele of an ABA 8'-hydroxylase gene into a cereal plant lacking said allele, the method comprising;

i) crossing a first parent cereal plant with a second parent cereal plant, wherein the second plant comprises said allele of an ABA 8'-hydroxylase gene, and ii) backcrossing the progeny of the cross of step i) with plants of the same genotype as the first parent plant for a sufficient number of times to produce a plant with a majority of the genotype of the first parent but comprising said allele, wherein the allele confers upon seed of said plant an altered rate of germination, altered dormancy and/or an altered level of ABA 8'-hydroxylase activity, when compared to seed of the cereal plant lacking said allele, and wherein progeny plants are genotyped for the presence or absence of said allele using a method of the invention.

Preferably, the rate of germination is determined up to about 21 days after the beginning of imbibition, for example after 1, 2, 3, 5 or 7 days.

In an embodiment, the method further comprises analysing the plant for at least one other genetic marker. In a preferred embodiment, the other genetic marker is a further marker for grain dormancy.

In another aspect, the present invention provides a cereal plant, or progeny thereof, produced using a method of the invention. Also provided is a cereal plant, or progeny thereof, genotyped using a method of the invention.

Preferably, the plant is wheat or barley. In a further preferred embodiment, the plant is not rice.

In one embodiment, the plant is a wheat plant, and wherein the rate of germination of a seed of the plant is decreased relative to a wheat plant lacking said allele.

In a further aspect, the present invention provides a method of producing seed, the method comprising;

a) growing a plant of the invention, and b) harvesting the seed.

In another aspect the present invention provides seed of a plant of the invention. Preferably the seed is cereal grain such as is typically harvested at maturity. The grain may be dried to a preferred moisture content, for example less than about 18-20% moisture content.

Preferably, seeds of a plant of the invention are dormant at harvest. However, in certain circumstances it may be useful to produce a plant which has seeds that are non-dormant at harvest.

In a further aspect, the present invention provides a method of producing flour, wholemeal, starch or other product, for example bran, from the seed, the method comprising;

a) obtaining seed of the invention, and b) extracting the flour, wholemeal, starch or other product.

Also provided is a product produced from a seed of the invention and/or the plant of the invention. Such products can be food, for example food intended for consumption by mammals such as humans, livestock, or birds such as poultry, or non-food products. Methods of producing such products are well known to those skilled in the art.

Examples of food products include, but are not limited to, flour, starch, leavened or unleavened breads, pasta, noodles, animal fodder, breakfast cereals, snack foods, cakes, malt, beer, pastries and foods containing flour-based sauces.

In a preferred embodiment, the product is beer or malt.

Examples of non-food products include, but are not limited to, films, coatings, adhesives, building materials and packaging materials.

In another aspect, the present invention provides a method of preparing a food product of the invention, the method comprising mixing seed, or flour, wholemeal or starch from said seed, with another ingredient.

In a further aspect, the present invention provides a method of preparing malt, comprising the step of germinating seed of the invention.

In another aspect, the present invention provides a substantially purified antibody, or fragment thereof, that specifically binds a polypeptide of the invention.

In another aspect, the present invention provides an isolated oligonucleotide capable of being used in a method of the invention.

Preferably, the oligonucleotide is capable of being used as a primer for nucleic replication or reverse transcription.

Preferably, the oligonucleotide comprises a sequence nucleotides provided as any one of SEQ ID NO's 78 to 89, or a variant of any one thereof.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE
ACCOMPANYING DRAWINGS

FIG. 1. Catabolism of ABA through hydroxylation.

Figure 2:
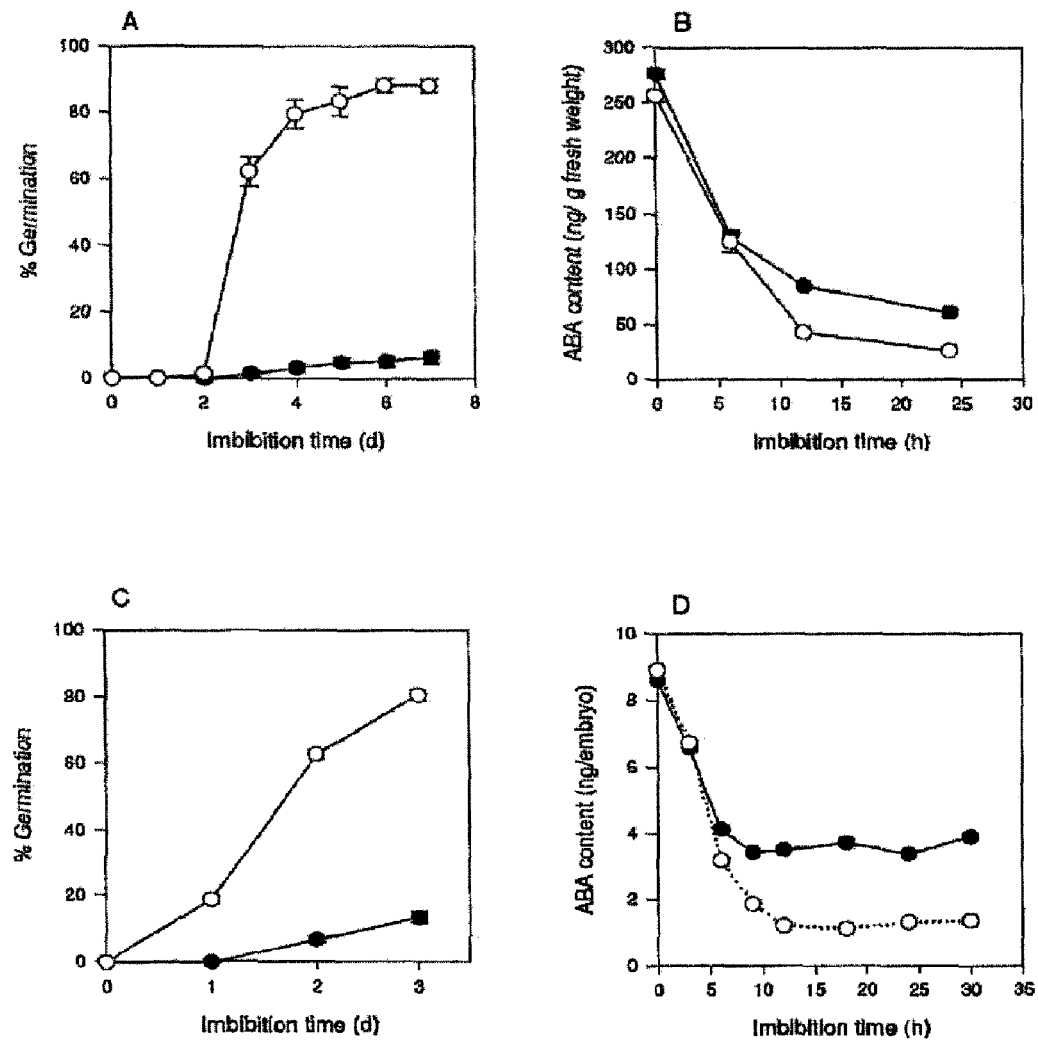

FIG. 2. The effect of after-ripening on germination and ABA levels in imbibing *Arabidopsis* seeds and barley grains.
 (A) Germination kinetics of after-ripened (ND, open circles) and dormant (D, filled circles) *Arabidopsis* C24 seeds. Data presented were averages of three replicates with error bars representing the standard error of the mean (SEM).
 (B) ABA levels in after ripened (ND, open circles) and dormant (filled circles) *Arabidopsis* C24 seeds. Data presented were averages of two replicates with error bars representing the SEM. Error bars were often smaller than the symbols.
 (C) Germination kinetics of after-ripened (ND, open circles) and dormant (filled circles) barley grains. Data presented were averages of three replicates with error bars representing the SEM. Error bars were often smaller than the symbols.
 (D) ABA levels in embryos from ND (open circles) and dormant (filled circles) barley cv. Proctor.

Figure 3:
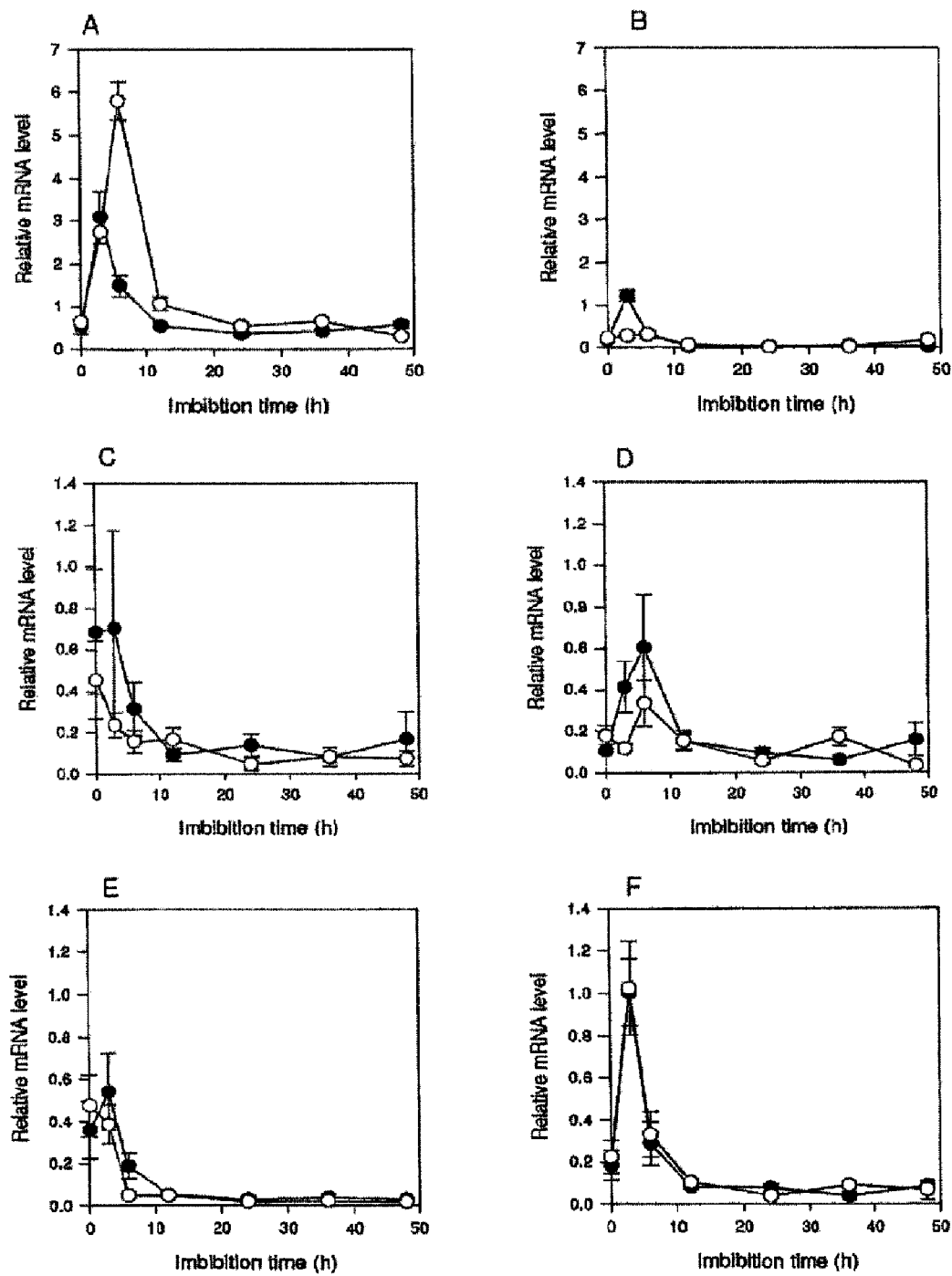

FIG. 3. Changes in the levels of gene expression during imbibition of ND (open circles) and D (filled circles) *Arabidopsis* (ecotype C24) seeds. Measurements shown are averages of three replicates, with error bars representing the SEM.
 (A) CYP707A2
 (B) CYP707A3
 (C) AtNCED2
 (D) AtNCED5
 (E) AtNCED6
 (F) AtNCED9.

Figure 4:
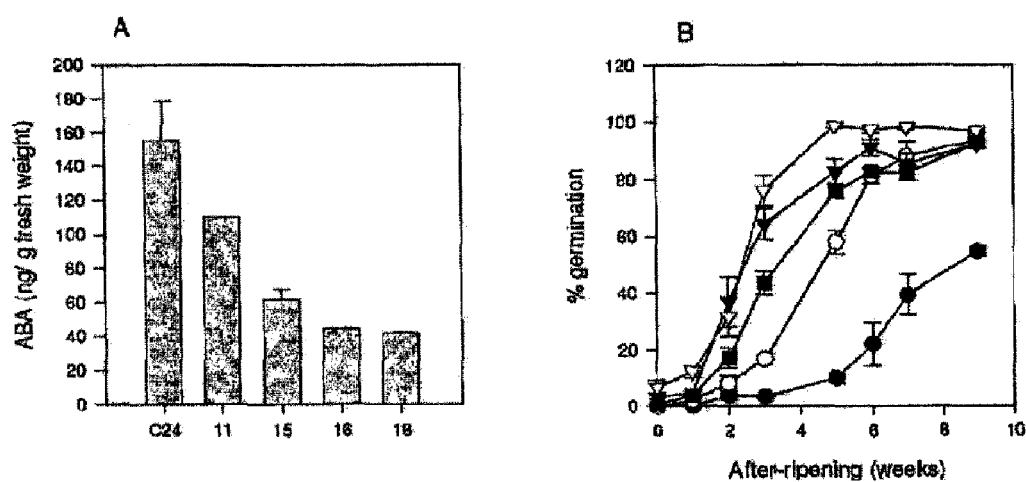

FIG. 4. ABA levels and responses to after-ripening in seeds from transgenic 35S-707A1 *Arabidopsis* plants.
 (A) Comparison of ABA levels in wild type (ecotype C24) and four independent 35S-707A1 lines (Nos. 11, 15, 16 and 18). Measurements represent the average of two replicates with error bars representing the SEM.
 (B) Dormancy decay curves for wild-type C24 (filled circles) and four independent 35S-707A1 lines, #11 (open circles), #15 (filled triangles), #16 (open triangles), #18 (filled squares). Seed from the same harvest was used both in the ABA determination and germination assays. Measurements represent the average of three replicates with error bars representing the SEM.

Figure 5:
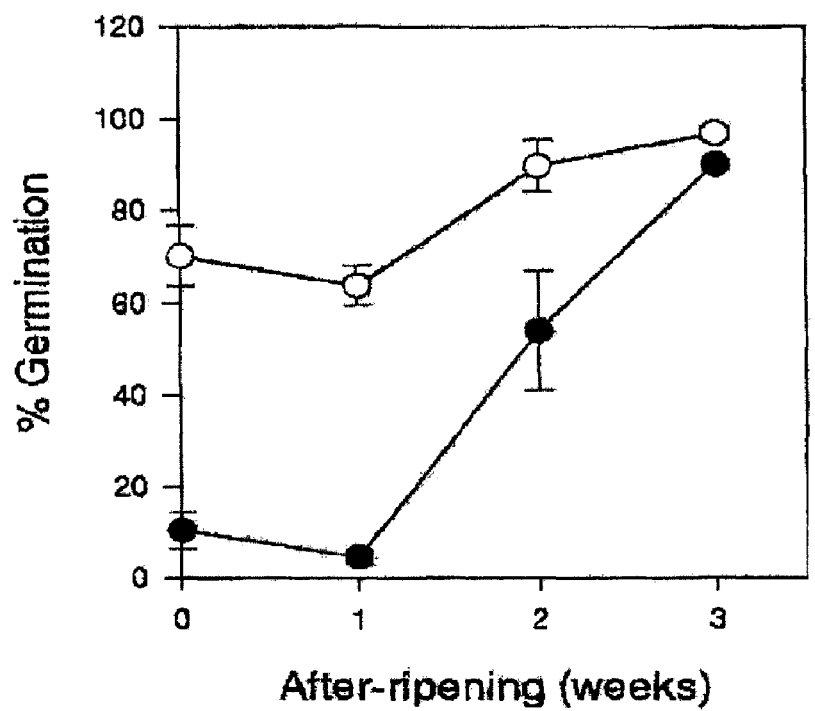

FIG. 5. Seeds of cyp707a2-1 require longer periods after ripening to break dormancy. Dormancy decay curves of wild type Columbia seeds (open circles) and cyp707a2-1 (filled circles) in the same ecotype background. Measurements represent the average of three replicates with error representing the SEM.

FIG. 6. Genomic sequence comprising the gene encoding a barley ABA hydroxylase (HvABA8'OH). The nucleotide positions for the promoter and 5'UTR are 1-853 and for exons and introns:
 Exon 1: 854-1387
 Intron 1: 1388-1503
 Exon 2: 1504-1887
 Intron 2: 1888-1985
 Exon 3: 1986-2154
 Intron 3: 2155-2375
 Exon 4: 2376-2481
 Intron 4: 2482-2600
 Exon 5: 2601-2810
 3' UTR sequences: 2811-3190.

Figure 7:
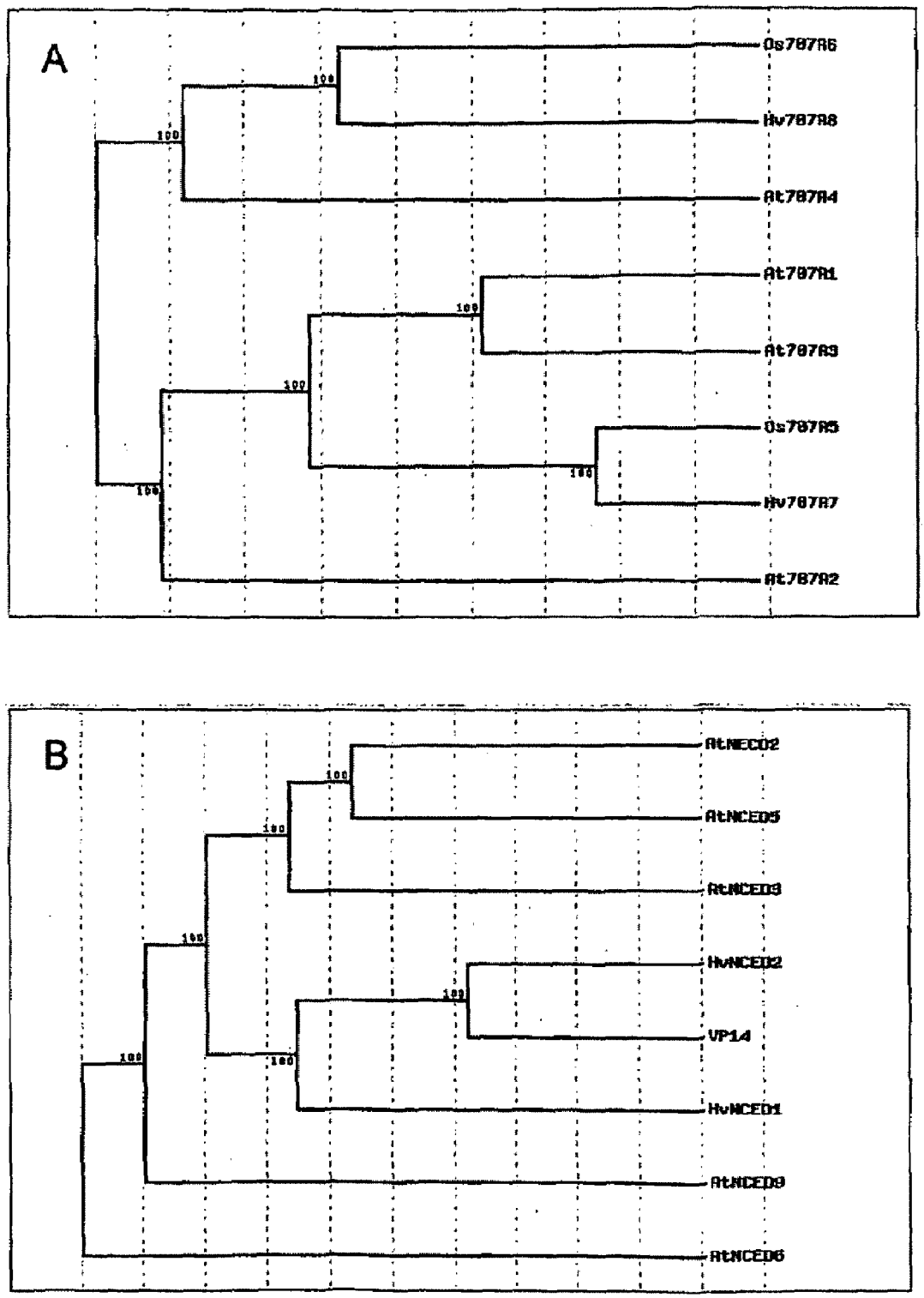

FIG. 7. CLUSTALW tree analysis of amino acid sequences of:
 (A) CYP707A proteins from barley [HvABA8'OH-1 and HvABA8'OH-2], rice [OsCYP707A5 (AP004129) and OsCYP707A6 (AP004162)] and *Arabidopsis* [AtCYP707A1 (At4g19230), AtCYP707A2 (At2g29090), AtCYP707A3 (At5g45340) and AtCYP707A4 (At3g19270).]
 (B) NCED proteins from barley [HvNCED1 and HvNCED2], maize [ZmVP14 (U95953)] and *Arabidopsis* [AtNCED2 (At4g18350), AtNCED3 (At3g14440), AtNCED5 (At1g30100) AtNCED6 (At3g24220) and AtNCED9 (At1g78390)].

Figure 8:
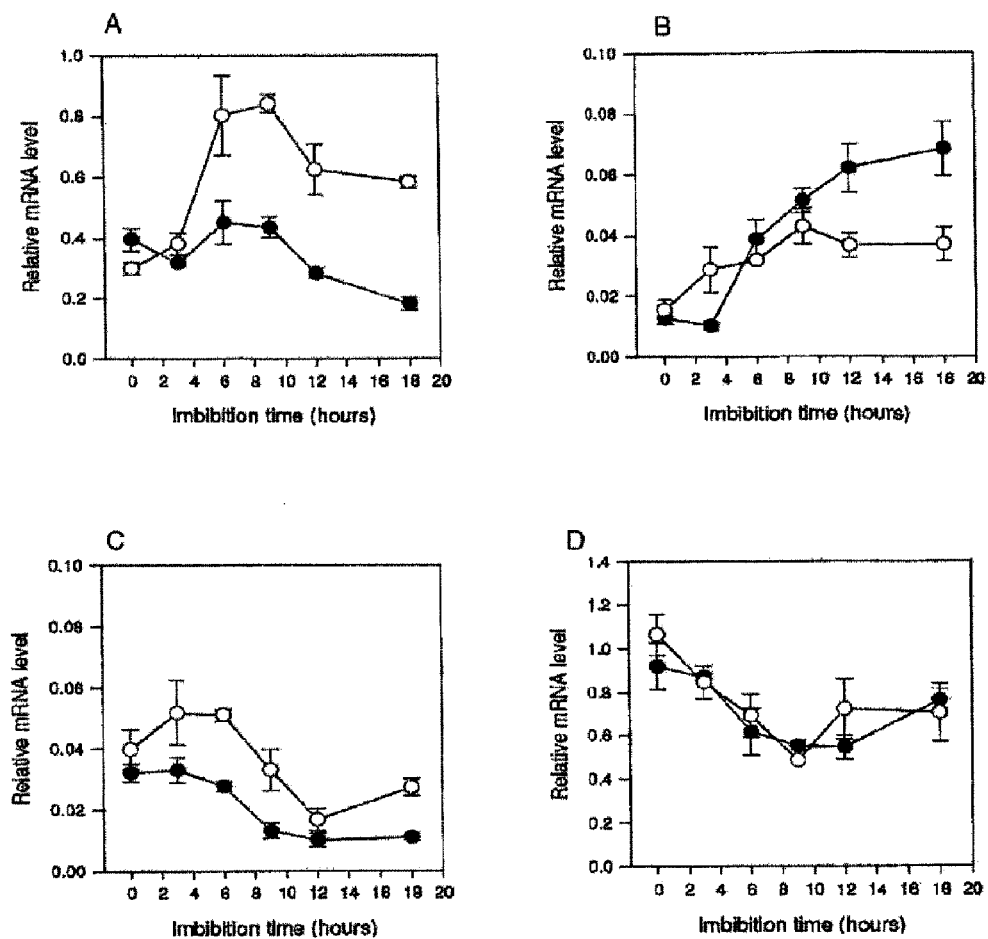

FIG. 8. Changes in the levels of gene expression in embryos from dry and imbibed ND (open circles) and D (filled circles) barley grains. All measurements shown are averages of three replicates, with error bars representing the SEM.
 (A) HvABA8'OH-1
 (B) HvNCED1
 (C) HvNCED2
 (D) HvVP1.

Figure 9:
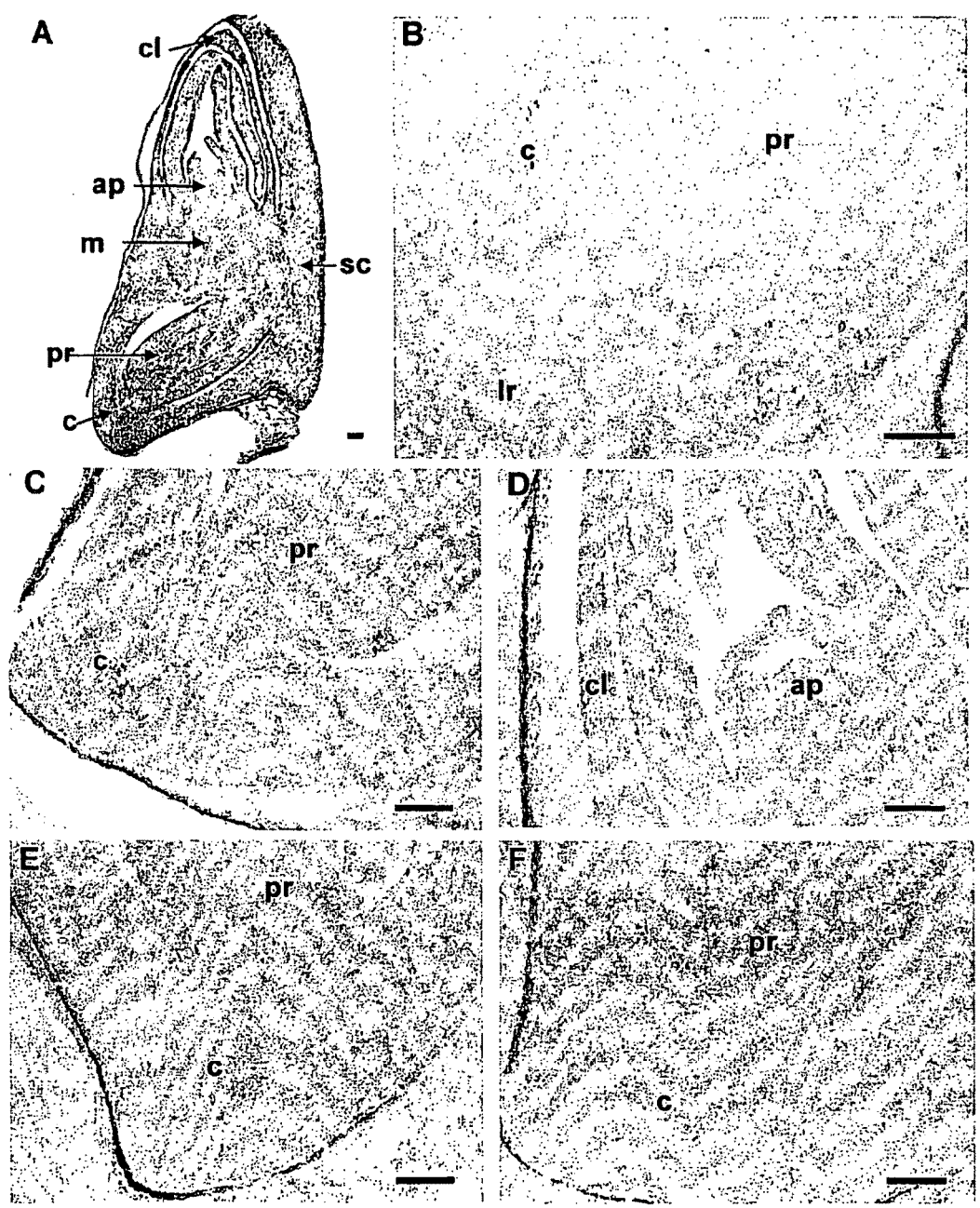

FIG. 9. Expression of HvABA8'OH-1 in barley embryos from dormant and non-dormant grains imbibed for 6 h. RNA in situ analysis of HvABA8'OH-1 expression in imbibed non-dormant (B-D, F) and dormant embryos (E). Sections were hybridized with antisense (B-E) and sense (F) HvABA8'OH-1 RNA probes labeled with digoxygenin-UTP.
 (A) Median longitudinal section of a 6 h-imbibed barley embryo stained with toluidine blue.
 (B) Transverse section through the root apex region showing coleorhiza tissue and the primary and lateral roots.

(C, E, F) Median longitudinal sections through root apex containing coleorhiza and primary root.

(D) Median longitudinal section through the shoot apex, coleoptile and leaves. ap, shoot apex c, coleorhiza; cl, coleoptile; lr, lateral root; m, mesocotyl; sc, scutellum; pr, primary root; Bars=0.1 mm.

Figure 10:
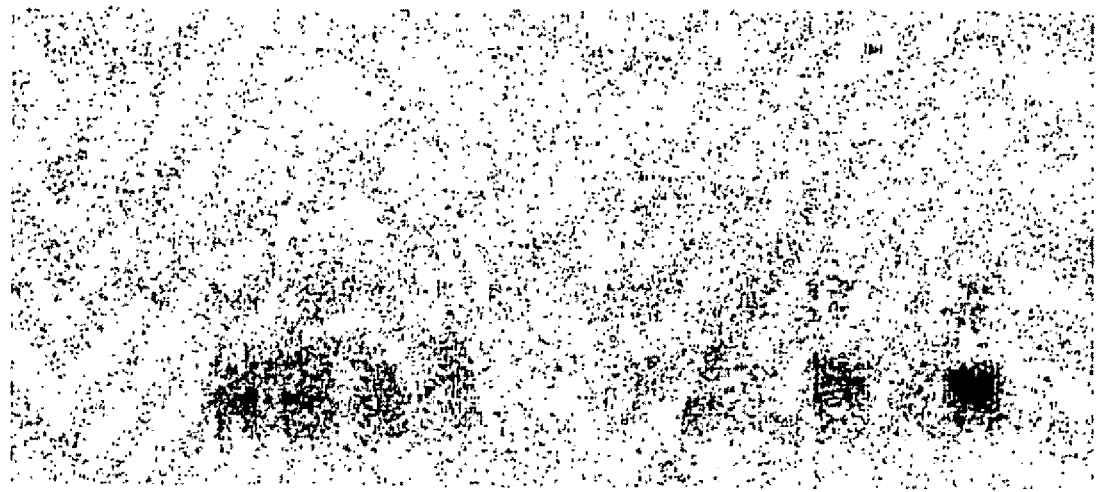

FIG. 10. Northern blot analysis detecting expression of a transgene encoding an inhibitory hairpin RNA in transgenic barley.

Figure 11:
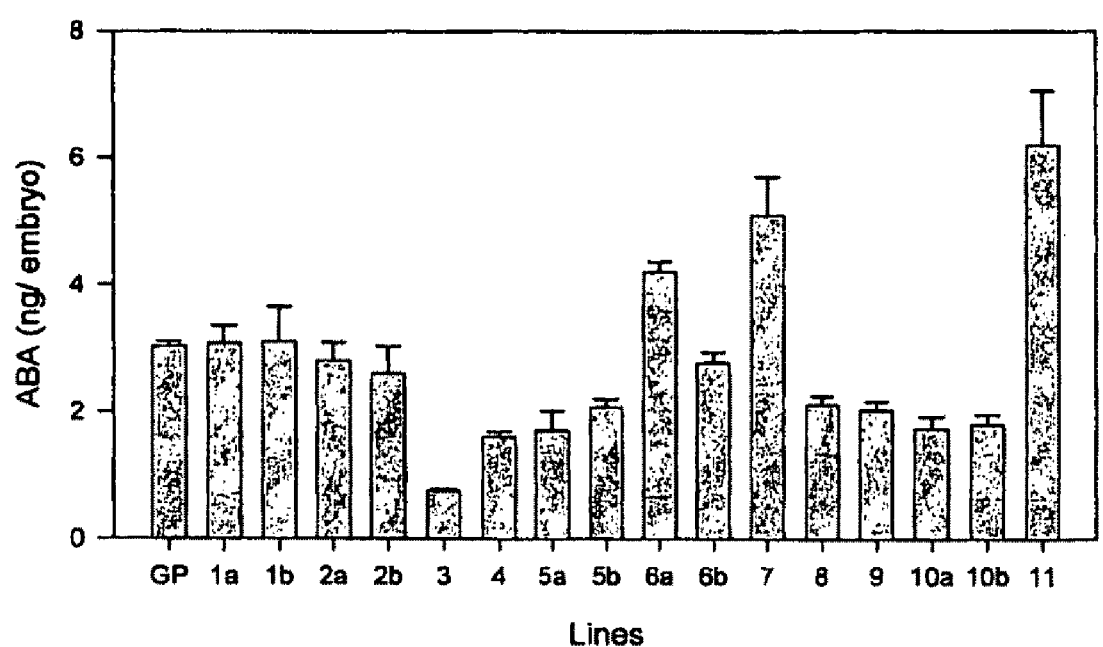

FIG. 11. ABA content of embryos of dry grains of Golden Promise (GP) and transgenic RNAiHvABA8'OH-1 T0 lines.

FIG. 12. Nucleotide sequence of TaABA8OH-1 gene D genome (cv Sunstate). Exon sequences are shown in bold. The protein coding region exons included nucleotides 22-576, 681-1065, 1145-1314, 1520-1626 and 1715-1941. The translation start ATG was at nucleotides 22-24 and the stop codon TGA at 1939-1941.

FIG. 13. Alignment of amplified wheat ABA 8' hydroxylase-1 genomic sequences.

Figure 14:
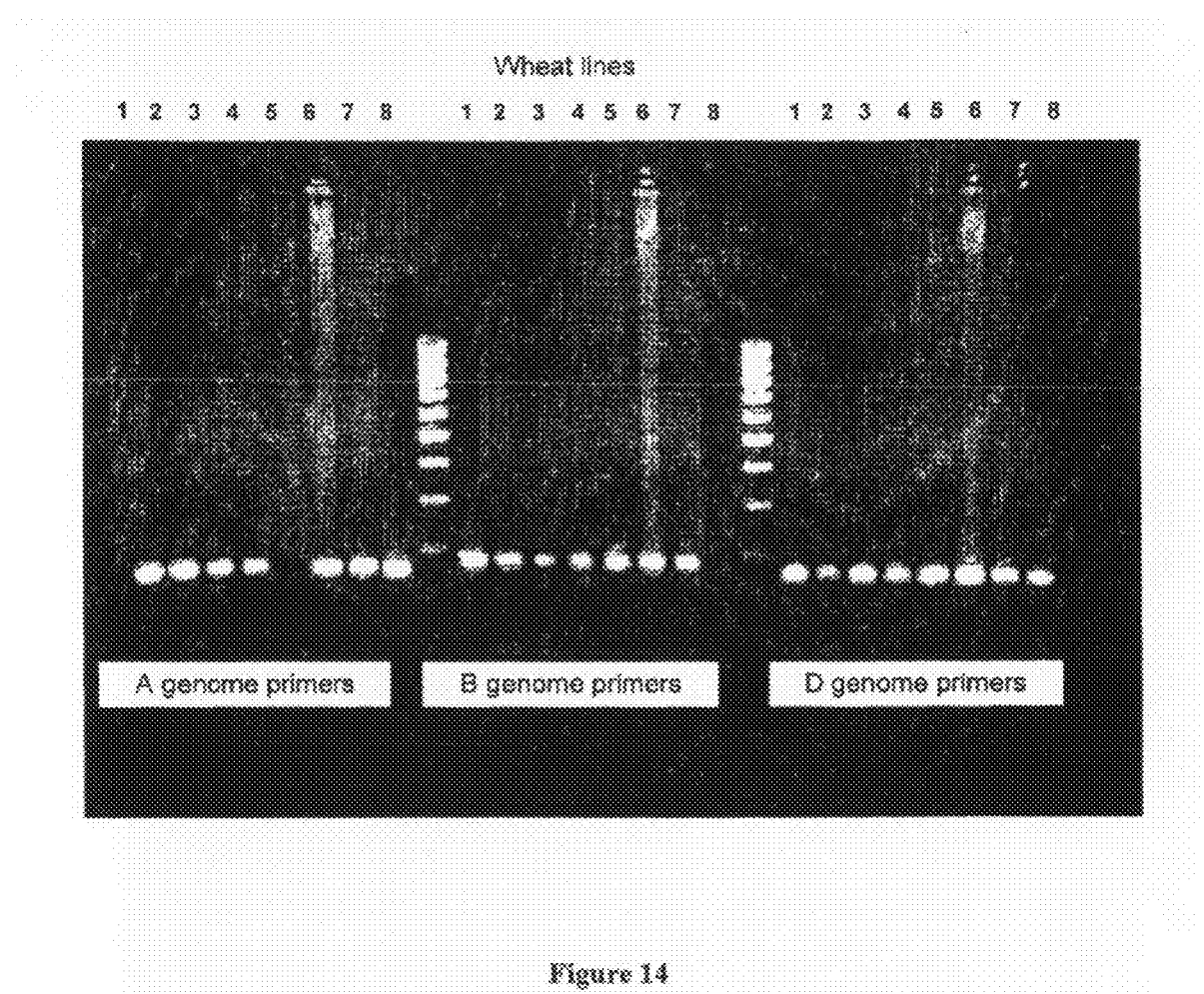

FIG. 14. PCR detection of wheat ABA8'OH-1 gene mutations.

Figure 15:
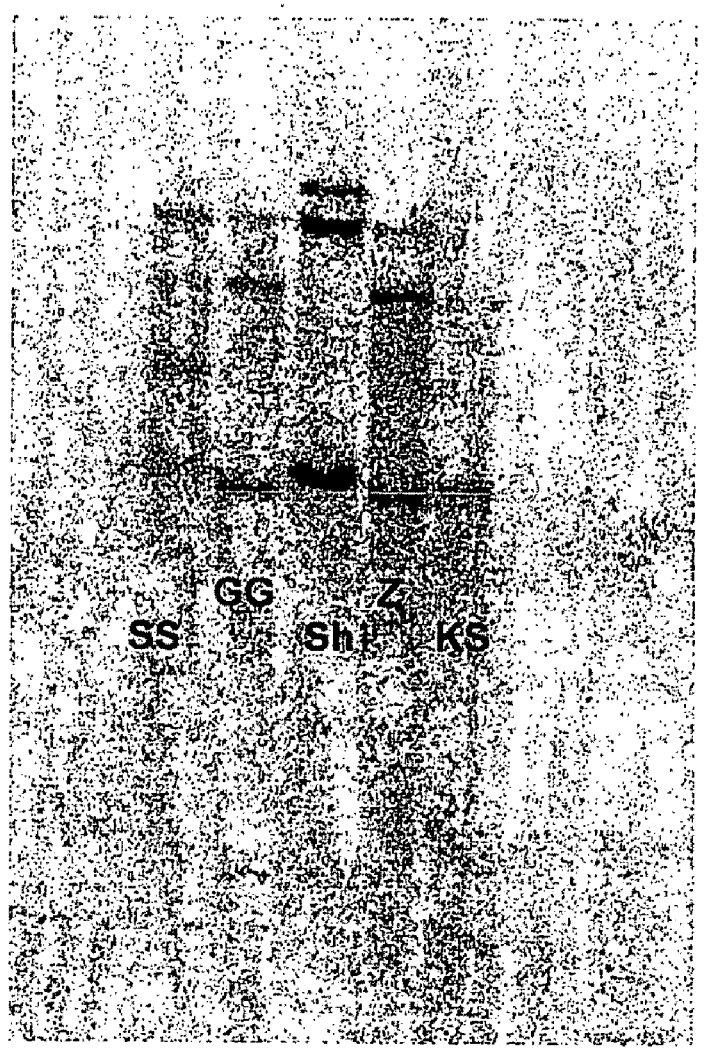

FIG. 15. Southern blot hybridization analysis of wheat ABA8'OH-1 mutants.

Figure 16:
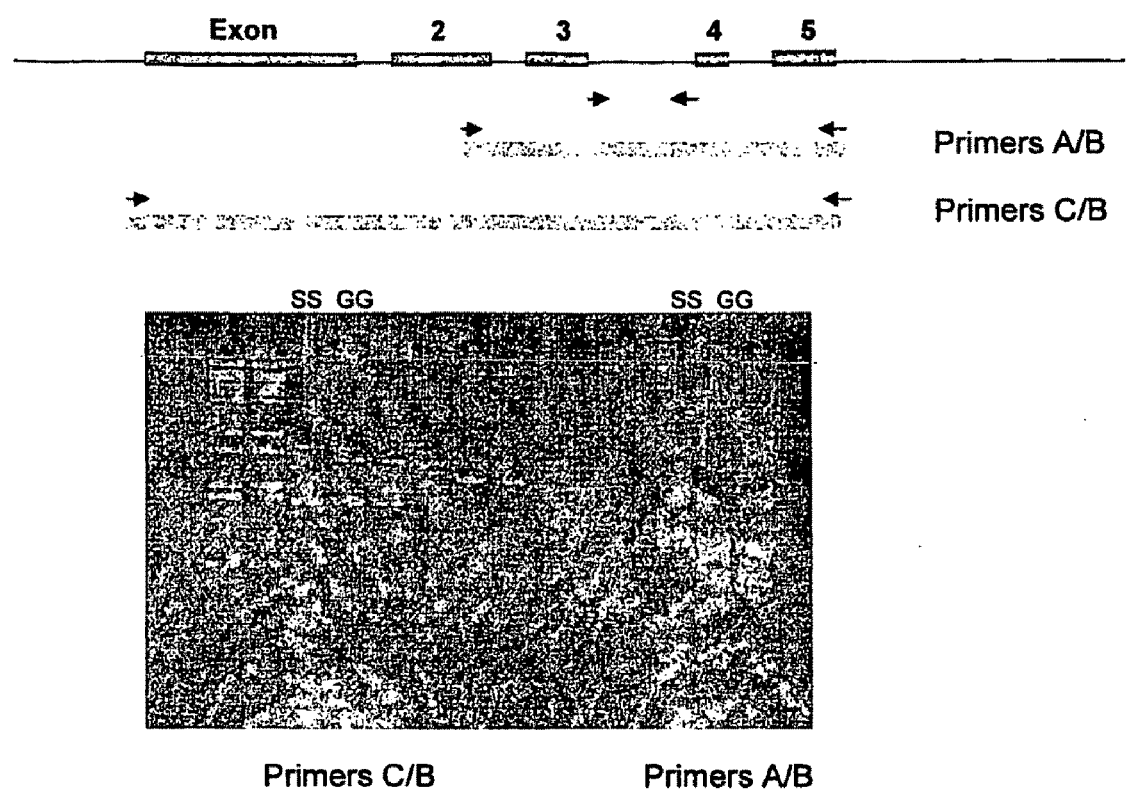

FIG. 16. PCR analysis of D genome deletion in the wheat ABA8'OH-1 gene.

FIG. 17. Germination profiles of (a) Sunstate grains, (b) grains from F2 Sunstate×Aus25138, (c) grains from F2 Sunstate×Aus26243, and (d) grains from F2 Sunstate×Aus14510. Treatments included pre-imbibition in 0-7 days in the cold and dark.

KEY TO THE SEQUENCE LISTING

SEQ ID NO:1—*Hordeum vulgare* ABA8'OH-1 genomic sequence.
SEQ ID NO:2—*Hordeum vulgare* ABA8'OH-1 cDNA sequence.
SEQ ID NO:3—Open reading frame of *Hordeum vulgare* ABA8'OH-1 cDNA.
SEQ ID NO:4—*Hordeum vulgare* ABA8'OH-1 protein.
SEQ ID NO:5—*Hordeum vulgare* ABA8'OH-2 cDNA sequence.
SEQ ID NO:6—Open reading frame of *Hordeum vulgare* ABA8'OH-2 cDNA.
SEQ ID NO:7—*Hordeum vulgare* ABA8'OH-2 protein.
SEQ ID NO:8—*Triticum aestivum* ABA8'OH-1 cDNA sequence.
SEQ ID NO:9—Open reading frame of *Triticum aestivum* ABA8'OH-1 cDNA.
SEQ ID NO:10—*Triticum aestivum* ABA8'OH-1 protein.
SEQ ID NO:11—*Triticum aestivum* ABA8'OH-1 gene D genome (cv Sunstate) sequence.
SEQ ID NO:12—Amplification product (designated fgt1871) from genomic DNA of *Triticum aestivum* cv Bob White 26.
SEQ ID NO:13—Amplification product (designated fgt1886) from genomic DNA of *Triticum aestivum* cv Bob White 26.
SEQ ID NO:14—Amplification product (designated fgt1880) from genomic DNA of *Triticum aestivum* cv Bob White 26.
SEQ ID NO:15—Amplification product (designated fgt1868) from genomic DNA of *Triticum aestivum* cv Bob White 26.
SEQ ID NO:16—Amplification product (designated fgt1882) from genomic DNA of *Triticum aestivum* cv Bob White 26.
SEQ ID NO:17—Amplification product (designated fgt1864) from genomic DNA of *Triticum aestivum* cv Bob White 26.
SEQ ID NO:18—Amplification product (designated fgt1865) from genomic DNA of *Triticum aestivum* cv Bob White 26.
SEQ ID NO:19—Amplification product (designated fgt1878) from genomic DNA of *Triticum aestivum* cv Bob White 26.
SEQ ID NO:20—Amplification product (designated fgt1876) from genomic DNA of *Triticum aestivum* cv Bob White 26.
SEQ ID NO:21—Amplification product (designated fgt1873) from genomic DNA of *Triticum aestivum* cv Bob White 26.
SEQ ID NO:22—Amplification product (designated fgt1870) from genomic DNA of *Triticum aestivum* cv Bob White 26.
SEQ ID NO's 23 to 89, 92 and 93—Oligonucleotide primers.
SEQ ID NO:90—Rice OsCYP707A5 coding sequence.
SEQ ID NO:91—Rice OsCYP707A6 coding sequence.
SEQ ID NO:94—HvABA8'OH-1 3' specific probe.

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, molecular genetics, cereal plant breeding—especially wheat and barley breeding, transgenic plants, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Selected Definitions

As used herein, a polypeptide with "ABA 8'-hydroxylase activity" (also referred to herein as "ABA 8'-OH activity") is able to hydroxylate (+)-abscisic acid (ABA) to produce 8'-hydroxyABA (see FIG. 1).

As used herein, an "ABA 8'-hydroxylase-1 gene" (also referred to herein as "ABA 8'OH-1 gene") refers to the most abundantly expressed gene encoding a polypeptide with ABA 8'-hydroxylase activity in the grain of a wheat or barley plant. Preferably, an "ABA 8'-hydroxylase-1 gene" of the invention encodes a polypeptide comprising amino acids having a sequence provided as SEQ ID NO: 4, SEQ ID NO:10 or a polypeptide having an amino acid sequence at least 90% identical to any one thereof. Examples of an "ABA 8'-hydroxylase-1 gene" are provided in FIGS. 6 and 12, whereas examples of variants of the gene provided in FIG. 12 are provided in FIG. 13. Such variants and homologs may be recognised on the basis of the homology to the wheat and barley ABA8'OH-1 genes described herein and their expression pattern in the plant organs. This term is used broadly herein to include a polynucleotide comprising the open reading frame of said gene (such as SEQ ID NO:3 and SEQ ID NO:9).

As used herein, "imbibition" refers to the process in which water is taken up by a seed at the beginning of germination. Imbibition of seeds such as cereal grain typically takes 6 or more hours at room temperature. Imbibition of seeds of non-cereals may take considerably longer. Germination ideally but not necessarily occurs in the continued presence of sufficient moisture, for example on moistened filter paper.

With regard to cereal plants, as used herein the term "germination" refers to the emergence of the coleorhiza from the seed coat after imbibition.

With regard to non-cereal plants, as used herein the term "germination" refers to the emergence of the root tip from the seed coat after imbibition.

The "rate of germination" of a seed refers to the percentage of seeds in a population which have germinated over a period of time, for example up to 21 days, or in the period 1 to 10 days, after the beginning of imbibition. A population of seeds can be assessed daily over several days to determine the germination percentage over time. Certain aspects of the invention relate to altering/modulating the rate of germination of a seed. This alteration/modulation may be transient during the life span of a seed. For example following harvest a seed of transgenic plant of the invention may have an altered rate of germination when compared to a seed of a corresponding non-transgenic plant upon harvest, however, following six months storage in a silo the seed of the same transgenic plant of the invention may have the same rate of germination when compared to a seed of a corresponding non-transgenic plant following six months storage in a silo, or vice versa. In other words, at some point in the life span of the seed it will have an altered rate of germination when compared to a suitable control (non-transgenic or wild type etc.) which has been exposed to the same conditions.

As used herein, the term "dormant" refers to the failure of the viable, intact seeds of a plant to germinate under specified favourable conditions, particularly in terms of temperature and in the presence of moisture. Dormancy is a quantitative trait. With regard to barley and wheat, seeds of a plant are considered dormant if less than 90% of viable, intact seeds germinate after 7 days at 20° C. following the beginning of imbibition. Viable seeds are those which are able to germinate after dormancy breaking, for example a substantial period (weeks or months) of storage at room temperature or heat treatment, well known in the art.

As used herein, the term "non-dormant" refers to the ability of the seeds of a plant to germinate under specified favourable conditions. With regard to barley and wheat, seeds of a plant are considered non-dormant if at least 90% of the viable, intact seeds germinate after 7 days at 20° C. following the beginning of imbibition.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. Tetraploid wheat includes *T. durum* (also referred to herein as durum wheat or *Triticum turgidum* ssp. *durum*), *T. dicoccoides, T. dicoccum, T. polonicum*, and interspecies cross thereof. In addition, the term "wheat" includes potential progenitors of hexaploid or tetraploid *Triticum* sp. such as *T. uartu, T. monococcum* or *F. boeoticum* for the A genome, *Aegilops speltoides* for the B genome, and *T. tauschii* (also known as *Aegilops squarrosa* or *Aegilops tauschii*) for the D genome. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to Triticale. Preferably, the wheat plant is suitable for commercial production of grain, such as commercial varieties of hexaploid wheat or durum wheat, having suitable agronomic characteristics which are known to those skilled in the art.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

As used herein, the term "linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). The term "genetically linked" as used herein is narrower, only used in relation to where a marker locus and a second locus being sufficiently close on a chromosome that they will be inherited together in more than 50% of meioses. Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart.

As used herein, the "other genetic markers" may be any molecules which are linked to a desired trait of a cereal plant such as wheat. Such markers are well known to those skilled in the art and include molecular markers linked to genes determining traits such disease resistance, yield, plant morphology, grain quality, other dormancy traits such as grain colour, gibberellic acid content in the seed, plant height, flour colour and the like. Examples of such genes are stem-rust resistance genes Sr2 or Sr38, the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance (Eagles et al., 2001; Langridge et al., 2001; Sharp et al., 2001). With specific regard to grain dormancy, other markers include the R gene for red grain colour (Himi et al., 2002), as well as markers described by Mares et al. (2005), Li et al. (2004), Kato et al. (2001), Mori et al. (2005) and Prada et al. (2004).

The term "plant" includes whole plants, vegetative structures (for example, leaves, stems), roots, floral organs/structures, seed (including embryo, endosperm, and seed coat), plant tissue (for example, vascular tissue, ground tissue, and the like), cells and progeny of the same.

A "transgenic plant" refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

As used herein, the term "corresponding non-transgenic plant" refers to a wild-type plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

The terms "seed" and "grain" are used interchangeably herein. "Grain" generally refers to mature, harvested grain but can also refer to grain after imbibition or germination, according to the context. Mature grain commonly has a moisture content of less than about 18-20%.

"Nucleic acid molecule" refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity defined herein.

As used herein, the term "nucleic acid amplification" refers to any in vitro method for increasing the number of copies of a nucleic acid molecule with the use of a DNA polymerase. Nucleic acid amplification results in the incorporation of nucleotides into a DNA molecule or primer thereby forming a new DNA molecule complementary to a DNA template. The newly formed DNA molecule can be used a template to synthesize additional DNA molecules.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, a polypeptide with "NCED activity" (also referred to as "9-cis epoxycartenoid dioxygenase activity") is able to cleave 9-cis xanthophyll to produce xanthoxin.

Polypeptides

By "substantially purified polypeptide" we mean a polypeptide that has generally been separated from the lipids, nucleic acids, other peptides, and other contaminating molecules with which it is associated in its native state. Preferably, the substantially purified polypeptide is at least 60% free, more preferably at least 75% free, and more preferably at least 90% free from other components with which it is naturally associated. As the skilled person will appreciate, a polypeptide produced by expression of a recombinant polynucleotide is a purified polypeptide.

The terms "polypeptide" and "protein" are generally used interchangeably. The terms "proteins" and "polypeptides" as used herein also include variants, mutants, modifications, analogous and/or derivatives of the polypeptides of the invention as described herein.

The % identity of a polypeptide can be determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids.

As used herein a "biologically active" fragment is a portion of a polypeptide of the invention which maintains a defined activity of the full-length polypeptide. In a particularly preferred embodiment, the biologically active fragment is able to hydroxylate ABA to produce 8'-hydroxyABA. Biologically active fragments can be any size as long as they maintain the defined activity.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics.

Mutant (altered) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the E. coli XL-1 red (Stratagene) and propagating the transformed bacteria for a suitable number of generations. In another example, the polynucleotides of the invention are subjected to DNA shuffling techniques as broadly described by Harayama (1998). These DNA shuffling techniques may include genes related to those of the present invention, such as ABA8'OH genes from plant species other than wheat or barley, and/or include different genes from the same plant encoding similar proteins (such as the barley ABA8'OH-1 and ABA8'OH-2 genes). Products derived from mutated/altered DNA can readily be screened using techniques described herein to determine if they possess, for example, ABA 8'-hydroxylase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino bexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

TABLE 1

Exemplary substitutions

| Original Residue | Exemplary Substitutions |
| --- | --- |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid". As the skilled person will appreciate, a recombinant polynucleotide is an isolated polynucleotide, even in circumstances where the recombinant (exogenous) polynucleotide is in a cell which may or may not also naturally comprise and/or express a corresponding native polynucleotide.

The % identity of a polynucleotide can be determined by GAP (Needleman and Wunsch, 1970) analysis (GCG program) with a gap creation penalty-5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Preferably, a polynucleotide of the invention which encodes a polypeptide with ABA 8'-hydroxylase activity is greater than 400, more preferably greater than 500, more preferably greater than 600, more preferably greater than 700, more preferably greater than 800, more preferably greater than 900, and even more preferably greater than 1,000 nucleotides in length.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Oligonucleotides and/or nucleic acids of the invention hybridize to a cereal plant ABA8'OH gene, or a region of the genome of said plant genetically linked thereto, under stringent conditions. The term "stringent hybridization conditions" and the like as used herein refers to parameters with which the art is familiar, including the variation of the hybridization temperature with length of an oligonucleotide. Nucleic acid hybridization parameters may be found in references which compile such methods, Sambrook, et al. (supra), and Ausubel, et al. (supra). For example, stringent hybridization conditions, as used herein, can refer to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA). Alternatively, the nucleic acid and/or oligonucleotides (which may also be referred to as "primers" or "probes") hybridize to the region of the wheat plant genome of interest under conditions used in nucleic acid amplification techniques such as PCR.

Oligonucleotides of the present invention can be RNA, DNA, or derivatives of either. Although the terms polynucleotide and oligonucleotide have overlapping meaning, oligonucleotide are typically relatively short single stranded molecules. The minimum size of such oligonucleotides is the size required for the formation of a stable hybrid between an oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Usually, monomers of a polynucleotide or oligonucleotide are linked by phosphodiester bonds or analogs thereof to form oligonucleotides ranging in size from a relatively short monomeric units, e.g., 12-18, to several hundreds of monomeric units. Analogs of phosphodiester linkages include: phosphorothioate, phosphorodithioate, phosphoroselenoate, phosphorodiselenoate, phosphoroanilothioate, phosphoranilidate, phosphoramidate.

The present invention includes oligonucleotides that can be used as, for example, probes to identify nucleic acid molecules, or primers to produce nucleic acid molecules. Oligonucleotide of the present invention used as a probe are typically conjugated with a detectable label such as a radioisotope, an enzyme, biotin, a fluorescent molecule or a chemiluminescent molecule.

Oligonucleotides of the invention are useful in methods of detecting an allele of an ABA8'OH gene linked to a dormancy trait of interest. Such methods, for example, employ nucleic acid hybridization and in many instances include oligonucleotide primer extension by a suitable polymerase (as used in PCR).

A variant of an oligonucleotide of the invention includes molecules of varying sizes of, and/or are capable of hybridising, for example, to the wheat genome close to that of, the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise the target region. In addition, variants may readily be designed which hybridise close (for example, but not limited to, within 50 nucleotides) to the region of the plant genome where the specific oligonucleotides defined herein hybridise.

Antisense Polynucleotides

The term "antisense polynucletoide" shall be taken to mean a DNA or RNA, or combination thereof, molecule that is complementary to at least a portion of a specific mRNA molecule encoding a polypeptide of the invention and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque (1995) and Senior (1998). Bourque (1995) lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior (1998) states that antisense methods are now a very well established technique for manipulating gene expression.

As used herein, the term "an antisense polynucleotide which hybridises under physiological conditions" means that the polynucleotide (which is fully or partially single stranded) is at least capable of forming a double stranded polynucleotide with mRNA encoding a protein, such as those provided in SEQ ID NO:2, SEQ ID NO:5 or SEQ ID NO:8, under normal conditions in a cell.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988, Perriman et al., 1992) and the hairpin ribozyme (Shippy et al., 1999).

The ribozymes of this invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. Accordingly, also provided by this invention is a nucleic acid molecule, i.e., DNA or cDNA, coding for a catalytic polynucleotide of the invention. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, catalytic polynucleotides of the invention should also be capable of hybridizing a target nucleic acid molecule (for example an mRNA encoding a polypeptide provided as SEQ ID NO:2, SEQ ID NO:5 or SEQ ID NO:6) under "physiological conditions", namely those conditions within a cell (especially conditions in a plant cell such as a wheat or barley cell).

RNA Interference

RNA interference (RNAi) is particularly useful for specifically inhibiting the production of a particular protein. Although not wishing to be limited by theory, Waterhouse et al. (1998) have provided a model for the mechanism by which dsRNA can be used to reduce protein production. This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the plant (preferably wheat or barley) in which it is to be introduced, e.g., as determined by standard BLAST search.

Examples of dsRNA molecules that may be used to down-regulate the production of a polypeptide with ABA 8'-hydroxylase activity are provided in Examples 7 and 10.

microRNA

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al., 2005; Almeida and Allshire, 2005).

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

Nucleic Acid Constructs, Vectors and Host Cells

The present invention includes the production of various transgenic plants. These include, but are not limited to, i) plants that express a polynucleotide of the invention which encodes a polypeptide having ABA 8'-hydroxylase activity, ii) plants where the expression level of at least one endogenous ABA 8'-hydroxylase gene has been increased relative to a corresponding non-transgenic plant, and iii) plants that express a polynucleotide which, when present in a cell of a cereal plant, down-regulates the level of ABA 8'-hydroxylase activity in the cell when compared to a cell that lacks said polynucleotide.

Nucleic acid constructs useful for producing the above-mentioned transgenic plants can readily be produced using standard techniques.

When inserting a region encoding an mRNA the construct may comprise intron sequences. These intron sequences may aid expression of the transgene in the plant. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not. However, in a preferred embodiment, any polypeptide encoding region is provided as a single open reading frame. As the skilled addressee would be aware, such open reading frames can be obtained by reverse transcribing mRNA encoding the polypeptide.

To ensure appropriate expression of the gene encoding an mRNA of interest, the nucleic acid construct typically comprises one or more regulatory elements such as promoters, enhancers, as well as transcription termination or polyadenylation sequences. Such elements are well known in the art.

The transcriptional initiation region comprising the regulatory element(s) may provide for regulated or constitutive expression in the plant. Preferably, expression at least occurs in cells of the seed. More preferably, expression at least occurs in the coleorhiza of the seed following imbibition. The regulatory elements may be selected from, for example, seed-specific promoters, or promoters not specific for seed cells (such as ubiquitin promoter or CaMV35S or enhanced 35S promoters).

Examples of seed specific promoters useful for the present invention include, but are not limited to, the wheat low molecular weight glutenin promoter (Colot et al., 1987), the promoter expressing α-amylase in wheat seeds (Stefanov et al., 1991), and the hordein promoter (Brandt et al., 1985), as well as the native promoter of a ABA8'OH gene.

The promoter may be modulated by factors such as temperature, light or stress. Ordinarily, the regulatory elements will be provided 5' of the genetic sequence to be expressed. The construct may also contain other elements that enhance transcription such as the nos 3' or the ocs 3' polyadenylation regions or transcription terminators.

Typically, the nucleic acid construct comprises a selectable marker. Selectable markers aid in the identification and screening of plants or cells that have been transformed with the exogenous nucleic acid molecule. The selectable marker gene may provide antibiotic or herbicide resistance to the wheat cells, or allow the utilization of substrates such as mannose. The selectable marker preferably confers hygromycin resistance to the wheat cells.

Preferably, the nucleic acid construct is stably incorporated into the genome of the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, more preferably barley or wheat cells, and even more preferably a wheat cell.

Transgenic Plants

General

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, sorghum, soybean millet, cassava, barley, or pea), or legumes. The plants may be grown for production of edible roots, tubers, leaves, stems, flowers or fruit.

Preferably, the transgenic plant is a cereal plant. Examples of cereal plants include, but are not limited to, wheat, barley, sorghum oats, and rye. More preferably, the cereal plant is wheat or barley. In a further preferred embodiment, the cereal plant is not rice.

Transgenic plants, as defined in the context of the present invention include plants and their progeny which have been genetically modified using recombinant techniques. This would generally be to modulate the production of at least one polypeptide defined herein in the desired plant or plant organ. Transgenic plant parts include all parts and cells of said plants such as, for example, cultured tissues, callus and protoplasts. Transformed plants contain genetic material that they did not contain prior to the transformation. The genetic material is preferably stably integrated into the genome of the plant. The introduced genetic material may comprise sequences that naturally occur in the same species but in a rearranged order or in a different arrangement of elements, for example an antisense sequence. Such plants are included herein as "transgenic plants". A "non-transgenic plant" is one which has not been genetically modified with the introduction of genetic material by recombinant DNA techniques. In a preferred embodiment, the transgenic plants are homozygous for each and every gene that has been introduced (transgene) so that their progeny do not segregate for the desired phenotype.

Several techniques exist for introducing foreign genetic material into a plant cell. Such techniques include acceleration of genetic material coated onto microparticles directly into cells (see, for example, U.S. Pat. Nos. 4,945,050 and 5,141,131). Plants may be transformed using *Agrobacterium* technology (see, for example, U.S. Pat. Nos. 5,177,010, 5,104,310, 5,004,863, 5,159,135). Electroporation technology has also been used to transform plants (see, for example, WO 87/06614, U.S. Pat. Nos. 5,472,869, 5,384,253, WO 92/09696 and WO 93/21335). In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during development and/or differentiation using appropriate techniques described herein.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors can also contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Any of several methods may be employed to determine the presence of a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers that will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed may also be identified i.e. distinguished from non-transformed or wild-type plants by their phenotype, for example conferred by the presence of a selectable marker gene, or conferred by the phenotype of a desired seed dormancy.

Transformation Methods for Cereal Plants

Methods for transformation of cereal plants such as wheat and barley for introducing genetic variation into the plant by introduction of an exogenous nucleic acid and for regeneration of plants from protoplasts or immature plant embryos are well known in the art, see for example, Wan and Lemaux (1994), Tingay et al., (1997), Canadian Patent Application No. 2,092,588, Australian Patent Application No 61781/94, Australian Patent No 667939, U.S. Pat. No. 6,100,447, International Patent Application PCT/US97/10621, U.S. Pat. Nos. 5,589,617, 6,541,257, and other methods are set out in Patent specification WO99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts.

The regenerable wheat cells are preferably from the scutellum of immature embryos, mature embryos, callus derived from these, or the meristematic tissue.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for farther backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis of at least one ABA 8'-hydroxylase gene, allows rapid selection of plants carrying the desired trait, which may be nurtured to maturity in the greenhouse or field for subsequent further backcrossing to the recurrent parent.

Any molecular biological technique known in the art which is capable of detecting alleles of an ABA 8'-hydroxylase can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of (for example) an ABA 8'-hydroxylase gene which confers to the seeds an altered rate of germination and/or modified levels of ABA 8'-hydroxylase activity. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., (2001).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). PCR can be performed on cDNA obtained from reverse transcribing mRNA isolated from plant cells expressing an ABA 8'-hydroxylase gene. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook et al. (supra). Sequencing can be carried out by any suitable method, for example, dideoxy sequencing, chemical sequencing or variations thereof. Direct sequencing has the advantage of determining variation in any base pair of a particular sequence.

Hybridization based detection systems include, but are not limited to, the TaqMan assay and molecular beacons. The TaqMan assay (U.S. Pat. No. 5,962,233) uses allele specific (ASO) probes with a donor dye on one end and an acceptor dye on the other end such that the dye pair interact via fluorescence resonance energy transfer (FRET). A target sequence is amplified by PCR modified to include the addition of the labeled ASO probe. The PCR conditions are adjusted so that a single nucleotide difference will effect binding of the probe. Due to the 5' nuclease activity of the Taq polymerase enzyme, a perfectly complementary probe is cleaved during PCR while a probe with a single mismatched base is not cleaved. Cleavage of the probe dissociates the donor dye from the quenching acceptor dye, greatly increasing the donor fluorescence.

An alternative to the TaqMan assay is the molecular beacon assay (U.S. Pat. No. 5,925,517). In the molecular beacon assay, the ASO probes contain complementary sequences flanking the target specific species so that a hairpin structure is formed. The loop of the hairpin is complimentary to the target sequence while each arm of the hairpin contains either donor or acceptor dyes. When not hybridized to a donor sequence, the hairpin structure brings the donor and acceptor dye close together thereby extinguishing the donor fluorescence. When hybridized to the specific target sequence, however, the donor and acceptor dyes are separated with an increase in fluorescence of up to 900 fold. Molecular beacons can be used in conjunction with amplification of the target sequence by PCR and provide a method for real time detection of the presence of target sequences or can be used after amplification.

Antibodies

The invention also provides monoclonal or polyclonal antibodies to polypeptides of the invention or fragments thereof. Thus, the present invention further provides a process for the production of monoclonal or polyclonal antibodies to polypeptides of the invention.

The term "binds specifically" refers to the ability of the antibody to bind to a polypeptide of the present invention but not other known ABA 8'-hydroxylases such as those from *Arabidopsis* (Kushiro et al., 2004) or rice. It is preferred that an antibody of the invention does not bind other polypeptides found in a plant cell producing the polypeptide (with the exception of related polypeptides that have ABA 8'-hydroxylase activity).

As used herein, the term "epitope" refers to a region of a polypeptide of the invention which is bound by the antibody. An epitope can be administered to an animal to generate antibodies against the epitope, however, antibodies of the present invention preferably specifically bind the epitope region in the context of the entire polypeptide.

If polyclonal antibodies are desired, a selected mammal (e.g., mouse, rabbit, goat, horse, etc.) is immunised with an immunogenic polypeptide such as that provided as SEQ ID NO:4, SEQ ID NO:7 or SEQ ID NO:10. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides peptides of the invention or fragments thereof haptenised to another peptide for use as immunogens in animals.

Monoclonal antibodies directed against polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Antibodies of the invention may be bound to a solid support and/or packaged into kits in a suitable container along with suitable reagents, controls, instructions and the like.

Preferably, antibodies of the present invention are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, e.g., biotin. Such labeled antibodies can be used in techniques known in the art to detect polypeptides of the invention.

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirms the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

EXAMPLES

Example 1

Materials and Methods

Plant Material

For the generation of dormant *Arabidopsis* seed, 6-10 plants of ecotype C24 plants were grown per 11 cm pot in soil (46% vermiculite, 35% klassman peat, 18.6% horticultural perlite). Plants were grown in a cabinet set at a 16 h photoperiod, a light intensity of 180 µmol·m$^{-2}$s$^{-1}$, and a temperature of 17.5° C., conditions found to be effective in generating high dormancy levels. Freshly mature seed was harvested in bulk 35 days after the petals appeared on the first flowers of plants in the pot. Harvested seed was then allowed to dry out at room temperature for 2 days. Half of this seed was stored at room temperature and dormancy decay was measured until 90-95% of the seed germinated after 7 days (3-4 months). The other half of the seed was stored at −80° C. in screw cap Eppendorf tubes and even after one year of storage, dormancy was maintained in this seed. After cold stratifying the seed by storage at 4° C. in a cold room for 7 days, which breaks dormancy in seeds of C24, the viability of the seed was tested and found to be greater than 95%.

*Hordeum vulgare* cv Proctor plants were grown in a naturally lit Phytotron glasshouse with the air temperature controlled at 17° C./9° C. day/night (Jacobsen et al., 2002). The seeds were sown in early May and grains were harvested at maturity in late December, threshed by hand and dried for 3 days in the laboratory. Subsequently, half of the Proctor barley was stored at −80° C. to retain dormancy and the rest were after-ripened at 37° C. Once dormancy had decayed grains were stored at room temperature.

Germination Assays

Germination assays were used to monitor dormancy decay. For *Arabidopsis*, approximately 100 seeds were placed in an 85 mm diameter Petri dish with 4 mL of sterile distilled water and four Whatman No. 1 filter papers (70 mm Diameter) and sealed with Parafilm (American National Can, Menasha, Wis.). Plates were then placed in a 20° C. growth room under continuous light at 100 µmol $m^{-2}s^{-1}$ for 7 days at which time germination was assessed. Experiments were done in triplicate for each line examined. Experiments were repeated each week until dormancy had decayed.

Barley germination assays were also performed under continuous light as described by Jacobsen et al. (2002). Sixty grains were placed in 85 mm Petri dishes containing 2 Whatman No. 1 filter papers (70 mm Diameter) and 4.2 ml of water. The dishes were sealed with Parafilm and incubated as described above for 3 days.

Endogenous ABA Measurements

To quantify the endogenous level of ABA in dry and imbibed *Arabidopsis* seed, 200 mg of seeds were sprinkled in 15 cm Petri dishes containing four Whatman No. 1 filter papers (125 mm Diameter) and 12.75 mL of sterile distilled water. After different periods of imbibition, seeds were harvested, frozen in liquid nitrogen and ground to a powder in a mortar and pestle. Samples were transferred to 10 mL of 80% methanol (HPLC grade) and long of [$^2H_4$] ABA (Dr Suzanne Abrams, National Research Council of Canada, Saskatoon, Canada) was added as an internal standard. After extraction at 4° C. overnight, methanol was removed by evaporation in a sample concentrator. Samples were then purified by Sep-Pak C18 cartridges and HPLC (Waters Associates, Milford, USA), as described previously for other hormones (Jager et al., 2005). Fractions containing ABA were grouped and dried under vacuum, taken up in 200 µL of methanol and methylated with 750 µL of ethereal diazomethane and dried under a stream of nitrogen. Each sample was then analysed by gas chromatography—select ion monitoring (GC-SIM) as the methyl ester on a Hewlett Packard 5890 gas chromatograph linked via an open spilt interface to a Kratos Concept ISQ mass spectrometer (Symons et al. 2002).

Dormant and non-dormant barley grains were imbibed as described above. For different periods, embryos were dissected and frozen immediately in liquid nitrogen and stored at −80° C. before ABA analysis. ABA was extracted from the isolated embryos and quantified by GC-MS-SIM as previously described (Jacobsen et al., 2002).

Functional ABA 8'OH Activity Assay Using Transgenic Yeast cDNAs corresponding to the *Arabidopsis* CYP707A1 and barley HvABA8'OH-1 were subcloned into the vector pYEDP60 (Pompon et al., 1996) and were transformed into the WAT11 and WAT21 strains by using a LiCl method, and selected on SGI minimal-media plates (6.7 g/liter yeast-nitrogen base without amino acids, 20 g/liter glucose, 10 g/liter Bacto casamino acids, 20 mg/liter tryptophan, and 20 g/liter agar) (Helliwell et al., 2001). Microsomes from yeast were prepared using the glass-bead method outlined in Pompon et al., (1996) and ABA8'OH activity measured by incubating approximately 5-10 mg of microsomal protein in 2 mL of 100 mM Tris-HCl pH 7.5, 0.5 mM NADPH, 0.5 mM FAD and 40 µM ABA (Sigma, St. Louis, Mo., (+/−)-cis, trans-abscisic acid) at 30° C. for 6 h. ABA and its metabolites were then extracted by rotating the yeast in 10 mL of 80% methanol overnight at 4° C. The methanol solution was dried down under vacuum in a Speedivac until 1-2 mL of aqueous solution remained. The pH was adjusted to 2.75-3.0 and the solution partitioned against 10 mL of ethyl acetate three times.

The pooled ethyl acetate fractions were dried to completion and then the hormones were methylated and analysed by gas chromatography-mass spectrometry (GC-MS) as previously described (Jacobsen et al. 2002). To confirm formation of a phaseic acid (PA) product, methylated extracts were each analysed by GC-MS co-injected with a parafilm standard to allow Kovats retention index (KRI) calculation. Correct retention time and ion ratios (based on relative peak heights) were compared to an authentic PA standard (gift from Dr Bryan Loveys, CSIRO, Urrbrae, Australia).

ABA Analyses by ELISA Assay

Embryos were isolated from dry grains and stored at −80° C. prior to analysis. ABA was extracted by homogenizing the embryos in 80% methanol in microfuge tubes and rotating the tubes overnight at 4° C. The homogenate was centrifuged at 5000 rpm for 5 min to pellet plant cell debris. The supernatant was removed and stored at −20° C., and the overnight extraction was repeated on the pellet with 80% methanol and the supernatants combined. The pellet was washed briefly two more times and the supernatants combined. The combined supernatants were dried down under vacuum until 50 µl liquid remained. The remaining liquid was made up to a total of 1 ml in TBS (Tris buffered-saline, pH7.5).

ABA measurements were performed using an enzyme immunoassay kit (Phytodetek, catalog number PDK 09347/ 0096) according to the manufacturer's instructions (Agdia, Indiana, USA).

ABA measurements can be performed using other methods known in the art such as through the use of GMSC.

Isolation of Wheat DNA

High quality genomic DNA was isolated from young hexaploid wheat plants for use in library construction as follows. Approximately 1 g of leaf tissue was ground up in liquid nitrogen using a mortar and pestle and then mixed with 4 ml DNA extraction buffer (1% Sarkosyl, 100 mM Tris-HCl pH 8.5, 100 mM NaCl, 10 mM EDTA and 2% PVP) and 4 ml phenol/chloroform (1:1) for 60 min at room temperature on an orbital rotor. The tubes were then centrifuged at room temperature for 10 min at 3,000g, the supernatant treated with 40 µl of RNAse (10 mg/ml) at 37° C. for 30 min and extracted with 4 ml phenol/chloroform. The DNA was precipitated with 400 µl 3M sodium acetate, pH 4.8, and 4 ml ice-cold isopropanol, spooled, washed with 70% ethanol, dried and redissolved in 100 µl sterile $dH_2O$. For PCR analysis, DNA was extracted from the leaves of plants using a FastDNA® kit (BIO 101 Inc., Vista, Calif., USA) according to the suppliers instructions. The DNA was eluted into 100 µl sterile deionized water and 1 µl used in PCR.

RNA Isolation from Plant Tissues

RNA was isolated from embryos, endosperm, developing grain or other tissues of hexaploid wheat at various times. Samples which had been frozen on dry ice immediately after harvesting were stored at −80° C. until required. RNA was extracted from each tissue using the following protocol. Samples were weighed and ground in liquid nitrogen using a mortar and pestle. After the liquid nitrogen had evaporated but the ground tissue was still frozen, 600 µl of NTES (0.1 M NaCl, 10 mM Tris-HCl (pH 8.0) 1 mM EDTA, 1% (w/v) SDS, 2% (w/v) β-mercaptoethanol) and 800 µl phenol/chloroform for every 200 mg of tissue were added and tissue was ground for a further 5 min. The aqueous phase was recovered after centrifugation at 11,000 g for 10 min at 4° C. and the RNA precipitated at −20° C. overnight with an equal volume of 4 M lithium chloride/10 mM EDTA, pelleted and washed with 70% ethanol. The RNA was allowed to air dry in a laminar flow hood for 10 min. The pellet was then dissolved in 360 μl DEPC treated H$_2$O and the RNA re-precipitated using 1 ml 95-100% ethanol and 40 μl 2 M sodium acetate, pH 5.8. After centrifugation, the RNA pellet was dried, dissolved in 20 μl of DEPC H$_2$O and treated with 1 μl DNase I (Invitrogen). After inactivation of DNase by adding 5 μl of DNase inactivation agent and centrifugation for 1 min at 10,000 g, the concentration of RNA in the supernatant was measured from the absorbance of the sample at 260 nm.

Quantitative Real-time PCR Analysis

RNA was extracted from imbibed *Arabidopsis* seeds using a CTAB buffer (2% CTAB, 2% polyvinylprrolidone K30, 100 mM Tris-HCl, 25 mM EDTA, 2,0 M NaCl, 2% β-mercaptoethanol), extracted twice with chloroform/isoamyl alcohol and precipitated with 2.5 M LiCl, re-extracted with chloroform/isoamyl alcohol and precipitated with ethanol (Chang et al., 1993). RNA was prepared from embryos isolated from imbibed barley grains using a method adapted from the hotborate method described by Wan and Wilkins (1994). Twenty-five embryos were ground to a powder in liquid nitrogen using a mortar and pestle. The powder was added to 4 mLs hot RNA extraction buffer (200 mM sodium borate decahydrate, 20 mM EGTA, 1% SDS, 10 mM DTT and 2% polyvinylpyrrolidone, pH 9.0) and vortexed. Once the homogenate had cooled, Proteinase K was added to a concentration of 0.5 mg mL-1 and incubated at room temperature for 20 min. Following centrifugation to remove insoluble debris, RNA was precipitated overnight with LiCl at 4° C. The following day the RNA pellet was solubilized in water, extracted with phenol/chloroform, ethanol precipitated and then purified on a mini RNeasy column (Qiagen). Twenty μg of total RNA from either *Arabidopsis* or barley was treated with 10 units of RQ1 RNase-free DNAse (Promega, Madison Wis.) for 15 min at 37° C. to remove DNA, then extracted with an equal volume of phenol/chloroform and precipitated with ethanol.

Two μg of this RNA was then used to synthesize cDNA in a 20 μL reaction using SuperScript II (Invitrogen) using the protocol outlined by the supplier. cDNA was diluted 40-fold and then 4.5 μL was used in 10 μL PCR reactions in 1×SYBR Green JumpStart™ Taq ReadyMix™ (Sigma, St Louis Mo.), and 1 μmol of each primer. Specific primers used for each *Arabidopsis* gene were as follows:

```
CYP707A1,
A1-F
5'-TTGGAAAGAGGAGACTAGAG-3'        (SEQ ID NO: 23)
and

A1-R
5'-CACTTGGTGTTTTCTCCTTG-3';       (SEQ ID NO: 24)

CYP707A2,
A2-F
5'-AAATGGAGTGCACTCATGTC-3'        (SEQ ID NO: 25)
and

A2-R
5'-CCTTCTTCATCTCCAATCAC-3';       (SEQ ID NO: 26)

CYP707A3,
A3'-F
5-ATTCTTGTCCAGGCAATGAG-3'         (SEQ ID NO: 27)
and

A3-R
5'-ATAGGCAATCCATTCTGAGG-3';       (SEQ ID NO: 28)

CYP707A4,
A4-F
5'-GAAAGGAATACAGTACAGTC-3'        (SEQ ID NO: 29)
and

A4-R
5'-GGATTAGATTTGGCTAACTAC-3';      (SEQ ID NO: 30)

NCED2,
N2-F
5'-GGATTCGAATGAACTCGTTG-3'        (SEQ ID NO: 31)
and

N2-R
5'-CCAAGTATCTAACCATTCTTC-3';      (SEQ ID NO: 32)

NCED3,
N3-F
5'-AGGTCGTGTGAGTTCTTATG-3'        (SEQ ID NO: 33)
and

N3-R
5'-CACTGGTAAATCTCGCTCTC-3';       (SEQ ID NO: 34)

NCED5,
N5-F
5'-GTTACGTTGGAACTAGAAGC-3'        (SEQ ID NO: 35)
and

N5-R
5'-CTAAAATCTGGCTCTGCAC-3';        (SEQ ID NO: 36)

NCED6,
N6-F
5'-TGAGAGACGAAGAGAAAGAC-3'        (SEQ ID NO: 37)
and

N6-R
5'-GTTCCTTCAACTGATTCTCG-3';       (SEQ ID NO: 38)

NCED9,
N9-F
5'-TAATGGTGTTCGTTCACGAC-3'        (SEQ ID NO: 39)
and

N9-R
5'-CTAACACAAAGCTTGCTT CG-3'.      (SEQ ID NO: 40)
```

The expression of each *Arabidopsis* gene was normalized by comparison with Cyclophilin (At2g29960) gene expression using the primers

```
C-F
5'-TGGACCAGGTGTACTTTCAATGG-3'     (SEQ ID NO: 41)
and

C-R
5'-CCACTGTCTGCAATTACGACTTTG-3'.   (SEQ ID NO: 42)
```

Specific primers used for each barley gene were as follows:

```
HvABA8H-1,
A5F
5'-AGCACGGACCGTCAAAGTC-3'         (SEQ ID NO: 43)
and

A5R
5'-TGAGAATGCCTACGTAGTG-3';        (SEQ ID NO: 44)

HvABA8H-2,
B13
5'-GAGATGCTGGTGCTCATC-3'          (SEQ ID NO: 45)
and

B32
5'-ACGTCGTCGCTCGATCCAAC-3';       (SEQ ID NO: 46)

HvNCED-1,
N10F
```

```
5'-CCAGCACTAATCGATTCC-3'        (SEQ ID NO: 47)
and

N10R
5'-GAGAGTGGTGATGAGTAA-3';       (SEQ ID NO: 48)

HvNCED-2,
N11F
5'-CATGGAAAGAGGAAGTTG C-3'      (SEQ ID NO: 49)
and

N11R
5'-GAAGCAAGTGTGAGCTAA C-3';     (SEQ ID NO: 50)

HvVP1,
V1F
5'-ACAGCAGTACACGGAATAC-3'       (SEQ ID NO: 51)
and

V1R
5'-GCTAGCTCAAGTATACCT-3'.       (SEQ ID NO: 52)
```

The expression of the barley genes was normalized to Iron Sulfur Subunit of Succinate Dehydrogenase (Accession number CB871628) gene expression using the primers:

```
SDF
5'-CACCAAACTAGATACAGCAC-3'      (SEQ ID NO: 53)
and

SDR
5'-TGGAGAAGTCGGAAAGTT G-3'.     (SEQ ID NO: 54)
```

Micro-array data and qRT-PCR analyses confirmed that these genes were not differentially expressed in imbibing D and ND seed or grains.

Reactions were prepared on a CAS-1200 Robotic Liquid Handling System (Corbett Robotics) and run on either a Rotor-gene RG-2000 or 3000A real-time PCR machine (Corbett Research) and data was analysed with Rotor-Gene software. The cycling conditions were 94° C. for 5 minutes, followed by 45 cycles of 94° C. for 15 seconds, 55° C. for 30 seconds and 72° C. for 20 seconds, followed by 40° C. for 5 minutes, 55° C. for 1 minute and the melt phase of 55° C. to 99° C. holding at 1° C. intervals for 5 seconds. This program was performed for all primer pairs used unless specified otherwise.

In Situ mRNA Hybridization

Barley embryos isolated from 6 h-imbibed D and ND grains were fixed overnight in 4% paraformaldehyde in PBS (pH 7.0) at room temperature for 1.5 h and then at 4° C. overnight. The fixed tissue was dehydrated through an ethanol series, followed by Histoclear and finally embedded in Paraplast Plus paraffin wax (Sherwood Medical, MO USA). 12.5 µm sections were cut and fixed onto polylysine-coated slides (Esco, Biolab Scientific, New Zealand and Australia). Digoxygenin-labelled antisense and sense probes were prepared from a 350 bp fragment (HvABA8'OH-1 genomic sequence bp 1357-1862) of the HvABA8'OH-1 cDNA coding region which showed little homology to HvABA8'OH-2. The following primer set was used to amplify the cDNA fragment: 5'-TGAAGTCAACACCTTCCAAG-3' (SEQ ID NO:55) and 5'-GTTGTCGGCGATCTGGTCGTC-3' (SEQ ID NO:56).

In situ hydridization experiments were performed as described previously (Coen et al., 1990; Jackson, 1991).

Generation and Analysis of Transgenic *Arabidopsis*

For constitutive expression in *Arabidopsis*, CYP707A1 was subcloned as an EcoR1 fragment behind the 35S promoter of the pART7 vector (Gleave, 1992) and its orientation was determined with an XbaI digestion. This 35S-CYP707A1 recombinant gene was then cleaved out as a Not1 fragment and cloned into the pART27 vector (Gleave, 1992), resulting in the binary vector p35S-707A1.

This vector was transformed into the *Agrobacterium tumefaciens* strain GV3101 and used to produce transformed plants of *Arabidopsis* ecotype C24 by standard methods (Clough and Bent, 1998). Transformants were selected on MS media with selection (kanamycin 50 µg/mL). Transformed *Arabidopsis* plants were moved to soil, grown and seed harvested as described above. Dormancy decay curves were generated for each line, also as described above.

Barley Transformation

The method used for the transformation of barley was based on the method of Tingay et al. (1997). The gene construct in pWBVec8 binary vector (Wang et al., 1998) were introduced into a highly virulent *Agrobacterium* strain (AGL1) by tri-parental conjugation, which was then used to introduce the T-DNA containing the transgene and the selectable marker gene (encoding hygromycin resistance, expressed from the CaMV35S promoter) into regenerable cells of the scutellum of immature barley embryos, as follows.

Developing barley seeds from the variety Golden Promise, 12-15 days after anthesis, were removed from the growing spike of greenhouse grown plants, and shaken in 70% ethanol for 1 minute then for twenty minutes in 20% (v/v) bleach+1 drop Tween 20 followed by rinsing seven times with sterile water. Embryos (approx 1.5 to 2.5 mm in size) were then removed from the seeds under sterile conditions and the axis cut from each embryo. The embryos were placed cut side up on a petri dish containing callus induction medium. The *Agrobacterium* transconjugants were grown in MG/L broth (containing 5 g mannitol, 1 g L-glutamic acid, 0.2 g $KH_2PO_4$, 0.1 g NaCl, 0.1 g $MgSO_4.7H_2O$, 5 g tryptone, 2.5 g yeast extract and 1 µg biotin per liter, pH 7.0) containing spectinomycin (50 mg/l) and rifampicin (20 mg/l) with aeration at 28° C., to a concentration of approximately $2-3\times10^8$ cells/ml, and then approx 10 µl of the cell suspension was added to the embryos in a petri dish. Excess *Agrobacterium* suspension was removed from the embryos, which were then transferred to a fresh plate of callus induction medium and placed in the dark for 2-3 days at 24° C.

The embryos were transferred to callus induction medium with selection (50 µg/ml hygromycin and 100 µg/ml Timentin). Embryos remain on this media for 2 weeks in the dark at 24° C. Healthy callus was then divided and placed on fresh selection media and incubated for a further 4 weeks at 24° C. in the dark, transferring healthy callus every 2 weeks. Following this, the embryos were incubated at 24° C. in the light for 2 weeks on regeneration medium with selection (20 µg/ml hygromycin and 100 µg/ml Timentin), containing cytokinin, transferring healthy callus every 2 weeks for a further 4-8 weeks. Once shoots were at least 1 cm or longer, they were transferred to rooting media with selection (25 µg/ml hygromycin and 100 µg/ml Timentin), containing cytokinin and auxin until healthy roots emerged, or for 2 four week periods. Juvenile plants were then transferred to soil mixture in small peat pots and kept on a misting bench for two weeks and finally transferred to larger pots in a glasshouse.

Wheat Transformation

In a preferred method, transformed wheat plants may be produced using an efficient *Agrobacterium*-mediated seed inoculation method as follows. The method is at least as efficient as other reported methods for wheat.

Genetic constructs for transformation of wheat may be introduced by electroporation into the disarmed *Agrobacterium tumefaciens* strain LBA4404 carrying the vir plasmid pAL4404 and pSB1, with subsequent selection on media with spectinomycin. Transformed *Agrobacterium* strains are incubated on solidified YEP media at 27° C. for 2 days. Bacteria are then collected and re-suspended in TSIM1 (MS media with 100 mg/l myo-inositol, 10 g/l glucose, 50 mg/l MES buffer pH5.5) containing 400 mM acetosyringone to an optical density of 2.4 at 650 nm for wheat inoculation.

Wheat plants (for example variety NB1, a Spring wheat variety, Nickerson Seeds Ltd, Rothwell, Lincs.) are grown in a glasshouse at 22/15° C. day/night temperature with supplemented light to give a 16 hour day. Tillers are harvested approximately 14 days post-anthesis (embryos approximately 1 mm in length) to include 50 cm tiller stem. All leaves are then removed from the tillers except the flag leaf, which is cleaned to remove contaminating fungal spores. The glumes of each spikelet and the lemma from the first two florets are then carefully removed to expose the immature seed. Generally, only these two seed in each spikelet are uncovered. This procedure is carried out along the entire length of the inflorescence. The ears are then sprayed with 70% IMS as a brief surface sterilization.

*Agrobacterium* suspensions (1 µl) are inoculated using a 10 µl Hamilton syringe into the immature seed approximately at the position of the scutellum:endosperm interface so that all exposed seed are inoculated. The tillers were then placed in water, covered with a translucent plastic bag to prevent seed dehydration, and placed in a lit incubator for 3 days at 23° C., 16 hr day, 45 µm$^{-2}$s$^{-1}$PAR. After 3 days of co-cultivation, the inoculated immature seed are removed and surface sterilized with 70% ethanol (30 sec), then 20% bleach (Domestos™, 20 min), followed by thorough washing in sterile distilled water. Immature embryos are aseptically isolated and placed on W3 media (MS supplemented with 20 g/l sucrose and 2 mg/l 2,4-D and solidified with 6 g/l Type I agarose, Sigma) with the addition of 150 mg/l Timentin (W3T) and with the scutellum uppermost (20 embryos per plate). Cultures are placed at 25° C. in the light (16 hour day, 80 µm$^{-2}$s$^{-1}$PAR). The development of the embryonic axis on the embryos is assessed about 5 days after isolation and the axis removed where necessary to improve callus production. The embryos are maintained on W3T for 4 weeks, with a transfer to fresh media at 2 weeks post-isolation, and assessed for embryogenic capacity.

After 4 weeks growth, callus derived from the inoculated embryos is very similar to control callus obtained from uninoculated embryos plated on W3T medium. Presence of the bacteria does not appear to have substantially reduced the embryogenic capacity of the callus derived from the inoculated embryos. Embryogenic calli are transferred to W3 media with 2 mg/l Asulam or geneticin at 25 mg/l as selective agent, as appropriate, and 150 mg/l Timentin (W32AT). Calli are maintained on this media for a further 2 weeks and then each callus is divided into 2 mm-sized pieces and re-plated onto W32AT. Control embryos derived from inoculations with the LBA4404 without binary vector constructs do not produce transformed callus on selection media.

After a further 2 weeks culture, all tissue is assessed for development of embryogenic callus: any callus showing signs of continued development after 4 weeks on selection is transferred to regeneration media (RMT-MS with 40 g/l maltose and 150 mg/l Timentin, pH 5.8, solidified with 6 µl agarose, Sigma type 1). Shoots are regenerated within 4 weeks on this media and then transferred to MS30 with 150 mg/l Timentin for shoot elongation and rooting. Juvenile plants are then transferred to soil mixture and kept on a misting bench for two weeks and finally transferred to a glasshouse.

Alternative *Agrobacterium* strains such as strain AGL1 or selectable markers such as genes encoding hygromycin resistance can also be used in the method.

Embryo Excision and Biolistic Transformation

Transformation of wheat embryos may be performed according to the method of Pellegrineschi et al. (2002). Approximately one hundred seeds are removed from heads of hexaploid wheat at approximately 10 days post anthesis and sterilised, by washing seed in 50 ml of 10% (v/v) bleach for 20 mins, followed by rinsing with sterile water. The embryo from each seed is removed, the axis excised and the embryos placed scutellum down on osmotic media (or wheat MSM). Approximately 30 embryos are placed within a 2×2 cm square in the centre of the plate. The 30 embryos are allowed to remain untouched for a period of no shorter than 2 hrs and no longer than 4 hrs.

While the embryos are on osmotic medium, the gold/DNA mixture is prepared. A 50 µl aliquot of gold is sonicated for 2 mins before the addition of 5 µg of plasmid DNA. Plasmid DNA is a mixture of the RNAi encoding plasmid and the resistance plasmid pNeo in a ratio of 1:1. The mixture is vortexed briefly then 50 µl of 2.5 M CaCl$_2$ and 20 µl 0.1 M spermidine are placed into the lid of the tube before vortexing into the gold to precipitate the DNA onto the gold. The sample is centrifuged for 5 seconds, the supernatant removed, 150 µl of 100% ethanol added and the gold mixture resuspended. The spin is repeated, and again the supernatant is removed, before the gold mixture is resuspended in 85 µl of ethanol in preparation for use in embryo bombardment.

Ten µl of the gold mixture is used in each bombardment except for the one plate of embryos left un-bombarded to act as a regeneration control. Bombardment is carried out at 900 psi at a distance of 9 cm. After bombardment, plates containing embryos are placed in the dark at 26° C. After 24 hours, embryos are transferred face down to induction media (or wheat MSR), which contains 2,4D to induce callus formation, and once again plates are placed in the dark at 26° C.

After 2 weeks the callus has developed and is transferred to maturation media (or wheat MSW), with antibiotic selection, to allow for the development and differentiation of transformed plant tissue. Plates are placed in the light at the constant temperature of 26° C. and were left undisturbed for up to three weeks. During this time, greening of some callus occurs. After 3 weeks, green callus is transferred to fresh media to allow for further plant development. Typically, plants are transferred another two times (6 weeks) before being planted into soil or vermiculite in the greenhouse.

Screening of Putative Transformed Wheat Plants

Leaf DNA was extracted using the fast DNA extraction kit and each individual plant screened for the presence of the transgene by PCR analysis. A leaf sample is taken from an untransformed plant to act as a PCR control.

Example 2

ABA Measurement in Dormant and Non-dormant Seed of *Arabidopsis* and Barley

Generation of Dormant and Non-dormant Seeds/Grains from *Arabidopsis* and Barley

*Arabidopsis* (ecotype C24) and barley (cv. Proctor) plants grown under cool temperatures produced seeds (grains) that were highly dormant and required extended periods of after-ripening or stratification to break dormancy (Koornneef et al., 2000, Jacobsen et al., 2002). To analyse dormancy mechanisms in *Arabidopsis* C24 and barley Proctor seeds, freshly harvested seeds were divided into two samples, with one allowed to after-ripen for 3-4 months to allow dormancy to decay ("non-dormant", ND) and the other stored at −80° C. to retain dormancy ("dormant", D). Germination kinetics were compared for both D and ND seed from the same harvest. The data are shown in FIGS. 2A and 2C.

The present inventors found that 80-90% of ND *Arabidopsis* and barley seed germinated within a few days of imbibition. In contrast, less than 10% of D seed germinated in this time period. Stratifying the *Arabidopsis* D seed at 4° C. for 7 days was sufficient to break dormancy, with approximately 95% of the seed germinating after 4 days of imbibition, verifying that the D seed was viable. ND and D seed samples were then used to analyse changes in ABA content and gene expression profiles during imbibition.

Analysis of ABA Content in ND and D Seeds

ABA was extracted from dry and imbibed *Arabidopsis* seed and quantified using GC-MS-SIM as described in Example 1. In dry seed, ABA content was similar in ND and D seeds (FIG. 2B), implying that the after-ripening period had not altered ABA content. During the first 6 h of imbibition, ABA levels fell rapidly to similar levels in both ND and D seeds. However, by 12 h of imbibition the ABA levels in ND seeds fell to half that of D seeds (FIG. 2B). After 24 h of imbibition, ABA content in ND seeds was more than 2-fold lower than that in D seeds and only 10% of the level found in the dry ND seed.

In barley, similar results were obtained (FIG. 2D). In the non-imbibed grain, there was no difference in ABA content between D and ND embryos. The ABA content of D and ND embryos declined rapidly during the first 6 h of imbibition. Subsequently the ABA content in ND embryos fell to a markedly lower level than in D embryos (FIG. 2D). The observed pattern of ABA decline was consistent with that reported previously for barley (Jacobsen et al., 2002).

Example 3

Expression of NCED and ABA8'OH Genes in D and ND Seeds in *Arabidopsis*

In *Arabidopsis* there are four cytochrome P450 genes within the CYP707A subfamily all of which encode ABA8'OH (Kushiro et al., 2004; Saito et al., 2004). Using qRT-PCR we found that AtCYP707A2 was the most highly expressed of these genes in C24 seeds (FIG. 3), which was consistent with previous findings from the *Arabidopsis* ecotype Columbia (Kushiro et al., 2004). AtCYP707A2 increased rapidly in ND seeds, reached a maximum by 6 h, and decreased thereafter. In contrast AtCYP707A2 expression in D seed increased during the first 3 h of imbibition but declined rapidly so that by 6 h it was 4 fold lower than in ND seed (FIG. 3A). The increased expression of AtCYP707A2 in ND seed compared to D seed between 3 h and 6 h imbibition correlated closely with the accelerated decline in ABA content in ND seed following 6 h imbibition.

AtCYP707A3 was also expressed in imbibed seeds but at a much lower level than AtCYP707A2. At 3 h imbibition the expression was higher in D seeds but after 6 h there was no difference between D and ND seed (FIG. 3B). Both AtCYP707A1 and AtCYP707A4 were expressed at low levels and no differences were detected in expression level between D and ND seeds.

In *Arabidopsis* there are five genes, AtNCED2, AtNCED3, AtNCED5, AtNCED6 and AtNCED9, encoding NCED enzymes (Iuchi et al., 2001). Using qRT-PCR we could detect expression of all five genes. However, the expression of AtNCED3 was very low and none of the genes were differentially expressed in imbibing D and ND seeds (FIG. 3C-F). Expression of AtNCED5 and AtNCED9 increased during the first 6 h of imbibition (FIG. 3C-F), but declined after this time. In contrast AtNCED2 and AtNCED6 expression declined during the first 12 h of imbibition. After this point, neither the AtNCEDs nor the AtCYP707As had notable changes of expression (FIG. 3). In conclusion, it appeared that differences in ABA content in imbibing D and ND *Arabidopsis* seeds were not related to differences in NCED expression.

Example 4

Modification of ABA8'OH Expression in *Arabidopsis* and Altered ABA Levels and Dormancy To determine whether increasing the level of enzyme activity of ABA8'OH could lower the level of seed dormancy, the AtCYP707 μl protein coding region was placed under the control of the CaMV 35S promoter, resulting in the binary vector p35S-707A1 (see Example 1) and introduced into *Arabidopsis* by *Agrobacterium*-mediated transformation methods. These experiments used the *Arabidopsis* ecotype C24 that had naturally high seed dormancy and required relatively long periods (10-12 weeks) of after-ripening at room temperature for dormancy to be broken (Koornneef et al., 2000). T1 transgenic plants were obtained and, under well-watered growth conditions, were the same in phenotype and morphology as wild-type plants which were grown alongside the transgenics. Seed was collected from the T1 primary transformants and germinated on selective media, from which T2 resistant plants (20 plants for each line) were transferred to soil, grown and freshly set T3 seed was harvested. Using this seed, ABA levels and dormancy decay curves were determined.

ABA concentrations were determined in wild-type and four independent 35S-707A1 transgenic lines. Reductions in ABA levels were found in all transgenic lines, with two of these lines having ABA concentrations less than 30% of that of wild-type C24 seeds (FIG. 4A). Consistent with these lower ABA levels, the transgenic lines required shorter after-ripening periods to break dormancy. The smallest reduction in ABA level was observed in line 11 and this line exhibited germination behavior closest to that of the wild-type.

FIG. 4B shows the dormancy decay curves for seed from the wild-type and the four independent 35S-707A1 transgenic lines. After six weeks of after-ripening, over 80% of seeds germinated in each of the 35S-707A1 transgenic lines. In contrast, approximately only 20% of C24 seeds germinated (FIG. 4B). Transgenic lines transformed with the binary vector pART27 lacking the 35S-707A1 gene insert (empty vector control) germinated similarly to the wild-type. Therefore, the introduction of the 35S-707A1 transgene into *Arabidopsis* resulted in both lower ABA levels in the resulting seed and lower seed dormancy.

To determine whether a mutation in the *Arabidopsis* CYP707A2 gene altered the period of after-ripening required to break dormancy, the dormancy decay curves of wild-type (ecotype Columbia; low dormancy) seed was compared that of seed from the T-DNA insertion mutant cyp707a2-1 that had been previously identified (Kushiro et al. 2004). For genotyping of the mutant, the following primers were used:
A2-5,5'-CCACCGCTTCTGTCTTAACTTGGCTTCT-3' (SEQ ID NO:57) and A2-3,5'-CTGAAGGAAGTAGTGAG-GTGGTGAAGGA-3' (SEQ ID NO:58). These hybridised to positions flanking the T-DNA insertion site in the cyp707a2-1 mutant (Salk_072410) which is in the fifth intron of the AtCYP707A2 (At2g29090) gene (Kushiro et al., 2004).

Thus, amplification on a wild-type allele template DNA gave a product of 1186 bp while the mutant allele did not yield a PCR product with these primers. However, amplification of the mutant allele with A2-3 and a T-DNA specific primer LBa1 5'-TGGTTCACGTAGTGGGCCATCGCCCTGAT-3' (SEQ ID NO:59) yielded a product of approximately 0.9 Kb (921 bp).

From a segregating population of CYP707A2/cyp707a2-1 plants, seeds were harvested from either wild-type (CYP707A2/CYP707A2) or mutant (cyp707a2/cyp707a2) plants genotyped using the PCR method, and the level of dormancy determined using germination assays. The results are shown in FIG. 5. The cyp707a2-1 allele was in the Columbia background which had been previously reported to have low dormancy (Koornneef et al., 2000). This was reflected in the observation that immediately after harvest, 70% of wild-type Columbia seed germinated (FIG. 5). In contrast only 10% of cyp707a2-1 seed germinated immediately after harvest, implying that this mutant had higher levels of dormancy due to inactivation of the CYP707A2 gene. After three weeks of after-ripening, the level of germination was similar for both wild-type and cyp707a2-1 seeds. These experiments confirmed that inactivation of the CYP707A2 gene resulted in increased dormancy, consistent with a decrease in ABA catabolism.

Example 5

Isolation of NCED and ABA8'OH Genes from Barley

In an attempt to identify genes that might be involved in seed dormancy in cereals, the inventors investigated whether CYP707A and/or NCED related gene families existed in barley and wheat.

The strategy used was to first identify rice genes, from sequences in databases, that were analogous to the *Arabidopsis* CYP707A genes, and then look for barley and wheat expressed sequence tags (ESTs) that were closely related to the rice genes. Phylogenetic analysis of rice and *Arabidopsis* P450 genes available on a database (drnelson.utmem.edu/rice.html) indicated that rice had two apparent CY707A genes (CYP707A5 and CYP707A6) whereas *Arabidopsis* had 4 genes (CYP707A1-4) in this family as described above. To date, which of these rice genes, if any, encodes a functional ABA8'OH protein has not been reported. Furthermore, there were no reports demonstrating expression of the rice CYP707A genes in embryos or developing or germinating grain.

The rice CYP707A5 and CYP707A6 sequences were used to query the NCBI EST databases using the BLAST program. A number of related barley and wheat ESTs were identified. ESTs CA008406.1, CA001959.1, BJ483016.1, BQ466895.1, BQ662339.1, BE414902 and BJ278008 were identified in BLAST searches as being related to the rice CYP707A5 gene more closely than to CYP707A6.

Two PCR primers (5'-CCAAGTACAGATGGTCTAC-3' (SEQ ID NO:60) and 5'-TGAGAATGCCTACGTAGTG-3' (SEQ ID NO:44)) based on sequences present in barley ESTs (BJ483016.1 and BQ662339.1) were used to amplify a CYP707A5 3' gene fragment, corresponding to bp 2711-3116 of the HvABA8'OH-1 genomic sequence (FIG. 6). The PCR reaction used, as template, cDNA derived from RNA isolated from barley embryos (cv Proctor) isolated after 12 h imbibition. Taq polymerase was used to amplify the 3' gene fragment. The PCR reaction was performed at 95° C. for 5 min followed by 35 cycles of 95° C., 30 s; 56° C., 30 s; and 72° C., 30 s. This fragment was labeled and used as a probe to screen barley genomic libraries in order to isolate the full length genes that were orthologous to rice CYP707A5.

Wheat ESTs related to rice CYP707A6 were also identified in NCBI BLAST searches. Two PCR primers (5'-GGAGAAAGGCTACAACTC-3' (SEQ ID NO:61) and 5'-TGATGGATGTTCCTGAAGAG-3' (SEQ ID NO:62)) were synthesized based on sequences in wheat EST CD919420.1. Using Taq polymerase and wheat (cv Bob White) genomic DNA as template with the primers, δ 800 bp wheat genomic DNA fragment was isolated. This fragment was labeled and used as a probe (A-6 probe) for screening barley genomic libraries to identify genes related to the rice CYP707A6 gene. The PCR reaction was performed at 95° C. for 5 min, then 40 cycles of 95° C., 30 s; 53° C., 30 s; 68° C., 1 min. The products of the PCR reactions were analysed by agarose gel electrophoresis and were shown to contain a single band.

Isolation of CYP707A-related Genes from Barley

A *Hordeum vulgare* (cv Morex) genomic BAC library (Clemson University Genomics Institute BAC/EST Resource Center, www.genome.clemson.edu/groups/bac/) was screened with probes made from gene fragments of the putative barley CYP707A5 and wheat CYP707A6 genes, as described above. Filters with the arrayed BAC library were incubated overnight with the $^{32}$P-labeled probes in hydridization buffer (5×SSC, 50% formamide, 0.2% SDS, 10 mM EDTA, 5×Denhardt's, 50 mM Tris, pH 8.0. 0.1mg/ml denatured salmon sperm DNA) at 42° C. The filters were washed twice with 2×SSC and 0.1% SDS at 42° C. and twice with 0.1×SSC and 0.1% SDS at 42° C. Positive BACs identified in the primary screen were confirmed by Southern blot hybridization analyses using the same probes.

Barley BAC 735F13 was identified as a positive clone with the A-5 probe and was selected for further analysis and subcloning. Following restriction mapping of the gene, designated HvABA8'OH-1, on BAC 735F13 using EcoRI, HindIII, BamHI, XhoI, XbaI and SalI, restriction fragments were cloned into pBluescript and sequenced. The genomic sequence of HvABA8'OH-1 is provided as SEQ ID NO:1 and FIG. 6.

BAC 687C24 which hybridized with the A-6 probe was selected for further analysis and for sub-cloning of a second gene designated HvABA8'OH-2. Following restriction mapping of the gene on BAC 735F13 using EcoRI, HindIII, BamHI, XhoI, XbaI and SalI, an XbaI fragment was cloned into pBluescript and partially sequenced.

Cloning of cDNAs Encoding Barley ABA8'OH Proteins

Corresponding cDNAs were amplified from a pCM-VSPORT6 plasmid cDNA library (Invitrogen Life Technologies, Carlsbad USA) made from RNA isolated from embryos isolated from 12 h-imbibed dormant Proctor barley grains. Using primers based on the 5'UTR sequence (5'-GGATC-CGTTGCAGGTTGCAGGTAACAGAAC-3') (SEQ ID NO:63) and 3'UTR sequence (5'-GAATTCGGACACT-GACGGATGGAGAAC-3' (SEQ ID NO:64)) of HvABA8'OH-1 and a high fidelity DNA polymerase PfuI, a 1541 bp cDNA fragment containing the complete ORF was amplified. The PCR reaction was heated to 95° C. for 2 min and then 35 cycles of 95° C., 30 s; 55° C., 30 s; and 72° C. for 2 min. The sequence is provided as SEQ ID NO:2. The 5' UTR was from nucleotides 1-43, the protein coding region (ORF) from nucleotides 43-1446 (SEQ ID NO:3), and the 3' UTR from 1447-1541.

Using primers based on the 5'UTR sequence (5'-AG-GATCCACCTCGCTGGTCTGAGTGATC-3' (SEQ ID NO:65)) and 3'UTR sequence (5'-AGAATTCGTCACAC- TATCACTTCGTC-3' (SEQ ID NO:66)) of HvABA8'OH-2 gene in combination with a high fidelity DNA polymerase, a 1567 bp cDNA fragment containing the complete ORF was amplified. The PCR reaction was heated to 95° C. for 2 min and then 35 cycles of 95° C., 30 s; 55° C., 30 s; and 72° C. for 2 min. The sequence is provided as SEQ ID NO:5. The 5' UTR was from nucleotides 1-45, the protein coding region (ORF) from nucleotides 46-1555 (SEQ ID NO:6), and the 3' UTR from 1556-1567.

The barley gene sequences were compared to CYP707A genes from other species. Sequence alignments were done with the ClustalW 1.8 Global progressive program available at searchlauncher.bcm.tmc.edu/and phylogenetic trees constructed using the TreeTop—Phylogenetic Tree Prediction program available at www.genebee.msu.su/services/phtree_reduced.html. The gene HvABA8'OH-1 encoded a 468 amino acid protein (SEQ ID NO:4) that had 87.1% identity to OsCYP707A5 and 66.7% identity to At707A1 proteins. The other barley gene, HvABA8'OH-2, encoded a 506 amino acid protein (SEQ ID NO:7) that had 71.2% identity to the OsCYP707A6 and 58.7% identity to AtCYP707A4 proteins.

The higher identities between genes from the same clades (FIG. 7A), compared to the identities between HvABA8'OH-1 and HvABA8'OH-2 (53.0%) indicates that these genes arose from a duplication event before the speciation of the grasses and possibly before the divergence of monocotyledonous and dicotyledonous plants.

Based on our expression data (see below) which indicated that HvABA8'OH-1 was likely to play the major role in the degradation of ABA to phaseic acid in non-dormant barley embryos, functional assays were performed in yeast cells to demonstrate that HvABA8'OH-1 encoded a functional ABA8'OH enzyme. The gene was expressed in yeast cells and ABA8'OH activity was assayed as described in Example 1. Reaction mixtures containing ABA and microsomes from yeast expressing HvABA8'OH-1 were incubated. Gas chromatography-mass spectrometry (GC-MS) analysis of the reaction products showed the presence of a phaseic acid (PA) methyl ester product which was identified by comparison with an authentic PA methyl ester standard. The kovats retention index (KRI) value for the product was 2199, which was identical to the KRI value for the PA methyl ester standard. The background subtracted ion peak data for the product produced by the HvABA8'OH-1 transgenic yeast were as follows (percentage relative abundance for the HvABA8'OH-1 product/PA methyl ester standard): 294 [M+] (7/6), 276 (6/6), 244 (6/6), 177 (16/15), 167 (23/22), 139 (56/40), 135 (40/37), 125 (100/100), 122 (64/65), 121 (66/66), 109 (35/31), 94 (55/59). The presence of PA in the reaction products verified that HvABA8'OH-1 encoded ABA8'OH activity.

Isolation of NCED-related Genes from Barley cDNAs encoding NCEDs were isolated from the pCM-VSPORT6 plasmid cDNA library using the GeneTrapper® cDNA Positive Selection System (Invitrogen Life Sciences). Biotinylated oligonucleotides 5-GACGTCATCAAGAAGC-CTTACC-3 (SEQ ID NO:67) and 5-ATGTCATCAA-GAAGCCGTACCTC-3 (SEQ ID NO:68) designed from partial EST genomic sequences encoding barley NCEDs were used to isolate two full length cDNAs from the library. These barley cDNAs encoded proteins with high amino acid sequence similarity to previously isolated NCED genes. Termed HvNCED1 and HvNCED2, these genes were highly similar to Viviparous14 (ZmVP14) of maize (Schwartz et al., 1997), being 70.2% and 81.2% identical respectively, and clustered within the group of the five known NCED genes of *Arabidopsis* (FIG. 7B).

Example 6

Expression of NCED and ABA8'OH Genes in Embryos from D and ND Grains of Barley

The expression profiles of the genes corresponding to the isolated NCED and ABA8'OH sequences were determined in embryos from imbibed barley grains using quantitative reverse transcription PCR (qRT-PCR) as described in Example 1. The expression of HvABA8'OH-1 in comparison to the control gene was much higher than that of HvABA8'OH-2, suggesting that the ABA8'OH activity in embryos of imbibed seed was likely to be predominantly encoded by HvABA8'OH-1. Furthermore, HvABA8'OH-1 was differentially expressed between ND and D barley grains, with expression in ND embryos being induced within 6 h of imbibition and remaining higher than in embryos from D seed (FIG. 8A). Thus, similar to *Arabidopsis*, the difference in ABA levels found in embryos from D and ND barley grains may, at least in part, be explained by the different levels of HvABA8'OH-1 expression observed in these tissues.

Expression of both of the HvNCED genes was detected in embryos of imbibing barley grains. Both genes were differentially expressed in D and ND embryos. HvNCED1 was up-regulated during imbibition in both D and ND embryos (FIG. 8B), however it was induced to a greater extent in D seeds (approximately 4-fold) than ND (approximately 2.5 fold). The increased expression of HvNCED1 in D embryos may contribute to higher ABA content in the D barley embryos. In contrast, HvNCED2 expression in ND embryos was higher than in D embryos during imbibition (FIG. 8C), which was not consistent with the observation of lower ABA levels in the ND seed.

Another gene known to have a role in ABA signaling, Viviparous 1 (HvVP1) was also assayed in barley seed. The corresponding gene in wheat encodes a transcription factor which has been thought responsible for a lack of dormancy in modern wheat varieties (McKibbin et al 2002). The barley HvVP1 sequence (Accession number AY150678) had been published in the Genbank database. Although expression of this gene was detectable, no differences could be found between D and ND tissues (FIG. 8D).

In Situ Localization of HvABA8'OH-1 mRNA in ND and D Embryos

The expression pattern of HvABA8'OH-1 in D and ND embryos was examined more closely by RNA in situ analysis as described in Example 1. Typical in situ hybridisation patterns are shown in FIG. 9. In embryos from ND grains imbibed for 6 h, hybridization signal was limited to the coleorhiza in which the primary and lateral roots are embedded (FIGS. 9B and C). The signal was strong in coleorhiza cells near the root apex but was also detected in more distant cells which abut the mesocotyl and scutellum. HvABA8'OH-1 expression was not observed in other embryonic tissues (roots, scutellum, mesocotyl, coleoptile and shoot apex) in imbibed ND embryos (FIG. 9D). The absence of detectable HvABA8'OH-1 expression in embryos of imbibed D grains (FIG. 9E) was consistent the previous qRT-PCR results which showed that HvABA8'OH-1 expression was lower in imbibed D embryos compared to ND embryos. Hybridization with a sense probe failed to detect any signal in ND (FIG. 9F) and D embryos from 6 h-imbibed grains.

Discussion

Based on the relationship between dormancy and ABA metabolism in two different plant systems, *Arabidopsis* and barley, and the determination of ABA levels, gene expression profiles, and dormancy levels in mutant and transgenic plants, it was concluded that the level of expression of ABA8'OH was an important determinant in whether the seed (grain) remained dormant or germinated. In an earlier study, it was concluded that no clear relationship existed between the ABA content of the mature seed/grain and its level of dormancy (King, 1989).

The present inventors also found no difference in the ABA levels between D and ND seed of *Arabidopsis*, or embryos from D and ND barley grains, similar to other recent studies with these species (Jacobsen et al., 2002; Ali-Rachedi et al., 2004). For the *Arabidopsis* ecotype Cape Verdi Islands (Cvi), after 24 h of imbibition, D seed had ABA levels that were approximately twice that of ND seed (Ali-Rachedi et al., 2004), similar to the findings for the C24 ecotype, where D seeds also had approximately twice as much ABA as ND seeds. A similar observation was made for barley, with no difference in ABA levels between embryos from D and ND non-imbibed grain, but higher levels of ABA in embryos from imbibing D grains than in ND grain (Jacobsen et al., 2002). Together these data imply that the after-ripening period did not affect ABA levels per se. Rather, after-ripening had made the seed more "competent" to degrade ABA to a lower level than in D seed, and this is what appeared to distinguish D from ND tissues.

Although ABA levels remained higher in D seeds, ABA levels decreased substantially upon imbibition. This suggests that ABA catabolic activity was present in mature dry D seeds, and upon imbibition, this activity was responsible for the rapid degradation of ABA. Despite this decline in ABA, these seeds were still unable to germinate, implying that the ABA levels were still sufficiently high to impose dormancy. As determined by ABA dose response curves, 2-3 fold differences in ABA levels can determine whether a seed germinates or remains dormant (for example, Beaudoin et al., 2000 and Ghassemian et al., 2000), implying that the observed differences after 24-h of imbibition could be biologically significant.

As described above, of the genes tested in *Arabidopsis*, only the AtCYP707A2 gene was found to be differentially expressed between imbibing D and ND seeds. This gene had previously been shown to be the most highly expressed of the ABA8'OH genes in imbibing seeds and mutations within it led to the seeds being hyperdormant (Kushiro et al., 2004). As described above, the level of expression of this gene was well correlated with the ABA levels in D and ND seeds. Interestingly, during the first 3 h of imbibition the expression level of the gene increased in a similar fashion in both D and ND seeds. This was consistent with ABA levels declining rapidly and identically in both D and ND seeds during the first 6 h of imbibition. However after this time, the gene was repressed in D seeds, while its expression continued to increase in ND seeds. Thus the "pulse" of induction of AtCYP707A2 was greater in ND seeds, and this was consistent with the lower levels of ABA.

Although several of the AtNCED genes were induced during the first 3-6 h of imbibition, none of the genes were differentially expressed between D and ND seeds, and all were expressed at lower levels than AtCYP707A2. This induction of AtNCED genes suggested that both in D and ND seeds, ABA biosynthesis was occurring soon after imbibition despite the ABA levels rapidly declining during this period. However, the observed AtNCED expression did not appear to contribute significantly to the overall level of ABA in the imbibing seed. The AtNCED genes may play a role in regulating dormancy, but this role appeared occur later in the germination process, where their induction may be required to restore ABA concentrations to pre-imbibed levels.

Two genes were identified in barley that belong to the CYP707A subfamily. The present inventors have determined that the expression of one gene, HvABA8'OH-1, predominated in imbibing seeds and was differentially expressed in embryos from D and ND grains. Again this gene had a higher level of expression when compared to the two HvNCED genes isolated, which was consistent with a tissue that was rapidly degrading its ABA. HvNCED1 and HvNCED2 had different expression profiles between D and ND grains, however HvNCED1 was higher in D, whereas HvNCED2 was higher in ND, so these expression differences may cancel one another out. This suggested that NCED made little contribution, if any, to the differences in ABA levels found in imbibing D and ND barley grains.

All changes in *Arabidopsis* gene expression levels occurred within the first 12 h of imbibition, after which time expression levels of all genes tested remained low. These dynamic expression profiles implied that changes took place very early in imbibition and resulted in a cascade of events leading to the seed either remaining dormant or germinating after 48-72 h of imbibition. These expression profiles contrasted with those of barley, where for instance the HvABA8'OH-1 levels are induced for a more sustained period of time. Although this may reflect the greater size of the barley grain compared to *Arabidopsis* seed, the decline in ABA occurred just as quickly in barley as in *Arabidopsis*.

The data showed that endogenous ABA levels could be manipulated through the over-expression of an ABA8'OH gene, and this resulted in a reduced requirement for after-ripening in order for dormancy to decay in these 35S-707A1 transgenic seeds. This reduced dormancy probably reflected lower ABA in the embryo as well as a greater potential to catabolize ABA upon imbibition. The changes in the after-ripening periods of these transgenic plants were dramatic, with some lines reaching 70-80% germination after 3 weeks. In contrast wild type seed germination was less than 60% after 9 weeks of after-ripening.

Conversely, a T-DNA tagged mutant cyp707a2-1, required a longer period of after-ripening to break dormancy than the corresponding wild type plants, and it was previously shown that these plants had six-fold higher levels of ABA in seeds compared to wild type plants (Kushiro et al., 2004). Therefore greater dormancy in this mutant was probably due to a combination of higher ABA levels in the embryo and a reduced capacity to catabolize the ABA upon imbibition. Presumably, during imbibition, either the other CYP707A genes present in *Arabidopsis* seeds were able to slowly degrade the ABA (Kushiro et al., 2004), or alternative ABA catabolic pathways were active in these tissues, such as conversion to the ABA-glucose ester (Chiwocha et al., 2005).

Localisation of HvABA8'OH-1 Expression in Barley Embryos

The coleorhiza contains a body of relatively undifferentiated parenchyma cells in which the roots are embedded. When non-dormant grains were hydrated, the coleorhiza elongated beyond the seed coats (defined as germination) and roots emerged from it. After 6 h hydration, HvABA8'OH-1 was expressed strongly and uniformly through the coleorhiza in the region of the primary root tip. However, expression did not occur anywhere else in the embryo. This pattern indicated that in the early hours of hydration, ABA catabolism occurred mainly in the coleorhiza but not in any other embryonic tissue. Thus the coleorhiza are thought to play a crucial role in determining whether or not germination occurred. ABA in dormant grains might prevent germination by preventing the coleorhiza from growing and that catabolism of ABA in non-dormant grains removed this constraint. The observed preferential expression of the ABA8'OH-1 genes in embryos indicated this gene as the preferred target for modulation of ABA8-hydroxylase activity in cereals.

Example 7

Construction of Hairpin RNAs and Insertion into Barley

The results described above indicated that increased HvABA8OH-1 expression in non-dormant grains correlated with reduced grain dormancy and lower ABA content in imbibed grains. Conversely, reduced HvABA8OH-1 expression was predicted to be associated with increased grain dormancy and higher ABA content. To confirm this and show that HvABA8OH-1 regulated grain dormancy, barley was transformed with a gene construct designed to express an inhibitory RNA molecule, to reduce HvABA8'OH-1 expression in the transgenic plants. Comparison of the cDNA sequences of HvABA8'OH-1 and HvABA8'OH-2 revealed a 421 bp region of HvABA8'OH-1 (nucleotides 427-848 of the cDNA sequence) that showed lower similarity to the corresponding region of the HvABA8'OH-2 cDNA than other regions. Within this region, the longest sequence with 100% identity to the corresponding region in HvABA8'OH-2 was 10 base-pairs, indicating that the designed inhibitory RNA would likely be specific to the HvABA8'OH-1 gene.

The region 427-848 bp of the HvABAOH-1 cDNA was amplified by PCR using primer pairs with either BamHI and SmaI restriction sites at the 5' end or SpeI and Acc651 restriction sites at the 5' end. The sequences of the first primers were 5'-AAGGATCCGACTACCACACCCACCTC-CGCCGTCTC-3' (SEQ ID NO:69) and 5'-AACCCGG-GATCTGGTCGTCGGTGAGCGCCTC-3' (SEQ ID NO:70). The sequences of the second primers were 5'-AAG-GTACCGACTACCACACCCACCTCCGCCGTCTC-3' (SEQ ID NO:69) and 5'-AAACTAGTATCTGGTCGTCG-GTGAGCGCCTC-3' (SEQ ID NO:71). The amplified products were directionally cloned on either side of the cre intron in the moncot RNAi vector pSTARLING-A using the cloning sites BamHII SmaI and SpeI/Acc651, creating pSTARLING RNAi-HvABA8'OH-1. Thus, the two copies of the HvABA8'OH-1 fragment were in an inverted orientation with respect to each other.

The resultant gene cassette was inserted into the *Agrobacterium* binary vector pVec8 as a NotI fragment, creating pVec8 RNAi-HvABA8'OH. This vector was transferred into *Agrobacterium tumefaciens* strain AGLO by triparental conjugation. Cells of the transconjugants were used to introduce the gene construct into barley (*Hordeum vulgare* L cv. Golden Promise) using the technique as described by Murray et al. (2003) and in Example 1. Transformed barley plants were selected on media containing hygromycin. At least 45 independent transformed plants were obtained; these were designated rABA8'OH-1 plants. PCR was used to confirm the presence of the T-DNA insertion in these barley plants. DNA was isolated from the plants using the method described by Matthews et al. (2001) and screened for the presence of the hygromycin gene using PCR with oligonucleotides Hyg 5 (5'-ACTCACCGCGACGTCTGTC-3') (SEQ ID NO:72) and Hyg 3 (5'-GCGCGTCTGCTGCTCCAT-3') (SEQ ID NO:73) as primers. 45 lines were identified positive by the presence of a 900 bp PCR product derived from the hygromycin resistance gene. Southern blot hybridization analysis was also used to confirm the presence of the transgene.

The expression level of the transgene encoding the inhibitory RNA was analysed by Northern blot hubridisation using an ABA8'OH-1 probe. The results (FIG. 10) showed that the hairpin RNA was expressed in all lines tested except for line 3, with the highest level of expression in line 7.

Grains (T1 seed) harvested from the initial transformants (T0 plants) were tested for changes in dormancy level and ABA content in the embryos relative to grains from Golden Promise plants grown side by side with the transgenic lines. Grain dormancy was measured by monitoring germination of imbibed grains over a three day period at 20° C. Grains were imbibed in petrie dishes with two sheets of filter paper (Whatman No 1, 125 mm) moistened with 10.5 ml of water. Grains were initially imbibed at 4° C. in the dark for periods up to 3 weeks to assist breaking dormancy. Following the pretreatment, the dishes were transferred to 20° C. under continuous light and germination was assessed visually over the next 3 days. The emergence of the coleorhiza from the seed coat was used as the visual marker for germination.

Germination tests on T1 grain from the first eleven rABA8'OH-1 plants (Nos. 1-11) revealed that, after 1 week of imbibition at 4° C. in the dark, many lines had a reduced rate of germination and therefore an increased dormancy compared to the control Golden Promise grains (Table 2). After a further 3 days imbibition at 20° C. in the light, grains of most of the transgenic lines had over 80% germination. Grains of two particular lines (Nos. 7 and 11) were highly dormant, with 25% and 8% germination respectively detected after the 3 day period. Increasing the time of pretreatment at 4° C. in the dark to 14 days assisted in breaking the dormancy of line 7 and 11 grains. After the 14 day pretreatment, the percentage germination after a further 3 days at 20° C. increased to 94 and 71%, respectively (Table 3). These results showed that grains from line 7 and 11 were viable and able to germinate but required a longer treatment of cold and dark to break grain dormancy than the wild-type. Therefore, down-regulation of the expression of HvABA8'OH-1 by an RNA inhibitory molecule was able to modify dormancy in barley.

TABLE 2

Germination of T1 grains of Golden Promise barley and transgenic RNAiHvABA8'OH-1 lines.

| Plant line | Percentage germination after transfer | | | |
|---|---|---|---|---|
| | Day 0 | Day 1 | Day 2 | Day 3 |
| Golden Promise | 94.4 | 100 | 100 | 100 |
| rABA8OH-1a | 11.1 | 72.2 | 88.8 | 88.8 |
| rABA8OH-1b | 8.4 | 80.6 | 94.4 | 97.2 |
| rABA8OH-2a | 66.7 | 91.6 | 94.4 | 94.4 |
| rABA8OH-2b | 66.7 | 94.4 | 97.2 | 100 |
| rABA8OH-3 | 16.6 | 50 | 58.3 | 80.5 |
| rABA8OH-4 | 38.5 | 88.9 | 97.2 | 97.2 |
| rABA8OH-5a | 50 | 88.8 | 94.4 | 94.4 |
| rABA8OH-5b | 22.2 | 97.2 | 97.2 | 97.2 |
| rABA8OH-6a | 63.2 | 91.6 | 94.4 | 94.4 |
| rABA8OH-6b | 70.5 | 94.4 | 100 | 100 |
| rABA8OH-7 | 2.8 | 8.4 | 25 | 25 |
| rABA8OH-8 | 50 | 83.3 | 91.2 | 97.2 |
| rABA8OH-9 | 50 | 91.2 | 100 | 100 |
| rABA80H-10a | 25.6 | 80.5 | 91.5 | 91.5 |
| rABA8OH-10b | 43.1 | 80.5 | 91.7 | 91.7 |
| rABA8OH-11 | 2.8 | 8.3 | 8.3 | 8.3 |

Grain were pre-imbibed for 7 days at 4° C. in the dark before transferring to 20° C. continuous light.

TABLE 3

Germination of grains of Golden Promise barley and transgenic RNAiHvABA8'OH-1 lines.

| Plant line | Percentage germination after transfer | | | |
|---|---|---|---|---|
| | Day 0 | Day 1 | Day 2 | Day 3 |
| Golden Promise-1 | 100 | 100 | 100 | 100 |
| rABA8OH-7 | 74.5 | 88.5 | 91.5 | 94.1 |
| rABA8OH-11 | 57.4 | 62.9 | 65.9 | 71.5 |

The grain were pre-imbibed for 14 days at 4° C. in the dark before transferring to 20° C. continuous light.

As shown in Example 4, reduction in ABA8'OH expression in *Arabidopsis* resulted in higher seed ABA content and dormancy. To examine whether reduction in HvABA8OH-1 expression also resulted in increased ABA content, ABA levels in embryos of T1 grain were measured and compared to those in wild-type Golden Promise embryos. The results, shown graphically in FIG. 11, showed that the two transgenic lines with the highest dormancy, line 7 and 11 embryos had higher ABA contents than the embryos of Golden Promise. Furthermore, the extent of the increase in the ABA levels correlated well with the degree of increased dormancy, showing that an optimal level of dormancy could be attained by choosing a transgenic line with an appropriate level of gene silencing. These results indicated that manipulation of ABA8'OH expression in cereals such as barley also led to changes in ABA content.

Further rABA8'OH-1 transgenic barley plants (Nos. 12-42) were analysed, T1 grains collected from each plant to provide T1 lines, and grain samples analysed for dormancy and ABA levels as described above. The T1 grains from line Nos. 12-42 were tested for changes in dormancy level and ABA content in the embryos compared to grains from (untransformed, wild-type) Golden Promise plants grown side by side with the transgenic lines under the same conditions. Grain dormancy was measured by monitoring germination of imbibed grains over a three day period at 20° C. Many of the lines showed reduced germination rates and therefore increased dormancy. Again, a range was observed for the extent of the increased dormancy. While 95-100% germination was observed for Golden Promise grain, grain of lines 18, 19a, 26a, 34b and 37 exhibited 13-45% germination after 3 days at 20° C.

ABA content was measured by ELISA assays in the embryos of dry grain from these lines. The lines selected for further analysis which had higher dormancy also had higher ABA content in the dry compared with embryos for Golden Promise grains. The ABA levels were increased from 4 ng/embryo for Golden Promise grain to 7-13 ng/embryo for lines 18, 19a, 26a, 34b and 37. Both lines 19a and 37 had more than 10 ng/embryo on average.

To confirm that the increased ABA content and dormancy was a result of reduced HvABA8'OH-1 gene expression, RNA was isolated from embryos from imbibed grains and probed with a radiolabelled DNA probe specific for the HvABA8'OH-1 transcript. For RNA isolation, 20 T1 grain from each line and from Golden Promise were imbibed for 4° C. on moistened filter papers in the dark for 2 days. Fifteen embryos were isolated from the imbibed grains and RNA was extracted using a modified hot-borate method as fully described by Millar et al. (2006). Ten micrograms of RNA from each sample was run on a 1.2% agarose gel containing 2.2M formaldehyde and transferred by capillary transfer to nylon membrane and UV crosslinked. The membranes were prehybridised with a modified Church Buffer (0.5M $Na_2HPO_4$, 7% SDS, 1 mM EDTA and 100 ug/ml denatured salmon sperm DNA at 65° C. for 4 h, and then hybridized overnight at 65° C. with a $^{32}$P-labelled DNA probe (HvABA8'OH-1 3' specific probe). The DNA probe (1144 and 1443 bp) was amplified from the HvABA8'OH-1 cDNA using the following primers 5'-AAGGGCTGGAAAGT-GCTTC-3' (SEQ ID NO:92) and 5'-CTTGCGGGTGAAG-GTCATG-3' (SEQ ID NO:93). The sequence of the HvABA8'OH-1 3' specific probe sequence is provided as SEQ ID NO: 94.

After the overnight hybridisation the blots were washed twice for 30 min with 5% SDS, 1 mM EDTA and 40 mM sodium hydrogen phosphate, followed by more 30 min washes with 1% SDS, 1 mM EDTA and 40 mM sodium hydrogen phosphate. The $^{32}$P signal was monitored using a phosphoimager.

The RNA gel blot analysis showed that HvABA8'OH-1 transcript levels in the imbibed embryos were reduced compared to the level in Golden Promise. The greatest reduction was for line Nos 19a and 37, which were the lines showing the highest levels of ABA per embryo. Therefore, the extent of reduction (silencing) of HvABA8'OH-1 correlated well with the increase in ABA and increased dormancy.

From this data it was predicted that reduction of ABA8'OH-1 gene expression in wheat would also result in increased dormancy and increased ABA content in the wheat grain. Because of the high degree of homology between the wheat and barley ABA8'OH-1 genes, the same hairpin RNA construct, or a corresponding construct made from the wheat cDNAs, can be used to reduce expression of the wheat genes to increase dormancy and prevent pre-harvest sprouting in wheat.

Example 8

Isolation of Wheat cDNAs Encoding TaABA8'OH-1

To isolate wheat genes that were homologous to the barley ABA8'OH genes, PCR primers were designed from the sequence of the 5'UTR of the barley ABA8'OH-1 gene and from within the 3'UTR sequence of a partial wheat EST (CN011303), considered to be a candidate for part of a wheat ABA8'OH gene. The primers were 5'-GTTGCAGGTTG-CAGTAACAGAAC-3' (SEQ ID NO:74) and 5'-GTCGC-CTCTATCGTGCAGTTG-3' (SEQ ID NO:75). First strand cDNA was made from RNA isolated from 6 h imbibed grains (cv. Bob White) and used as the template nucleic acid to amplify the cDNA. Initial attempts to amplify the cDNA were unsuccessful when using an annealing temperature of 65° C., used in the PCR reaction in an attempt to increase specificity. The reaction cycling was: 95° C. for 5 min followed by 35 cycles at 95° C. for 15 s, 65° C. for 15 s and 68° C. for 1.5 min. Reduction of the annealing temperature to 55° C. resulted in amplification of the TaABA8'OH-1 cDNA. These conditions were used to amplify a cDNA sequence which proved to contain the full ORF of the wheat gene designated TaABA8'OH-1.

The sequence of TaABA8'OH-1 cDNA is shown as SEQ ID NO: 8. In the sequence, the 5'UTR corresponded to nucleotide positions 1-21, the protein coding region (ORF) to nucleotides 22-1455 (SEQ ID NO:9), and the 3' UTR to nucleotides 1456-1511. The deduced peptide sequence encoded by the TaABA8'OH-1 cDNA is shown as SEQ ID NO: 10. The wheat EST sequence (Accession No. CN011303) corresponds to nucleotides 810-3' end of SEQ ID NO:8, with 97% nucleotide identity in the overlapping region, however, CN011303 does not encode ABA8'-hydroxylase.

To isolate a genomic clone containing the TaABA8'OH-1 protein coding region, PCR reactions were carried out using same primers and conditions as described above, using genomic DNA isolated from wheat cv. Sunstate as template DNA. The reaction products were analysed on an agarose gel and a 2 kb fragment was gel purified, cloned into pGEM-T Easy (Promega, USA) and sequenced. The genomic fragment contained the complete TaABA8'OH-1 coding region from the D genome (see Example 9). The genomic sequence (FIG. 12) is provided as SEQ ID NO: 11.

Example 9

Methods for Identifying TaABA8'OH-1 Mutants

To set up a screen to identify TaABA8'OH-1 mutations in wheat accession lines, the A, B and D genome homologues of the TaABA8'OH-1 gene were isolated, sequenced and analyzed for DNA polymorphisms as follows. Such polymorphisms could be used to generate genome specific PCR primers as molecular markers. Primers based on wheat EST sequences encoding TaABA8'OH-1 (BE414902, BJ278008, BJ279470 and BE405680) were designed to amplify a fragment of the wheat genomic sequence encoding TaABA8'OH-1.

Using Bob White 26 genomic DNA as template and the primers 5'-GCTCACGTGGATGGTCAAGTTCC-3' (SEQ ID NO:76) and 5'-TTCCCGAACGGCATGAACGTGTTG-3' (SEQ ID NO:77), PCR reactions amplified approximately 770 bp products. The PCR reactions used 1 cycle at 95° C. for 5 min; 35 cycles 95° C., 15 s; 62° C., 15 s; 72° C., 30 s; followed by 1 cycle at 72° C. for 3 min. The products were cloned into pGEMT-EASY and sequenced. Three very similar but distinct groups of sequences were identified and were predicted to represent TaABA8'OH-1 sequences from the A, B and D genomes of wheat. Examples of the three types of PCR-derived sequences were as follows: FGT1880 (SEQ ID NO:14), FGT1886 (SEQ ID NO:13), and FGT1882 (SEQ ID NO:16) (see FIG. 13).

Three primers pairs were designed to selectively amplify a DNA fragment from each sequence type. TaIntron3-23F (5'-TGAGCAGAGCAGAGCATCAATCG-3') (SEQ ID NO:78) and TaIntron3-3R (5'-GTTGCGAGTTTCCCTTGAGT-TAGG-3') (SEQ ID NO:79) amplified sequences from FGT1880. TaIntron3-1F (5'-CAAGGTGAGACATCAAT-CAACTTCG-3') (SEQ ID NO:80) and TaIntron3-1R (5'-GC-GAGTTCGAGTTGGTCTATTCC-3') (SEQ ID NO:81) amplified sequences from FGT1886. TaIntron3-23F (5'-TO-AGCAGAGCAGAGRCATCAATCG-3') (SEQ ID NO:82) and TaIntron3-2R (5'-CGAGTTTGAGTTGGTC-TATTTCGTTC-3') (SEQ ID NO:83) amplified sequences from FGT1882. The reaction conditions using Taq polymerase and 1 cycle at 95° C. for 5 min; 35 cycles 95° C., 15 s; 62° C., 15 s; 72° C., 30 s; followed by 1 cycle at 72° C. for 3 min. Alternative primers could readily be designed, based on the observed differences in the sequences. For example, alternative primers could be for the A genome 5'-CAC CGT AAG TCG CCG TCA TTT CAT G-3' (SEQ ID NO:84) and 5'-CGA TCT CGG CGT GCT CTT CCT GTT G-3' (SEQ ID NO:85), for the B genome 5'-CAA GTT CCT CGG CGA CAA CCC CGC CGT G-3' (SEQ ID NO:86) and 5'-CGG CAT GCT CTT CCT GTT AAT TGT TG-3' (SEQ ID NO:87) and for the D genome, 5'-GTT GCA GGT TGC AGG TAA CAG AAC-3' (SEQ ID NO:88) and 5'-GTC GCC TCT ATC GTG CAG TTG-3' (SEQ ID NO:89).

To establish whether the designed primer pairs were specific for different TaABA8'OH-1 genes on the A, B and D genomes, the primers pairs were tested on nullisomic-tetrasomic lines of wheat (cv. Chinese Spring). Primer pair TaIntron3-23F/TaIntron3-3R were shown to be specific for the TaABA8'OH-1 gene present on the A genome on chromosome 6. Primer pair TaIntron3-1F/TaIntron3-1R were shown to be specific for the TaABA8'OH-1 gene present on the B genome on chromosome 6. Primer pair TaIntron3-23F/TaIntron3-2R were shown to be specific for the TaABA8'OH-1 gene present on the D genome on chromosome 6.

The genome specific primer pairs (TaIntron3-23F/TaIntron3-3R; TaIntron3-1F/TaIntron3-1R; TaIntron3-23F/TaIntron3-2R) were used to screen for mutations such as, for example, deletions in the Ta-ABA8'OH-1 genes in wheat populations. Genomic DNA was isolated from different wheat accession lines from the Tamworth Winter Wheat Collection (NSW Department of Agriculture, Tamworth, NSW, Australia) and screened by PCR for the presence or absence of one or more of the TaABA8'OH-1 regions amplified by the primer pairs. Five TaABA8'OH-1 deletion lines were identified using this PCR screening method.

Using primer TaIntron3-23F/TaIntron3-2R, wheat accession line Aus 1731 (Zonk1) and Aus 14510 (Gandum Garmah) were shown to have a deletion in the D genome copy of the TaABA8'OH-1 gene. Using primers TaIntron3-23F/TaIntron3-3R, wheat accession line Aus 25138 (Shrike) was shown to have a deletion in the A genome copy of the TaABA8'OH-1 gene. Using primers TaIntron3-1F/TaIntron3-1R, wheat accession line Aus 26243 (KS92WGRC18) was shown to have a deletion in the B genome copy of the TaABA8'OH-1 gene. Representative data are shown in FIG. 14 and summarized in Table 4.

TABLE 4

Wheat lines with a deletion in an ABA 8'OH-1 gene.

| Wheat line (*Triticum aestivum*) | Growth habit | Country of origin | ABA8OH-1 deletion (A, B or D genome) |
|---|---|---|---|
| Aus 1731 (Zonk1) | Winter | India | D |
| Aus 5286 | Spring | Iran | D |
| Aus 14510 (Gandum Garmah) | Winter | Afghanistan | D |
| Aus 17683 (New Pusa 201 spelta) | Spring | India | D |
| Aus 14113 (spelta) | Facultative | Iran | D |
| Aus 25138 (Shrike) | Spring? | Australia | A |
| Aus 26243 (KS92WGRC18) | Winter | USA | B |

To demonstrate that other methods such as RFLP hybridization analysis using ABA8'OH gene probes could be used to distinguish the three genes in hexaploid wheat and thereby detect specific mutations, and to further characterize the mutations, genomic DNA from plants of cultivars Sunstate (control), Zonk1, Gandum Garmah, Shrike and KS92WGRC18 wheat lines was digested with HindIII and analysed by Southern blot hybridization. The blot was probed with a barley ABA8'OH-1 Exon4/5 probe and washed under stringent conditions, twice using 2×SSC, 0.1% SDS at 65° C., followed by two washes with 0.5×SSC, 0.1% SDS at 65° C., 20 min per wash.

The autoradiogram is shown in FIG. 15. Comparison of the hydridized bands between Sunstate (control) and the wheat deletion lines revealed that that the band labeled A was derived from the A genome. Shrike which had been shown by PCR to have a deletion of the A genome allele of the TaABAS8'OH-1 gene was missing this band. The band labeled B was missing in KS92WGRC18, confirming that this band was derived from a HindIII fragment from the B genome containing at least part of the TaABA8'OH-1 gene. The D genome band of both Zonk1 and Gandum Garmah appeared to contain a small deletion.

To further characterize the D genome mutations, the region was amplified from wheat lines Zonk1 and Gandum Garmah by PCR using flanking markers (FIG. 16) and the fragment sequenced. Both lines contained a deletion corresponding to nucleotides 1349-1600 of the genomic sequence shown as SEQ ID NO:11 (see also FIG. 12), corresponding to intron 3 and exon 4 of the gene. The two lines may have had a common origin since the deletions were identical. The observation that these two lines contained deletions entirely within the ABA8'OH-1 gene on the D genome, not extending to other, adjacent genes, indicated that these mutations were favourable as null alleles of this gene.

Each of these lines was mutant (null mutant) in one of the three TaABA8'OH-1 genes. To create double or triple null mutants, these lines were crossed to produce the A+B, A+D, B+D and A+B+D null lines, using the PCR screening method to identify progeny containing multiple mutations. These (non-transgenic) wheat lines have reduced ABA8'OH activity in the seed and increased seed dormancy.

To compare the effect of one, two or three mutations, each mutant line was crossed to wild-type, Sunstate. Wheat accession line Aus 1731 (Zonk1) and Aus 14510 (Gandum Garmah) had a deletion in the D genome copy of the TaABA8'OH-1 gene. Wheat accession line Aus 25138 (Shrike) had a deletion in the A genome copy of the TaABA8'OH-1 gene and wheat accession line Aus 26243 (KS92WGRC18) had a deletion in the B genome copy of the TaABA8'OH-1 gene. The resulting F1 plant were grown in a glasshouse. F2 progeny were screened by PCR using the genome specific primer pairs (TaIntron3-23F/TaIntron3-3R; TaIntron3-1F/TaIntron3-1R; TaIntron3-23F/TaIntron3-2R) as described above to identify plants with homozygous deletion alleles.

The dormancy of grains freshly harvested from F2 plants that carried the homozygous allele for the A genome deletion (Sunstate×Aus25138), the homozygous allele for the B genome deletion (Sunstate×Aus26243) and the homozygous allele for the D genome deletion (Sunstate×Aus14510) were compared with grains from Sunstate grown side by side with the deletion lines. Sixty wheat grains were placed on a 15 cm Petrie dish containing 10.5 ml distilled water and two 125 mm Whatman filter papers (No. 1). The grains were pre-imbibed for up to 7 days cold in the dark and then transferred to 20° C. under continuous light for 5 days. Each day grains were scored for germination (emergence of coleorhizae from seedcoat). The results are shown in FIG. 17.

Grains carrying the homozygous allele for the B and D genome deletion had increased dormancy compared to the Sunstate grains. Imbibition of grains carrying B and D genome deletions without any cold treatment resulted in a lower germination after 5 days compared to Sunstate grains. The increased dormancy in the B and D genome deletions could be overcome by pre-imbibing the grains for 4-7 days in the cold and dark before imbibing the grains at 20° C. under light. From these data, it is predicted that combining the A, B and D deletions by crosses will result in even higher levels of dormancy than detected in lines that carry only a single deletion. Identification of mutations in TaABA8'OH-1 gene in the A, B and D genomes provides a non-transgenic avenue to manipulating dormancy in wheat. One approach is to screen for single TaABA8'OH-1 mutations that were already present in wheat populations. Another approach would be to screen populations of mutagenized wheat grain or plants where a mutagen had been used to induce mutations in the wheat genome, for example by TILLING. Such mutations could also be combined by crossing to produce lines that have mutations in two or three TaABA8'OH-1 genes.

Example 10

Construction of Hairpin RNAs and Insertion into Wheat

An alternative approach to using mutations to manipulate dormancy in wheat is to use transgenic approaches using a similar approach to that was used in Example 7. A pSTARLING RNAi-TaABA8'OH-1 construct could be made by using the same primers that were used for amplifying the Exon1/2 region in the HvABA80H-1 gene. We have tested these primers and they also work using $1^{st}$ strand cDNAs made from Chinese Spring wheat grains. As described in Example 7 the sequence of the first primer pair 5'-AAG-GATCCGACTACCACACCCACCTCCGCCGTCTC-3' (SEQ ID NO:69) and 5'-AACCCGGGATCTGGTCGTCG-GTGAGCGCCTC-3' (SEQ ID NO:70). The sequence of the second primer pair was 5'-AAGGTACCGACTACCACAC-CCACCTCCGCCGTCTC-3' (SEQ ID NO:69) and 5'-AAACTAGTATCTGGTCGTCGGTGAGCGCCTC-3' (SEQ ID NO:71). The amplified products can be directionally cloned on either side of the cre intron in the moncot RNAi vector pSTARLING-A using the cloning sites BamHI/SmaI and SpeI/Acc651 creating pSTARLING RNAi-TaABA8'OH-1. Once the construct is made then it can be transformed into wheat using the methods described in Example 1.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

This application claims priority from U.S. 60/729,460, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

References
Ali-Rachedi et al., (2004). *Planta* 219: 479-488.
Almeida and Allshire (2005) *TRENDS Cell Biol* 15: 251-258.
Bourque (1995) *Plant Sci.* 105: 125-149.
Beaudoin et al., (2000). *Plant Cell* 12: 1103-1116.
Bewley (1997). *Plant Cell* 9: 1055-1066.
Brandt et al., (1985) *Carlsberg Res. Commun.* 50: 333-345.
Chang et al., (1993). *Plant Mol Biol Rep* 11: 113-116.
Chiwocha et al., (2005). *Plant J* 42: 35-48.
Clough and Bent (1998). *Plant J* 16: 735-743.
Coen et al., (1990). *Cell* 63: 1311-1322.
Colot et al., (1987) *EMBO J* 6: 3559-3564.

Comai et al., (2004) *Plant J* 37: 778-786.
Cutler and Krochko (1999). *Trends Plant Sci* 4: 472-478.
Eagles et al., (2001) *Aust. J. Agric. Res.* 52:1 349-1356.
Frey et al., (1999). *Plant Mol Biol* 39: 1267-1274.
Ghassemian et al., (2000). *Plant Cell* 12: 1117-1126.
Gleave (1992). *Plant Mol Biol* 20: 1203-1207.
Gubler et al., (2005). *Curr Opin Plant Biol* 8: 183-187.
Grappin et al., (2000). *Planta* 210: 279-285.
Harayama (1998). *Trends Biotechnol* 16: 76-82.
Haseloff and Gerlach (1988) *Nature* 334:585-591.
Helliwell et al., (2001). *Proc Natl Acad Sci USA* 98: 2065-2070.
Henikoff et al. (2004) *Plant Physiol* 135: 630-636.
Himi et al., (2002) *J Exp Bot* 53: 1569-1574.
Iuchi et al., (2001). *Plant J* 27: 325-333.
Jackson (1991) In D J Bowles, S J Gurr, M McPhereson, eds, Molecular Plant Pathology: A Practical approach. Oxford University Press, England. pp 163-174.
Jacobsen et al., (2002). *Physiol Plant* 115: 428-441.
Jager et al., (2005). *Planta* 221: 141-148.
Kato et al., (2001) *Theor Appl Genet* 102: 980-985.
King (1989) In N F Derera, ed, Preharvest Field Sprouting in Cereals. CRC Press Inc, Florida, pp 27-60.
Koornneef et al., (2002). *Curr Opin Plant Biol* 5: 33-36.
Koornneef et al., (2000) In J-D Viémont, J Crabbé, eds, Dormancy in plants: from whole plant behaviour to cellular control. CABI, NY, pp 365-373.
Koornneef et al., (1982). *Theor Appl Genet.* 61: 385-393.
Kushiro et al., (2004). *EMBO J* 23: 1647-1656.
Krochko et al., (1998). *Plant Physiol* 118: 849-860.
Langridge et al., (2001). *Aust J Agric Res* 52: 1043-1077.
Lemieux (2000). *Current Genomics* 1: 301-311.
Li et al. (2004). *Funct Integr Genomics* 4: 84-93.
Mares et al. (2005). *Theor Appl Genet* Epub ahead of print.
Matthews et al., (2001). *Mol. Plant. Breed.* 7: 195-202.
McCarty (1995). *Annu Rev Plant Physiol Plant Mol Biol* 46: 71-93.
McKibbin et al., (2002). *Proc Natl Acad Sci USA* 99: 10203-10208.
Millar et al. (2006) *The Plant J.* 45: 942-954.
Millar and Waterhouse (2005). *Funct Integr Genomics* 5: 129-135.
Mori et al., (2005). *Theor Appl Genet.* 110: 1315-1323.
Needleman and Wunsch (1970) *J. Mol. Biol.* 48:443-453.
Pasquinelli et al., (2005). *Curr Opin Genet Develop* 15: 200-205.
Pellegrineschi et al., (2002). *Genome* 45:421-430.
Perriman et al., (1992) *Gene* 113: 157-163.
Pompon et al., (1996). *Methods Enzymol* 272: 51-64.
Prada et al. (2004). *Theor Appl Genet.* 109: 62-70.
Qin and Zeevaart (1999). *Proc Natl Acad Sci USA* 96: 15354-15361.
Qin and Zeevaart (2002). *Plant Physiol* 128: 544-551.
Saito et al., (2004). *Plant Physiol* 134: 1439-1449.
Schwartz et al., (1997). *Science* 276: 1872-1874.
Senior (1998) *Biotech. Genet. Engin. Revs.* 15: 79-119.
Seo and Koshiba (2002). *Trends Plant Sci* 7: 41-48.
Sharp et al., (2001) *Aust J Agric Res* 52: 1357-1366.
Shippy et al., (1999) *Mol. Biotech.* 12: 117-129.
Slade and Knauf (2005). *Transgenic Res* 14: 109-115.
Smith et al., (2000) *Nature* 407: 319-320.
Stefanov et al., (1991) *Acta Biologica Hungarica* 42:323-330.
Symons et al., (2002). *Physiol Plant* 116: 389-397.
Tingay et al., (1997). *Plant J* 11: 1369-1376.
Thompson et al., (2000). *Plant J* 23: 363-374.
Wan and Lemaux (1994). *Plant Physiol.* 104:37-48.
Wan and Wilkins (1994). *Anal Biochem* 223: 7-12.
Wang et al., (1995). *Planta* 195: 586-592.
Wang et al., (1998). *Acta Hort.* 461: 401-405.
Waterhouse et al., (1998). *Proc. Natl. Acad. Sci. USA* 95: 13959-13964.
Zhou et al., (2004). *Plant Physiol* 134: 361-369.

---

The invention claimed is:

1. A wheat plant which has a genetic variation that decreases ABA 8'-hydroxylase activity in the grain of the wheat plant, wherein said genetic variation comprises two mutations of which one mutation is in a first ABA 8'-hydroxylase-1 gene and one mutation is in a second ABA 8'-hydroxylase-1 gene of the plant, wherein the mutations are in the A and B genomes, the A and D genomes or the B and D genomes of the wheat plant, such that the ABA 8'-hydroxylase activity is decreased in the grain of the plant and the grain of the plant has a rate of germination that is decreased relative to grain of a corresponding wheat plant which does not have the genetic variation.

2. The wheat plant of claim 1, wherein the wheat plant is homozygous for the mutations in each of the two ABA 8'-hydroxylase-1 genes.

3. The wheat plant of claim 1, wherein the two mutations are in the A and B genomes of the wheat plant.

4. The wheat plant of claim 1, wherein the two mutations are in the A and D genomes of the wheat plant.

5. The wheat plant of claim 1, wherein the two mutations are in the B and D genomes of the wheat plant.

6. The wheat plant of claim 1, wherein the genetic variation includes a mutation in the ABA 8'-hydroxylase-1 gene in the D genome of the wheat plant.

7. The wheat plant of claim 1, wherein the dormancy of grain of the plant is increased relative to the grain of the corresponding wheat plant which does not have the genetic variation.

8. The wheat plant of claim 1, wherein the rate of germination of the grain is decreased such that less than 90% of the grain germinate within seven days after the beginning of imbibition.

9. The wheat plant of claim 1, wherein the genetic variation is in two ABA 8'-hydroxylase-1 genes, and the genetic variation further comprises a third mutation which is in a third ABA 8'-hydroxylase-1 gene of the plant, wherein two of the ABA 8'-hydroxylase-1 genes are preferentially expressed in the coleorhizae of germinating grain.

10. The wheat plant of claim 1, wherein the ABA 8'-hydroxylase activity is decreased in at least the developing grain, the mature grain, or the grain following imbibition.

11. The wheat plant of claim 1 which is a hexaploid wheat plant which has a mutation in a first ABA 8'-hydroxylase-1 gene, a mutation in a second ABA 8-hydroxylase-1 gene, and a mutation in a third ABA 8'-hydroxylase-1 gene, wherein each mutation decreases ABA 8'-hydroxylase activity in the grain of the wheat plant.

12. A method of producing seed, the method comprising:
a) growing the wheat plant of claim 1, and
b) harvesting the seed.

13. A seed of the wheat plant of claim 1, comprising the genetic variation.

14. A method of producing flour, wholemeal, starch or other product obtained from seed, the method comprising;
a) obtaining seed according to claim 13, and
b) producing the flour, wholemeal, starch or other product.

15. A method of preparing a food product, the method comprising mixing the seed of claim 13, or flour, wholemeal or starch produced from said seed, with a food ingredient.

* * * * *

SEQUENCE LISTING

```
<160> NUMBER OF SEQ ID NOS: 94

<210> SEQ ID NO 1
<211> LENGTH: 3190
<212> TYPE: DNA
<213> ORGANISM: Hordeum vulgare

<400> SEQUENCE: 1
ccggttgatt ttaatatttt tcgaaaattt aagacacgga ggtgcatgct cgcgacaatt      60
tccttgacga cggaccaaaa ggtcagttca acacctgtca ttccgcatgc attcctactg     120
aacggctgct ttaaaccgtt cagtgtttca cccccaagaa tcacgtagag aatgactcac     180
attagtctta gacggaacga agaatgagag gacataaata accggcccaa tcagtagaca     240
tgcgggccaa tgaaaatatc tggaggccaa ctgagctagt gctacgtgac gatgccgtgg     300
ccaggccagg aggacggggc tgggatatta taggagaggg aagagtatat atctgagtaa     360
tcaatcgagc atgcggccaa atgctacagc agaattacag gagagggaag catcagtcgt     420
ctcgtacgag agcgtgtgca gcgctgagag gagacgggac gtgggccgaa agagagatgg     480
atgggtgagc tgttggtgtt gcgacctccc gcgctggaaa gctggactgg actggactgg     540
actgcgtgga ttgggcaatt gattagtggc tcggtccagc tcttgcccga ttaaactgcg     600
caataattcg ctgagcctca cagctcctag tttagtttag atctttaggc aggggccggg     660
```

```
agaccggcaa cgaggagaga gcgggagcgg cgcatcaccg ccaatctata aatacctgcc    720
acgccgctcg catttccctc cacacccagg caccaccaac ccaccaccca tctcccctcc    780
tctcctcctc gtcttcctcc ttcgggcctc cgttgcaggt tgcaggtaac agaaccgaag    840
aaatcctttt ggaatgggtg ccttcatcct cctcctctgc ttgctcgtgc cgttggtgct    900
cgtgtgcgcc gtccgcgcca ggaagggcgc cggcgggcgg tcgtcgtcgg gcggcggcaa    960
gaagggcagg ctgccgccgg ggtccatggg gtggccgtac gtgggcgaga ccacgcagct   1020
ctactcctcc aagaaccccca acgtcttctt cgccaggaag cgtaacaagt acggcccat   1080 cttcaagacg cacatcctcg ggtgccctg cgtcatggtg tccagcccgg aggccgccaa   1140
gttcgtgctc gtcacgcagg cgcacctctt caagcctacc ttcccggcca gcaaggagcg   1200
gatgctgggc cgccaggcca tcttcttcca gcaggggac taccacaccc acctccgccg   1260
tctcgtctcc cgcgccttct cccccgaggc catccgcggc tccgtctcat ccatcgaggc   1320
catcgccctc cgctccctcg gctcatggga aggccatgaa gtcaacacct tccaagaaat   1380
gaagactgta agttcttctt cttcttccat tcctgcctcc tctgttttca tctgctctgc   1440
tctgctctgc ggctaaatgc ttagaaatgg tcactgatgg ttttgttggt gtcattgcgc   1500
agtacgctct gaatgtggca ttgctgtcca tcttcgggga ggaggagatg cagtacatcg   1560
aggagctgaa gcagtgctac ctgacgcgtgg agaaggggta caactcgatg ccggtgaacc   1620
tgccgggcac gctgttccac aaggccatga aggcccggaa gcggctgggc gccattgtgg   1680
cccacatcat ctcagcccgg cgcgagcggg agcgcgggag cgacctcctg ggctccttca   1740
tggacggccg cgaggcgctc accgacgacc agatcgccga caacgccatc ggcgtcatct   1800
tcgccgcgcg ggacaccacc gccagcgtgc tcacgtggat ggtcaagttc ctcggcgaca   1860
accccgccgt cctcaaagcc gtcaccgtaa gtcgccatca aaccgaccag ctgacccgct   1920
ttggcacccc ggcatgtcga aaggcagtgt ctctgacccg cgcgcgtgaa acgattgaca   1980
acaggaagag cacgccgaga tcgcgaggga gaaggcgttg tccggcgagc cgctgtcgtg   2040
ggcagacacg cggcggatgc gggtgacggg ccgggtgatc caggagacga tgcgggtggc   2100
gtccatcctc tccttcacct tcagagaggc cgtcgaggac gtggagtacc aaggtgagca   2160
ctgagctctg agcagagaca tcaatcaact tcgctttggt cgtttgcggc agcgcactgc   2220
tgtaccgtgc tgtacctctc ggagtacagc tacagcagtg cgctgcctgc gcatgaactg   2280
gctcggaaag gacgtgctcc taaccgaacg gacgaaatag accaacaact cgaactcgca   2340
actcacctcg gctcggctcg ctcctccgtg cagggtacct gatccccaag ggctggaaag   2400
tgcttcccct gttccggaac atccaccaca accccgacca cttcccctcc ccgaaaagt   2460 tcgatccttc acgattcgag gtcagcatca tcacatcttc ttcttctact gtttttttttt   2520 tccttggatg atgatgatga taggcttgag agtcccccgt tgttcattag ctgattgcgt   2580
ttttgttctt ggtgactgca ggtggccccc aagcccaaca cgttcatgcc gttcgggaac   2640
gggacccact cgtgccccgg caacgagctg ccaagctgg agatgctcgt cctctgccac   2700
cacctcgcca ccaagtacag atggtctacc tccagtccg agagcggcgt gcagttcggc   2760
cccttcgccc tgcccatcaa cggcctcccc atgaccttca cccgcaaggc tgatctatgt   2820
cttcctcctt cggaaaatca acagcacgat agaggcaacg cgtgtggcca tgcgaaccgg   2880
atcggttctc catccgtcag tgtccgtgcc ggtcgccgtc ggaggggaca cttgtagcgg   2940
tgggcgccgc ggcgggagct ggcgatggat cggatcggag cacggaccgt caaagtcctt   3000
tgtacagatt cttcttcagc taggaccatg acggccgggc gagacaagac caggaaaaaa   3060
```

```
ttcctgccct tcacaaacac acaccagtca gtggtagcac tacgtaggca ttctcagcta    3120
gggagatccg gcgccacaaa gaagtggcgc ccaactgtaa aaccaaccat tttttatcct    3180
tttctttcag                                                          3190

<210> SEQ ID NO 2
<211> LENGTH: 1541
<212> TYPE: DNA
<213> ORGANISM: Hordeum vulgare

<400> SEQUENCE: 2
gttgcaggtt gcaggtaaca gaaccgaaga atccttttg gaatgggtgc cttcatcctc      60
ctcctctgct tgctcgtgcc gttggtgctc gtgtgcgccg tccgcgccag gaagggcgcc    120
ggcgggcggt cgtcgtcggg cggcggcaag aagggcaggc tgccgccggg gtccatgggg    180
tggccgtacg tgggcgagac cacgcagctc tactcctcca agaacccaa cgtcttcttc    240 gccaggaagc gtaacaagta cgggcccatc ttcaagacgc acatcctcgg gtgccctgc    300 gtcatggtgt ccagcccgga ggccgccaag ttcgtgctcg tcacgcaggc gcacctcttc    360
aagcctacct ccccggccag caaggagcgg atgctgggcc gccaggccat cttcttccag    420 caggggact accacaccca cctccgccgt ctcgtctccc gcgccttctc ccccgaggcc    480
atccgcggct ccgtttcctc catcgaggcc atcgccctcc gctccctcgg ctcatgggaa    540
ggccatgaag tcaacacctt ccaagaaatg aagacttacg ctctgaatgt ggcattgctg    600
tccatcttcg gggaggagga gatgcagtac atcgaggagc tgaagcagtg ctacctgacg    660
ctggagaagg ggtacaactc gatgccggtg aacctgccgg gcacgctgtt ccacaaggcc    720
atgaaggccc ggaagcggct gggcgccatt gtggcccaca tcatctcagc ccggcgcgag    780
cgggagcgcg ggagcgacct cctgggctcc ttcatggacg gccgcgaggc gctcaccgac    840
gaccagatcg ccgacaacgc catcggcgtc atcttcgccg cgcgggacac caccgccagc    900
gtgctcacgt ggatggtcaa gttcctcggc gacaaccccg ccgtcctcaa agccgtcacc    960
gaagagcacg ccgagatcgc gagggagaag gcgttgtccg gcgagccgct gtcgtgggcc    1020
gacacgcggc ggatgcgggt gacgggccgg gtgatccagg agacgatgcg ggtggcgtcc    1080
atcctctcct tcaccttcag agaggccgtc gaggacgtgg agtaccaagg gtacctgatc    1140
cccaagggct ggaaagtgct tcccctgttc cggaacatcc accacaaccc cgaccacttc    1200
ccctcccccg aaaagttcga tccttcacga ttcgaggtgg cccccaagcc caacacgttc    1260
atgccgttcg ggaacgggac ccactcgtgc cccggcaacg agctggccaa gctggagatg    1320
ctcgtcctct gccaccacct cgccaccaag tacagatggt ctacctccaa gtccgagagc    1380
ggcgtgcagt tcggcccctt cgccctgccc atcaacggcc tccccatgac cttcacccgc    1440
aaggcctgat ctatgtcttc ctccttcgga aaatcaacac cacgatagag gcaacggcgt    1500
ggcgcatgcg aaccggatcg gttctccatc cgtcagtgtc c                       1541

<210> SEQ ID NO 3
<211> LENGTH: 1404
<212> TYPE: DNA
<213> ORGANISM: Hordeum vulgare

<400> SEQUENCE: 3
atgggtgcct tcatcctcct cctctgcttg ctcgtgccgt tggtgctcgt gtgcgccgtc     60
cgcgccagga gggcgccgg cgggcggtcg tcgtcgggcg gcggcaagaa gggcaggctg    120
ccgccggggt ccatggggtg gccgtacgtg ggcgagacca cgcagctcta ctcctccaag    180
```

```
aaccccaacg tcttcttcgc caggaagcgt aacaagtacg ggcccatctt caagacgcac    240
atcctcgggt gcccctgcgt catggtgtcc agcccggagg ccgccaagtt cgtgctcgtc    300
acgcaggcgc acctcttcaa gcctaccttc ccggccagca aggagcggat gctgggccgc    360
caggccatct tcttccagca gggggactac cacacccacc tccgccgtct cgtctcccgc    420
gccttctccc ccgaggccat ccgcggctcc gtttcctcca tcgaggccat cgccctccgc    480
tccctcggct catgggaagg ccatgaagtc aacaccttcc aagaaatgaa gacttacgct    540
ctgaatgtgg cattgctgtc catcttcggg gaggaggaga tgcagtacat cgaggagctg    600
aagcagtgct acctgacgct ggagaagggg tacaactcga tgccggtgaa cctgccgggc    660
acgctgttcc acaaggccat gaaggcccgg aagcggctgg cgccattgt ggcccacatc     720 atctcagccc ggcgcgagcg ggagcgcggg agcgacctcc tgggctcctt catggacggc    780
cgcgaggcgc tcaccgacga ccagatcgcc gacaacgcca tcggcgtcat cttcgccgcg    840
cgggacacca ccgccagcgt gctcacgtgg atggtcaagt tcctcggcga caaccccgcc    900
gtcctcaaag ccgtcaccga agagcacgcc gagatcgcga gggagaaggc gttgtccggc    960
gagccgctgt cgtgggccga cacgcggcgg atgcgggtga cgggccgggt gatccaggag   1020
acgatgcggg tggcgtccat cctctccttc accttcagag aggccgtcga ggacgtggag   1080
taccaagggt acctgatccc caagggctgg aaagtgcttc ccctgttccg gaacatccac   1140
cacaaccccg accacttccc ctcccccgaa aagttcgatc cttcacgatt cgaggtggcc   1200
cccaagccca cacgttcat gccgttcggg aacgggaccc actcgtgccc cggcaacgag   1260
ctggccaagc tggagatgct cgtcctctgc caccacctcg ccaccaagta cagatggtct   1320
acctccaagt ccgagagcgg cgtgcagttc ggccccttcg ccctgcccat caacggcctc   1380
cccatgacct tcacccgcaa ggcc                                          1404
```

<210> SEQ ID NO 4
<211> LENGTH: 468
<212> TYPE: PRT
<213> ORGANISM: Hordeum vulgare

<400> SEQUENCE: 4

```
Met Gly Ala Phe Ile Leu Leu Cys Leu Leu Val Pro Leu Val Leu
1               5                   10                  15

Val Cys Ala Val Arg Ala Arg Lys Gly Ala Gly Gly Arg Ser Ser
                20                  25                  30

Gly Gly Gly Lys Lys Gly Arg Leu Pro Pro Gly Ser Met Gly Trp Pro
            35                  40                  45

Tyr Val Gly Glu Thr Thr Gln Leu Tyr Ser Ser Lys Asn Pro Asn Val
        50                  55                  60

Phe Phe Ala Arg Lys Arg Asn Lys Tyr Gly Pro Ile Phe Lys Thr His
65                  70                  75                  80

Ile Leu Gly Cys Pro Cys Val Met Val Ser Pro Glu Ala Ala Lys
                85                  90                  95

Phe Val Leu Val Thr Gln Ala His Leu Phe Lys Pro Thr Phe Pro Ala
            100                 105                 110

Ser Lys Glu Arg Met Leu Gly Arg Gln Ala Ile Phe Gln Gln Gly
        115                 120                 125

Asp Tyr His Thr His Leu Arg Arg Leu Val Ser Arg Ala Phe Ser Pro
    130                 135                 140

Glu Ala Ile Arg Gly Ser Val Ser Ser Ile Glu Ala Ile Ala Leu Arg
145                 150                 155                 160
```

```
Ser Leu Gly Ser Trp Glu Gly His Glu Val Asn Thr Phe Gln Glu Met
            165                 170                 175
Lys Thr Tyr Ala Leu Asn Val Ala Leu Leu Ser Ile Phe Gly Glu Glu
            180                 185                 190
Glu Met Gln Tyr Ile Glu Glu Leu Lys Gln Cys Tyr Leu Thr Leu Glu
            195                 200                 205
Lys Gly Tyr Asn Ser Met Pro Val Asn Leu Pro Gly Thr Leu Phe His
210                 215                 220
Lys Ala Met Lys Ala Arg Lys Arg Leu Gly Ala Ile Val Ala His Ile
225                 230                 235                 240
Ile Ser Ala Arg Arg Glu Arg Glu Arg Gly Ser Asp Leu Leu Gly Ser
            245                 250                 255
Phe Met Asp Gly Arg Glu Ala Leu Thr Asp Asp Gln Ile Ala Asp Asn
            260                 265                 270
Ala Ile Gly Val Ile Phe Ala Ala Arg Asp Thr Thr Ala Ser Val Leu
            275                 280                 285
Thr Trp Met Val Lys Phe Leu Gly Asp Asn Pro Ala Val Leu Lys Ala
            290                 295                 300
Val Thr Glu Glu His Ala Glu Ile Ala Arg Glu Lys Ala Leu Ser Gly
305                 310                 315                 320
Glu Pro Leu Ser Trp Ala Asp Thr Arg Arg Met Arg Val Thr Gly Arg
            325                 330                 335
Val Ile Gln Glu Thr Met Arg Val Ala Ser Ile Leu Ser Phe Thr Phe
            340                 345                 350
Arg Glu Ala Val Glu Asp Val Glu Tyr Gln Gly Tyr Leu Ile Pro Lys
            355                 360                 365
Gly Trp Lys Val Leu Pro Leu Phe Arg Asn Ile His His Asn Pro Asp
            370                 375                 380
His Phe Pro Ser Pro Glu Lys Phe Asp Pro Ser Arg Phe Glu Val Ala
385                 390                 395                 400
Pro Lys Pro Asn Thr Phe Met Pro Phe Gly Asn Gly Thr His Ser Cys
            405                 410                 415
Pro Gly Asn Glu Leu Ala Lys Leu Glu Met Leu Val Leu Cys His His
            420                 425                 430
Leu Ala Thr Lys Tyr Arg Trp Ser Thr Ser Lys Ser Glu Ser Gly Val
            435                 440                 445
Gln Phe Gly Pro Phe Ala Leu Pro Ile Asn Gly Leu Pro Met Thr Phe
450                 455                 460
Thr Arg Lys Ala
465

<210> SEQ ID NO 5
<211> LENGTH: 1567
<212> TYPE: DNA
<213> ORGANISM: Hordeum vulgare

<400> SEQUENCE: 5
acctcgctgg tctgagtgat ccttctcaag gatcatttgg attggatggc cttcttcctc      60
ctcctgtgca tcctcgtctc tgtggccatc gtgtcctacg ccaccacgc aatccggcgg      120 aggcgccagg gctgcgctca tggccgtcat gagcaggccg ccctcaagct gccccccggc      180
tccatgggcc tgccttacgt cggcgagacc ctgcagctct actcccagga ccccagcgtc      240
ttcctctcct ccaagcagaa gcggtacggg gagatcttca gacgcacct cctggggtgc      300 ccgtgcgtga tgctggcgag cccggaggcg gcgcgcttcg tgctggtgtc gcgggcccac      360
```

```
ctcttcaagc cgacgtaccc gcggagcaag gagcgcctca tcggcccgtc ggcgctcttc      420
ttccaccagg gcgactacca cctccgcctc cgccggctcg tccagggccc gctcggcccc      480
gaggccctgc gcaagctcgt gccggacatc gaggccgccg ttcgctccac gctcgccgcc      540
tgggcggacg gcgacgtcgc cagcactttc cacgccatga agaggctctc gttcgacgtc      600
ggcatcgtga cgatcttcgg cgggcggctg gacgagcggc ggaaggagga gctcaggcgg      660
aactacgccg tcgtggagaa aggctacaac tccttcccca acagcttccc cgggacgcta      720
tactacaagg cgatccaggc gaggcggcgg ctgaacggcg tgctgagcga cgtcgtgcac      780
gagcgtaggg agcggggcga gcacggcgac gacctcctcg gctgcctcat gcggtcgcgg      840
gccggcggcg acgacgccga cgacgagggc gcgctgctga cggacgagca ggtcgccgac      900
aacgtcatcg gcgtgctgtt cgcggcgcag gacacgacgg ccagcgtgct cacctggatc      960
gtcaagtacc tccacgaccg cccgaagctg ctcgaggccg tcagggcgga gcacgcggcg     1020
atccacgagg ccaacgacgg cgggaggcgg ccgctgacat gggcgcagac gaggagcatg     1080
acgctgacgc acagggtgat tttggagagc ctaaggatgg ccagcatcat ctccttcacg     1140
ttcagggagg ccgtggccga cgtggagtac aaagggtttc ttatcccaa ggggtggaag      1200 gtgatgccgc tcttcaggaa catccatcac agcccggact acttccagga tccacacaag     1260 ttcgacccctt cgcgattcaa ggtggcgccg cggccgaaca ccttcacgcc gttcgggagc     1320
ggggtgcacg cgtgcccggg gaacgagctg ccaagctcg agatgctggt gctcatccac      1380
cacctggtca ccggctacag gtgggaggtt gttggatcga cgacgacgt cgagtacagc      1440 ccattccccg ttccccgcca tggcctgctc gccagggtac ggcgagatga cggcgtctgc     1500
gcgggtagga aggggtgccc gactgatgaa gatgacaact acgacgacga cgaagtgata     1560
gtgtgac                                                               1567
```

<210> SEQ ID NO 6
<211> LENGTH: 1518
<212> TYPE: DNA
<213> ORGANISM: Hordeum vulgare

<400> SEQUENCE: 6

```
atggccttct tcctcctcct gtgcatcctc gtctctgtgg ccatcgtgtc ctacgcccac       60
cacgcaatcc ggcggaggcg ccagggctgc gctcatggcc gtcatgagca ggccgccctc      120
aagctgcccc ccggctccat gggcctgcct tacgtcggcg agaccctgca gctctactcc      180
caggacccca gcgtcttcct ctcctccaag cagaagcggt acggcgagat cttcaagacg      240
cacctcctgg ggtgcccgtg cgtgatgctg gcgagcccgg aggcggcgcg cttcgtgctg      300
gtgtcgcggg cccacctctt caagccgacg taccgcgga gcaaggagcg cctcatcggc       360
ccgtcggcgc tcttcttcca ccagggcgac taccacctcc gcctccgccg gctcgtccag      420
ggcccgctcg gccccgaggc cctgcgcaag ctcgtgccgg acatcgaggc cgccgttcgc      480
tccacgctcg ccgcctgggc ggacggcgac gtcgccagca ctttccacgc catgaagagg      540
ctctcgttcg acgtcggcat cgtgacgatc ttcggcgggc ggctgacga cggcggaag       600 gaggagctca ggcggaacta cgccgtcgtg gagaaaggct acaactcctt ccccaacagc      660
ttccccggga cgctatacta caaggcgatc caggcgaggc ggcggctgaa cggcgtgctg      720
agcgacgtcg tgcacgagcg tagggagcgg ggcgagcacg gcgacgacct cctcggctgc      780
ctcatgcggt cgcggccgg cggcgacgac gccgacgacg agggcgcgct gctgacggac      840
gagcaggtcg ccgacaacgt catcggcgtg ctgttcgcgg cgcaggacac gacggccagc      900
```

-continued

```
gtgctcacct ggatcgtcaa gtacctccac gaccgcccga agctgctcga ggccgtcagg     960
gcggagcacg cggcgatcca cgaggccaac gacggcggga ggcggccgct gacatgggcg    1020
cagacgagga gcatgacgct gacgcacagg gtgattttgg agagcctaag gatggccagc    1080
atcatctcct tcacgttcag ggaggccgtg gccgacgtgg agtacaaagg gtttcttatc    1140 cccaagggt ggaaggtgat gccgctcttc aggaacatcc atcacagccc ggactacttc     1200
caggatccac acaagttcga cccttcgcga ttcaaggtgg cgccgcggcc gaacaccttc    1260
acgccgttcg ggagcggggt gcacgcgtgc ccggggaacg agctggccaa gctcgagatg    1320
ctggtgctca tccaccacct ggtcaccggc tacaggtggg aggttgttgg atcgagcgac    1380
gacgtcgagt acagcccatt ccccgttccc cgccatggcc tgctcgccag gtacggcga    1440 gatgacggcg tctgcgcggg taggaagggg tgcccgactg atgaagatga caactacgac    1500
gacgacgaag tgatagtg                                                  1518
```

<210> SEQ ID NO 7
<211> LENGTH: 506
<212> TYPE: PRT
<213> ORGANISM: Hordeum vulgare

<400> SEQUENCE: 7

```
Met Ala Phe Phe Leu Leu Cys Ile Leu Val Ser Val Ala Ile Val
1               5                   10                  15

Ser Tyr Ala His His Ala Ile Arg Arg Arg Gln Gly Cys Ala His
                20                  25                  30

Gly Arg His Glu Gln Ala Ala Leu Lys Leu Pro Pro Gly Ser Met Gly
            35                  40                  45

Leu Pro Tyr Val Gly Glu Thr Leu Gln Leu Tyr Ser Gln Asp Pro Ser
        50                  55                  60

Val Phe Leu Ser Ser Lys Gln Lys Arg Tyr Gly Glu Ile Phe Lys Thr
65                  70                  75                  80

His Leu Leu Gly Cys Pro Cys Val Met Leu Ala Ser Pro Glu Ala Ala
                85                  90                  95

Arg Phe Val Leu Val Ser Arg Ala His Leu Phe Lys Pro Thr Tyr Pro
            100                 105                 110

Arg Ser Lys Glu Arg Leu Ile Gly Pro Ser Ala Leu Phe Phe His Gln
        115                 120                 125

Gly Asp Tyr His Leu Arg Leu Arg Arg Leu Val Gln Gly Pro Leu Gly
    130                 135                 140

Pro Glu Ala Leu Arg Lys Leu Val Pro Asp Ile Glu Ala Ala Val Arg
145                 150                 155                 160

Ser Thr Leu Ala Ala Trp Ala Asp Gly Asp Val Ala Ser Thr Phe His
                165                 170                 175

Ala Met Lys Arg Leu Ser Phe Asp Val Gly Ile Val Thr Ile Phe Gly
            180                 185                 190

Gly Arg Leu Asp Glu Arg Arg Lys Glu Glu Leu Arg Arg Asn Tyr Ala
        195                 200                 205

Val Val Glu Lys Gly Tyr Asn Ser Phe Pro Asn Ser Phe Pro Gly Thr
    210                 215                 220

Leu Tyr Tyr Lys Ala Ile Gln Ala Arg Arg Leu Asn Gly Val Leu
225                 230                 235                 240

Ser Asp Val Val His Glu Arg Arg Glu Arg Gly Glu His Gly Asp Asp
                245                 250                 255

Leu Leu Gly Cys Leu Met Arg Ser Arg Ala Gly Gly Asp Asp Ala Asp
```

```
                260                 265                 270
Asp Glu Gly Ala Leu Leu Thr Asp Glu Gln Val Ala Asp Asn Val Ile
                275                 280                 285
Gly Val Leu Phe Ala Ala Gln Asp Thr Thr Ala Ser Val Leu Thr Trp
            290                 295                 300
Ile Val Lys Tyr Leu His Asp Arg Pro Lys Leu Leu Glu Ala Val Arg
305                 310                 315                 320
Ala Glu His Ala Ala Ile His Glu Ala Asn Asp Gly Gly Arg Arg Pro
                325                 330                 335
Leu Thr Trp Ala Gln Thr Arg Ser Met Thr Leu Thr His Arg Val Ile
            340                 345                 350
Leu Glu Ser Leu Arg Met Ala Ser Ile Ile Ser Phe Thr Phe Arg Glu
                355                 360                 365
Ala Val Ala Asp Val Glu Tyr Lys Gly Phe Leu Ile Pro Lys Gly Trp
        370                 375                 380
Lys Val Met Pro Leu Phe Arg Asn Ile His His Ser Pro Asp Tyr Phe
385                 390                 395                 400
Gln Asp Pro His Lys Phe Asp Pro Ser Arg Phe Lys Val Ala Pro Arg
                405                 410                 415
Pro Asn Thr Phe Thr Pro Phe Gly Ser Gly Val His Ala Cys Pro Gly
            420                 425                 430
Asn Glu Leu Ala Lys Leu Glu Met Leu Val Leu Ile His Leu Val
                435                 440                 445
Thr Gly Tyr Arg Trp Glu Val Val Gly Ser Ser Asp Asp Val Glu Tyr
        450                 455                 460
Ser Pro Phe Pro Val Pro Arg His Gly Leu Leu Ala Arg Val Arg Arg
465                 470                 475                 480
Asp Asp Gly Val Cys Ala Gly Arg Lys Gly Cys Pro Thr Asp Glu Asp
                485                 490                 495
Asp Asn Tyr Asp Asp Glu Val Ile Val
                500                 505

<210> SEQ ID NO 8
<211> LENGTH: 1511
<212> TYPE: DNA
<213> ORGANISM: Triticum aestivum

<400> SEQUENCE: 8
cgaagaaagc ctttcgctga catggctgct ttcatcctct tcctctgctt gctcgtgccg      60
ctcgtcctcg cgtgcgccgt ccgcgccagg aagggcgccg ccgggcgggc gtcgtcgggc     120
ggcggcggca aaagggcgg caccagcctg ccgctgccgc cggggtcgat ggggtggccg     180
tacgtgggcg agaccacgca gctctactcc tccaagaacc ccaacgtctt cttcgccagg     240
aagcgggaca gtacgggcc atcttcaag acgcacatcc tcgggtgccc ctgcgtcatg     300
gtgtccagcc cggaggccgc caagttcgtg ctcgtcactc aggcgcacct cttcaagcct     360
accttcccgg ccagcaagga gcggatgctg ggccccagg ccatcttctt ccagcagggg     420
gactaccatg cccacctccg ccgtctcgtc tcacgcgcct ctctcccga ggccatccgc     480 ggttccgtcc ctgccatcga ggctatcgcc ctccgctccc tcggctcctg ggaagacctg     540
caagtcaaca ccttccaaga gatgaagact tacgctctga atgtggcatt gctgtccatc     600
ttcggcgagg aggagatgca gtacatcgag gagctgaagc agtgctacct gacgctggag     660 aagggggtaca actcgatgcc ggtgaacctg ccgggcacgc tgttccacaa ggccatgaag     720
gcccgaaagc ggctgggcgc cattgtggcc cacatcatct cggcccggcg cgagcgcgag     780
```

```
cgcgggagcg acctcctggg ctccttcaag gacggccgcg aggcgctcac cgacgaccag    840
atcgccgaca acgccatcgg cgtcatcttc gccgcgcgcg acaccaccgc cagcgtgctc    900
acgtggatgg tcaagttcct cggcgacaac ccgccgtcc tcaaagccgt caccgaagag    960
cacgctgaga tcgcgaggga aaggcgttg tccggcgagc cactgtcgtg ggccgacacg    1020
cggcggatgc ggatgacggg ccgggtgatc caggagacga tgcgggtggc gtccatcctc    1080
tccttcacct tcagggaggc cgtggaggac gtggagtacc aagggtacct gattcccaag    1140
ggctggaaag tgcttcccct gctccggaac atccaccaca accccgacca cttcccctcc    1200
cctgaaaagt tcgatccttc acgattcgag gtggccccca agcccaacac gttcatgccg    1260
ttcgggaacg ggacccactc gtgccccggc aacgagctgg ccaagctgga gatgctcgtc    1320
ctctgccacc acctcgccac caagtacaga tggtccacct ccaagtccga gagcggcgtc    1380
cagttcggcc ccttcgccct ccccatcaac ggcctcccca tgaccttcac ccgcaaggac    1440
gacaagaaca aagcctgagc catccatcca tccacccatc catcgcctcc tcctcgttcc    1500
caaagggaaa t                                                        1511

<210> SEQ ID NO 9
<211> LENGTH: 1434
<212> TYPE: DNA
<213> ORGANISM: Triticum aestivum

<400> SEQUENCE: 9
atggctgctt tcatcctctt cctctgcttg ctcgtgccgc tcgtcctcgc gtgcgccgtc     60
cgcgccagga agggcgccgc cgggcgggcg tcgtcgggcg gcggcggcaa aaagggcggc    120
accagcctgc cgctgccgcc ggggtcgatg gggtggccgt acgtgggcga gaccacgcag    180
ctctactcct ccaagaaccc caacgtcttc ttcgccagga gcgggacaa gtacgggccc    240 atcttcaaga cgcacatcct cgggtgcccc tgcgtcatgg tgtccagccc ggaggccgcc    300
aagttcgtgc tcgtcactca ggcgcacctc ttcaagccta ccttcccggc cagcaaggag    360
cggatgctgg cccccaggc catcttcttc agcaggggg actaccatgc ccacctccgc    420
cgtctcgtct cacgcgcctt ctctcccgag gccatccgcg gttccgtccc tgccatcgag    480
gctatcgccc tccgctccct cggctcctgg gaagacctgc aagtcaacac cttccaagag    540
atgaagactt acgctctgaa tgtggcattg ctgtccatct tcggcgagga ggagatgcag    600
tacatcgagg agctgaagca gtgctacctg acgctggaga aggggtacaa ctcgatgccg    660
gtgaacctgc cgggcacgct gttccacaag gccatgaagg cccgaaagcg gctgggcgcc    720
attgtggccc acatcatctc ggcccggcgc gagcgcgagc gcgggagcga cctcctgggc    780
tccttcaagg acggccgcga ggcgctcacc gacgaccaga tcgccgacaa cgccatcggc    840
gtcatcttcg ccgcgcgcga caccaccgcc agcgtgctca cgtggatggt caagttcctc    900
ggcgacaacc ccgccgtcct caaagccgtc accgaagagc acgctgagat cgcgagggag    960
aaggcgttgt ccggcgagcc actgtcgtgg gccgacacgc ggcggatgcg gatgacgggc    1020
cgggtgatcc aggagacgat gcgggtggcg tccatcctct ccttcacctt cagggaggcc    1080
gtggaggacg tggagtacca agggtacctg attcccaagg ctggaaagt gcttcccctg    1140 ctccggaaca tccaccacaa ccccgaccac ttcccctccc ctgaaaagtt cgatccttca    1200
cgattcgagg tggcccccaa gcccaacacg ttcatgccgt tcgggaacgg gacccactcg    1260
tgccccggca acgagctggc caagctggag atgctcgtcc tctgccacca cctcgccacc    1320
aagtacagat ggtccacctc caagtccgag agcggcgtcc agttcggccc cttcgccctc    1380
```
cccatcaacg gcctccccat gaccttcacc cgcaaggacg acaagaacaa agcc        1434

<210> SEQ ID NO 10
<211> LENGTH: 478
<212> TYPE: PRT
<213> ORGANISM: Triticum aestivum

<400> SEQUENCE: 10

Met Ala Ala Phe Ile Leu Phe Leu Cys Leu Leu Val Pro Leu Val Leu
1               5                   10                  15

Ala Cys Ala Val Arg Ala Arg Lys Gly Ala Ala Gly Arg Ala Ser Ser
            20                  25                  30

Gly Gly Gly Gly Lys Lys Gly Gly Thr Ser Leu Pro Leu Pro Pro Gly
        35                  40                  45

Ser Met Gly Trp Pro Tyr Val Gly Glu Thr Thr Gln Leu Tyr Ser Ser
    50                  55                  60

Lys Asn Pro Asn Val Phe Phe Ala Arg Lys Arg Asp Lys Tyr Gly Pro
65                  70                  75                  80

Ile Phe Lys Thr His Ile Leu Gly Cys Pro Cys Val Met Val Ser Ser
                85                  90                  95

Pro Glu Ala Ala Lys Phe Val Leu Val Thr Gln Ala His Leu Phe Lys
            100                 105                 110

Pro Thr Phe Pro Ala Ser Lys Glu Arg Met Leu Gly Pro Gln Ala Ile
        115                 120                 125

Phe Phe Gln Gln Gly Asp Tyr His Ala His Leu Arg Arg Leu Val Ser
    130                 135                 140

Arg Ala Phe Ser Pro Glu Ala Ile Arg Gly Ser Val Pro Ala Ile Glu
145                 150                 155                 160

Ala Ile Ala Leu Arg Ser Leu Gly Ser Trp Glu Asp Leu Gln Val Asn
                165                 170                 175

Thr Phe Gln Glu Met Lys Thr Tyr Ala Leu Asn Val Ala Leu Leu Ser
            180                 185                 190

Ile Phe Gly Glu Glu Met Gln Tyr Ile Glu Glu Leu Lys Gln Cys
        195                 200                 205

Tyr Leu Thr Leu Glu Lys Gly Tyr Asn Ser Met Pro Val Asn Leu Pro
210                 215                 220

Gly Thr Leu Phe His Lys Ala Met Lys Ala Lys Arg Leu Gly Ala
225                 230                 235                 240

Ile Val Ala His Ile Ile Ser Ala Arg Arg Glu Arg Glu Arg Gly Ser
                245                 250                 255

Asp Leu Leu Gly Ser Phe Lys Asp Gly Arg Glu Ala Leu Thr Asp Asp
            260                 265                 270

Gln Ile Ala Asp Asn Ala Ile Gly Val Ile Phe Ala Ala Arg Asp Thr
        275                 280                 285

Thr Ala Ser Val Leu Thr Trp Met Val Lys Phe Leu Gly Asp Asn Pro
    290                 295                 300

Ala Val Leu Lys Ala Val Thr Glu Glu His Ala Glu Ile Ala Arg Glu
305                 310                 315                 320

Lys Ala Leu Ser Gly Glu Pro Leu Ser Trp Ala Asp Thr Arg Met
                325                 330                 335

Arg Met Thr Gly Arg Val Ile Gln Glu Thr Met Arg Val Ala Ser Ile
            340                 345                 350

Leu Ser Phe Thr Phe Arg Glu Ala Val Glu Asp Val Glu Tyr Gln Gly
        355                 360                 365

```
Tyr Leu Ile Pro Lys Gly Trp Lys Val Leu Pro Leu Leu Arg Asn Ile
            370                 375                 380

His His Asn Pro Asp His Phe Pro Ser Pro Glu Lys Phe Asp Pro Ser
385                 390                 395                 400

Arg Phe Glu Val Ala Pro Lys Pro Asn Thr Phe Met Pro Phe Gly Asn
                405                 410                 415

Gly Thr His Ser Cys Pro Gly Asn Glu Leu Ala Lys Leu Glu Met Leu
                420                 425                 430

Val Leu Cys His His Leu Ala Thr Lys Tyr Arg Trp Ser Thr Ser Lys
            435                 440                 445

Ser Glu Ser Gly Val Gln Phe Gly Pro Phe Ala Leu Pro Ile Asn Gly
                450                 455                 460

Leu Pro Met Thr Phe Thr Arg Lys Asp Asp Lys Asn Lys Ala
465                 470                 475

<210> SEQ ID NO 11
<211> LENGTH: 1994
<212> TYPE: DNA
<213> ORGANISM: Triticum aestivum

<400> SEQUENCE: 11
cgaagaaagc ctttcgttga catggctgct ttcatcctct tcctctgctt gctcgtgccg      60
ctcgtcctcg cgtgcgccgt ccgcgccagg aagggcgcca ccgggcgggc gtcgtcgggc     120
agcggcggca aaagggcgg caccagcctg ccgctgccgc cggggtcgat gggctggccg      180
tacgtgggcg agaccacgca gctctactcc tccaagaacc caacgtctt cttcgccagg      240
aagcggaaca agtacgggcc catcttcaag acgcacatcc tcgggtgccc ctgcgtcatg     300
gtgtccagcc cggaggccgc caagttcgtg ctcgtcactc aggcgcacct cttcaagcct     360
accttcccgg ccagcaagga gcggatgctg ggcccccagg ccatcttctt ccagcagggg     420
gactaccatg cccacctccg ccgtctcgtc tcacgcgcct ctctcccga ggccatccgc      480
ggttccgtcc ctgccatcga ggctatcgcc ctccgctccc ccggctcctg gaagacctg     540
caagtcaaca ccttccaaga gatgaagact gtgagtgctt cttcctcttc cattcccgct     600
tgctctgctt tcctctgctc tgctctactg ctaaatgatt ggagctcgag gctgatcctt     660
ctcttggtgt cgtggcgcag tacgctctga atgtggcatt gctgtccatc ttcggcgagg     720
aggagatgca gtacatcgag gagctgaagc agtgctacct gacgctggag aagggtaca     780
actcgatgcc ggtgaacctg ccgggcacgc tgttccacaa ggccatgaag gcccgaaagc     840
ggctgggcgc cattgtggcc cacatcatct cggcccggcg cgagcgcgag cgcggagcg     900
acctcctggg ctccttcatg gacgccgcg aggcgctcac cgacgaccag atcgccgaca     960
acgccatcgg cgtcatcttc gccgcgcgcg acaccaccgc cagcgtgctc acgtggatgg    1020
tcaagttcct cggcgacaac cccgccgtcc tcaaagccgt caccgtaagt cgccatcaac    1080
cagctgaccc gcttggtacc cgatcgaaaa gcagtggctg accgtgcgt cgtacgatta    1140
acaggaagag cacgctgaga tcgcgaggga aaggcgttg tccggcgagc cactgtcgtg    1200
ggccgacacg cggcggatgc ggatgacggg ccgggtgatc caggagacga tgcgggtggc    1260
gtccatcctc tccttcacct tcagggaggc cgtggaggac gtggagtacc aaggtgagca    1320
gagcagagac atcaatcgct ttggtcgttt gtggcagcgc agcgctgtac tccgctgtcc    1380
ctctcggagt acagcagtga gctgcctgcc tgcctgcgca tgaactggct cggaaaggac    1440
gcgctcctaa ccgaacgaac gaaatagacc aactcaaact cgcaactcac ctcggcttgc    1500
tctcctctgt gcgtgcaggg tacctgattc ccaagggctg gaaagtgctt cccctgttcc    1560
```

```
ggaacatcca ccacaacccc gaccacttcc cctcccctga aaagttcgat ccttcacgat    1620
tcgaggtcag catcatcaca gccctctgtt tgacgagtct gcttcgattc ggttgatcat    1680
tatctgatta tacgttttgg ttgctgactg caggtggccc ccaagcccaa cacgttcatg    1740
ccgttcggga acgggaccca ctcgtgcccc ggcaacgagc tggccaagct ggagatgctc    1800
gtcctctgcc accacctcgc caccaagtac agatggtcca cctccaagtc cgagagcggc    1860
gtccagttcg gccccttcgc cctccccatc aacggcctcc ccatgacctt cacccgcaag    1920
gacgacaaga acaaagcctg agccatccat ccatccatcc atccatcgcc tcctcctcgt    1980
tcccaaaggg aaat                                                      1994

<210> SEQ ID NO 12
<211> LENGTH: 750
<212> TYPE: DNA
<213> ORGANISM: Triticum aestivum

<400> SEQUENCE: 12
gctcacgtgg atggtcaagt tcctcggcga caaccccgcc gtgctcaaag ccgtcaccgt      60
aagtcgccat caaccagctg acccgcttgg tacccgatcg aaaagcagcg actgacccgt     120
gcatccaaca attaacagga agagcatgcc gagatcgcga gggagaaggc gttgtccggc     180
gagccgctgt cgtgggccga cacgcggcgg atgcggatga cgggccgggt gatccaggag     240
acgatgcggg tggcgtccat cctctccttc accttcaggg aggccgtgga ggacgtggag     300
taccaaggtg agacatcaat caacttcgcg cgcgcgcgcg ctttggtcgt ttgcggcagc     360
gcagcgccgt actgtgctgt ccctctcgga gtacagcagt gcgctgcctg cctgcctgcg     420
catgaactgg ctcggaaagg acgtgctcct aaccgaacgg gaatagacca actcgaactc     480
gcaactcacc tcgactcgct ctcttctgtg cgtgcagggt acctgattcc caagggctgg     540
aaagtgcttc ccctgttccg gaacatccac cacaaccccg accacttccc ctcccccgaa     600
aagttcgatc cttcacgatt cgaggtcagc atcatcacag ccctctgttt gacgagtctg     660
cttcgattcg attgatcatt atctgattat acgttttggt tcgtgactgc aggtggcccc     720
caagcccaac acgttcatgc cgttcgggaa                                      750

<210> SEQ ID NO 13
<211> LENGTH: 750
<212> TYPE: DNA
<213> ORGANISM: Triticum aestivum

<400> SEQUENCE: 13
gctcacgtgg atggtcaagt tcctcggcga caaccccgcc gtgctcaaag ccgtcaccgt      60
aagtcgccat caaccagctg acccgcttgg tacccgatcg aaaagcagcg actgacccgt     120
gcatccaaca attaacagga agagcatgcc gagatcgcga gggagaaggc gttgtccggc     180
gagccgctgt cgtgggccga cacgcggcgg atgcggatga cgggccgggt gatccaggag     240
acgatgcggg tggcgtccat cctctccttc accttcaggg aggccgtgga ggacgtggag     300
taccaaggtg agacatcaat caacttcgcg cgcgcgcgcg ctttggtcgt ttgcggcagc     360
gcagcgccgt actgtgctgt ccctctcgga gtacagcagt gcgctgcctg cctgcctgcg     420
catgaactgg ctcggaaagg acgtgctcct aaccgaacgg gaatagacca actcgaactc     480
gcaactcacc tcgactcgct ctcttctgtg cgtgcagggt acctgattcc caagggccgg     540
aaagtgcttc ccctgttccg gaacatccac cacaaccccg accacttccc ctcccccgaa     600
aagttcgatc cttcacgatt cgaggtcagc atcataacaa ccctctatttt gacgagcctg    660
```

```
<210> SEQ ID NO 14
<211> LENGTH: 745
<212> TYPE: DNA
<213> ORGANISM: Triticum aestivum

<400> SEQUENCE: 14
gctcacgtgg atggtcaagt tcctcggcga caaccccgcc gtgctcaaag ccgtcaccgt      60
aagtcgccat caaccagctg acccgcttgg tacccgatcg aaaagcagcg actgacccgt     120
gcatccaaca attaacagga agagcatgcc gagatcgcga gggagaaggc gttgaccggc     180
gagccgctgt cgtgggccga cacgcggcgg atgcggatga cgggccgggt gatccaggag     240
acgatgcggg tggcgtccat cctctccttc accttcaggg aggccgtgga ggacgtggag     300
taccaaggtg agacatcaat caacttcgcg cgcgcgcttt ggtcgtttgc ggcagcgcag     360
cgccgtactg tgctgtccct ctcggagtac agcagtgcgc tgcctgcctg cctgcgcatg     420
aactggctcg gaaaggacgt gctcctaacc gaacgggaat agaccaactc gaactcgcaa     480
ctcacctcga ctcgctctct tctgtgcgtg cagggtacct gattcccaag ggctggaaag     540
tgcttcccct gttccggaac atccaccaca accccgacca cttcccctcc ccgaaaagt      600 tcgatccttc acgattcgag gtcagcatca taacaaccct ctatttgacg agcctgcttc     660
gattcgattg atcattatct gattatacgt tttggttcgt gactgcaggt gcccccaagc     720
ccaacacgtt catgccgttc gggaa                                           745

<210> SEQ ID NO 15
<211> LENGTH: 745
<212> TYPE: DNA
<213> ORGANISM: Triticum aestivum

<400> SEQUENCE: 15
gctcacgtgg atggtcaagt tcctcggcga caaccccgcc gtcctcaaag ccgtcaccgt      60
aagtcgccat caaccagctg acccgcttgg tacccgatcg aaaagcagtg gctgacccgt     120
gcgtcgtaca attaacagga agagcacgct gagatcgcga gggagaaggc gttgtccggc     180
gagccactgt cgtgggccga cacgcggcgg atgcggatga cgggccgggt gatccaggag     240
acgatgcggg tggcgtccat cctctccttc accttcaggg aggccgtgga ggacgtggag     300
taccaaggtg agcagagcag agacatcaat cgctttggtc gtttgtggca gcgcagtgct     360
gtactccgct gtccctctcg gagtacagca gtgagctgcc tgcctgcctg cgcatgaact     420
ggctcggaaa ggacgcgctc ctaaccgaac gaacgaaata gaccaactca aactcgcaac     480
tcacctcgac ttgctctcct ctgtgcgtgc agggtacctg attcccaagg ctgaaagt      540 gcttcccctg ttccggaaca tccaccacaa ccccgaccac ttcccctccc tgaaaagtt     600 cgatccttca cgattcgagg tcagcatcat cacagccctc tgtttgacga gtctgcttcg     660
attcgattga tcattatctg attatacgtt ttggttgctg actgcaggtg gcccccaagc     720
ccaacacgtt catgccgttc gggaa                                           745

<210> SEQ ID NO 16
<211> LENGTH: 745
<212> TYPE: DNA
<213> ORGANISM: Triticum aestivum

<400> SEQUENCE: 16
```

```
gctcacgtgg atggtcaagt tcctcggcga caaccccgcc gtcctcaaag ccgtcaccgt    60
aagtcgccat caaccagctg acccgcttgg tacccgatcg aaaagcagtg gctgacccgt   120
gcgtcgtaca attaacagga agagcacgct gagatcgcga gggagaaggc gttgtccggc   180
gagccactgt cgtgggccga cacgcggcgg atgcggatga cgggccgggt gatccaggag   240
acgatgcggg tggtgtccat cctctccttc accttcaggg aggccgtgga ggacgtggag   300
taccaaggtg agcagagcag agacatcaat cgctttggtc gtttgtggca gcgcagtgct   360
gtactccgct gtccctctcg gagtacagca gtgagctgcc tgcctgcctg cgcatgaact   420
ggctcggaaa ggacgcgctc ctaaccgaac gaacgaaata gaccaactca aactcgcaac   480
tcacctcgac ttgctctcct ctgtgcgtgc agggtacctg attcccaagg gctggaaagt   540
gcttcccctg ttccggaaca tccaccacaa ccccgaccac ttcccctccc ctgaaaagtt   600
cgatccttca cgattcgagg tcagcatcat cacagccctc tgtttgacga gtctgcttcg   660
attcgattga tcattatctg attatacgtt ttggttgctg actgcaggtg gcccccaagc   720
ccaacacgtt catgccgttc gggaa                                         745
```

<210> SEQ ID NO 17
<211> LENGTH: 745
<212> TYPE: DNA
<213> ORGANISM: Triticum aestivum

<400> SEQUENCE: 17

```
gctcacgtgg atggtcaagt tcctcggcga caaccccgcc gtcctcaaag ccgtcaccgt    60
aagtcgccat caaccagctg acccgcttgg tacccgatcg aaaagcagtg gctgacccgt   120
gcgtcgtaca attaacagga agagcacgct gagatcgcga gggagaaggc gttgtccggc   180
gagccactgt cgtgggccga cacgcggcgg atgcggatga cgggccgggt gatccaggag   240
acgatgcggg tggcgtccat cctctccttc accttcaggg aggccgtgga ggacgtggag   300
taccaaggtg agcagagcag agacatcaat cgctttggtc gtttgtggca gcgcagtgct   360
gtactccgct gtccctctcg gagtacagca gtgagctgcc tgcctgcctg cgcatgaact   420
ggctcggaaa ggacgcgctc ctaaccgaac gaacgaaata gaccaactca aactcgcaac   480
tcacctcgac ttgctctcct ctgtgcgtgc agggtacctg attcccaagg gctggaaagt   540
gcttcccctg tcccggaaca tccaccacaa ccccgaccac ttcccctccc ctgaaaagtt   600
cgatccttca cgattcgagg tcagcatcat cacagccctc tgtttgacga gtctgcttcg   660
gttcgattga tcattatctg attatacgtt ttggttgctg actgcaggtg gcccccaagc   720
ccaacacgtt catgccgttc gggaa                                         745
```

<210> SEQ ID NO 18
<211> LENGTH: 745
<212> TYPE: DNA
<213> ORGANISM: Triticum aestivum

<400> SEQUENCE: 18

```
gctcacgtgg atggtcaagt tcctcggcga caaccccgcc gtcctcaaag ccgtcaccgt    60
aagtcgccat caaccagctg acccgcttgg tacccgatcg aaaagcagtg gctgacccgt   120
gcgtcgtaca attaacagga agagcacgct gagatcgcga gggagaaggc gttgtccggc   180
gagccactgt cgtgggccga cacgcggcgg atgcggatga cgggccgggt gatccaggag   240
acgatgcggg tggcgtccat cctctccttc accttcaggg aggccgtgga ggacgtggag   300
taccaaggtg agcagagcag agacatcaat cgctttggtc gtttgtggca gcgcagtgct   360
```

```
gtactccgct gtccctctcg gagtacagca gtgagctgcc tgcctgcctg cgcatgaact    420
ggctcggaaa ggacgcgctc ctaaccgaac gaacgaaata gaccaactca aactcgcaac    480
tcacctcgac ttgctctcct ctgtgcgtgc agggtacctg attcccaagg ctggaaagt    540 gcttcccctg ttccggaaca tccaccacaa ccccgaccac ttccctccc ctgaaaagtt    600 cgatccttca cgattcgagg tcagcatcat cacagccctc tgtttgacga gtctgcttcg    660
attcgattga tcattatctg attatacgtt ttggttgctg tctgcaggtg gccgccaagc    720
ccaacacgtt catgccgttc gggaa                                          745
```

<210> SEQ ID NO 19
<211> LENGTH: 745
<212> TYPE: DNA
<213> ORGANISM: Triticum aestivum

<400> SEQUENCE: 19

```
gctcacgtgg atggtcaagt tcctcggcga caaccccgcc gtcctcaaag ccgtcaccgt     60
aagtcgccat caaccagctg acccgcttgg tacccgatcg aaaagcagtg gctgacccgt    120
gcgtcgtaca attaacagga agagcacgct gagatcgcga gggagaaggc gttgtccggc    180
gagccgctgt cgtgggccga cacgcggcgg atgcggatga cgggccgggt gatccaggag    240
acgatgcggg tggcgtccat cctctccctt c accttcaggg aggccgtgga ggacgtggag    300
taccaaggtg agcagagcag agacatcaat cgctttggtc gtttgtggca gcgcagtgct    360
gtactccgct gtccctctcg gagtacagca gtgagctgcc tgcctgcctg cgcatgaact    420
ggctcggaaa ggacgcgctc ctaaccgaac gaacgaaata gaccaactca aactcgcaac    480
tcacctcgac ttgctctcct ctgtgcgtgc agggtacctg attcccaagg ctggaaagt    540 gcttcccctg ttccggaaca tccaccacaa ccccgaccac ttccctccc ctgaaaagtt    600 cgatccttca cgattcgagg tcagcatcat cacagccctc tgtttgacga gtctgcttcg    660
attcggttga tcattatctg attatacgtt ttggttgctg actgcaggtg gcccccaagc    720
ccaacacgtt catgccgttc gggaa                                          745
```

<210> SEQ ID NO 20
<211> LENGTH: 744
<212> TYPE: DNA
<213> ORGANISM: Triticum aestivum

<400> SEQUENCE: 20

```
gctcacgtgg atggtcaagt tcctcggcga caaccccgcc gtgctcaaag ccgtcaccgt     60
aagtcgccat caaccagctg acccgcttgg tacccgatcg aaaagcagcg actgacccgt    120
gcatccaaca attagcagga agagcatgcc gagatcgcga gggagaaggc gttgtccggc    180
gagccgctgt cgtgggccga cacgcggcgg atgcggatga cgggccgggt gatccaggag    240
acgatgcggg tggcgtccat cctctccttc accttcaggg aggccgtgga ggacgtggag    300
taccaaggtg agcagagcag agacatcaat cgctttggtc gtttgtggca gcgcagtgct    360
gtactccgct gtccctctcg gagtacagca gtgagctgcc tgcctgcctg cgcatgaact    420
ggctcggaaa ggacgcgctc ctaaccgaac gaacgaaata gaccaactca aactcgcaac    480
tcacctcgac ttgctctcct ctgtgcgtgc agggtacctg attcccaagg ctggaaagt    540 gcttcccctg ttccggaaca tccaccacaa ccccgaccac ttccctccc ctgaaaagtt    600 cgatccttca cgattcgagg tcagcatcat cacagccctc tgtttgacga gtctgcttcg    660
attcgattga tcattatctg attatacgtt ttggttgctg actgcaggtg gcccccaagc    720
```

```
ccaacacgtt catgccgttc ggga                                    744

<210> SEQ ID NO 21
<211> LENGTH: 754
<212> TYPE: DNA
<213> ORGANISM: Triticum aestivum

<400> SEQUENCE: 21
gctcacgtgg atggtcaagt tcctcggcga caaccccgcc gtcctcaaag ccgtcaccgt    60
aagtcgccgt catttcatga acccagctga cccgctaggc acccgatcga aaagcagcga   120
ctgactcgtt catcatacaa tcaacaggaa gggcacgccg agatcgcgag ggagaaggcg   180
ttgtccggcg agccactgtc gtgggccgac acgggcgga tgcggatgac gggccgggtg    240
atccaggaga cgatgcgggt ggcgtccatc ctctccttca ccttcaggga ggccgtggag   300
gacgtggagt accaaggtga gcagagcaga gacatcaatc gctttggtcg tttgtggcag   360
cgcagtgctg tactccgctg tccctctcgg agtacagcag tgagctgcct gcctgcctgc   420
gcatgaactg gctcggaaag gacgcgctcc taaccgaacg aacgaaatag accaactcaa   480
actcgcaact cacctcgact tgctctcctc tgtgcgtgca gggtacctga ttcccaaggg   540
ctggaaagtg cttcccctgt tccggaacat ccaccacaac cccgaccact tcccctcccc   600
tgaaaagttc gatccttcac gattcgaggt cagcatcatc acagccctct gtttgacgag   660
tctgcttcga ttcgattgat cattatctga ttatacgttt tggttgctga ctgcaggtgg   720
cccccaagcc caacacgttc atgccgttcg ggaa                              754

<210> SEQ ID NO 22
<211> LENGTH: 755
<212> TYPE: DNA
<213> ORGANISM: Triticum aestivum

<400> SEQUENCE: 22
gctcacgtgg atggtcaagt tcctcggcga caaccccgcc gtcctcaaag ccgtcaccgt    60
aagtcgccgt catttcatga acccagctga cccgctaggc acccgatcga aaagcagcga   120
ctgactcgtt catcatacaa tcaacaggaa gagcacgccg agatcgcgag ggagaaggcg   180
ttgtccggcg aggcgctgtc gtgggccgac acgggcgga tgcggttgac gggccgggtg    240
atccaggaga cgatgcgggt ggcgtccatc ctctccttca ccttcaggga ggccgtggag   300
gacgtggagt accaaggtga gcagagcaga ggcatcaatc gctttggtcg tttgaggcag   360
cgcagtgctg tgctccgctg tccttctcgg agcacagcag tgcgctgcct gcccgcctgc   420
ctgcctgcgc atgaactggc tcggaaagga cgcgctccta actcaaggga aactcgcaac   480
tcacctcgac ttgctctcct ctgtgcgtgc agggtacctg attcccaagg ctggaaagt    540 gcttcccctg ttccggaaca tccaccacaa ccccgaccac ttcccctccc cgaaaagtt    600 cgacccttca cgattcgagg tcagcatcat cattcacagc cctctgtttg acgagtctct   660
tcttcgattt cgattgatcg ttatctgatt attatacgtc ttggttcgtg actgcaggtg   720
gcccccaagc ccaacacgtt catgccgttc gggaa                             755

<210> SEQ ID NO 23
<211> LENGTH: 20
<212> TYPE: DNA
<213> ORGANISM: Artificial
<220> FEATURE:
<223> OTHER INFORMATION: Oligonucleotide primer

<400> SEQUENCE: 23
```

```
ttggaaagag gagactagag                                              20

<210> SEQ ID NO 24
<211> LENGTH: 20
<212> TYPE: DNA
<213> ORGANISM: Artificial
<220> FEATURE:
<223> OTHER INFORMATION: Oligonucleotide primer

<400> SEQUENCE: 24
cacttggtgt tttctccttg                                              20

<210> SEQ ID NO 25
<211> LENGTH: 20
<212> TYPE: DNA
<213> ORGANISM: Artificial
<220> FEATURE:
<223> OTHER INFORMATION: Oligonucleotide primer

<400> SEQUENCE: 25
aaatggagtg cactcatgtc                                              20

<210> SEQ ID NO 26
<211> LENGTH: 20
<212> TYPE: DNA
<213> ORGANISM: Artificial
<220> FEATURE:
<223> OTHER INFORMATION: Oligonucleotide primer

<400> SEQUENCE: 26
ccttcttcat ctccaatcac                                              20

<210> SEQ ID NO 27
<211> LENGTH: 20
<212> TYPE: DNA
<213> ORGANISM: Artificial
<220> FEATURE:
<223> OTHER INFORMATION: Oligonucleotide primer

<400> SEQUENCE: 27
attcttgtcc aggcaatgag                                              20

<210> SEQ ID NO 28
<211> LENGTH: 20
<212> TYPE: DNA
<213> ORGANISM: Artificial
<220> FEATURE:
<223> OTHER INFORMATION: Oligonucleotide primer

<400> SEQUENCE: 28
ataggcaatc cattctgagg                                              20

<210> SEQ ID NO 29
<211> LENGTH: 20
<212> TYPE: DNA
<213> ORGANISM: Artificial
<220> FEATURE:
<223> OTHER INFORMATION: Oligonucleotide primer

<400> SEQUENCE: 29
gaaaggaata cagtacagtc                                              20

<210> SEQ ID NO 30
<211> LENGTH: 21
<212> TYPE: DNA
<213> ORGANISM: Artificial
```

```
<220> FEATURE:
<223> OTHER INFORMATION: Oligonucleotide primer

<400> SEQUENCE: 30
ggattagatt tggctaacta c                                              21

<210> SEQ ID NO 31
<211> LENGTH: 20
<212> TYPE: DNA
<213> ORGANISM: Artificial
<220> FEATURE:
<223> OTHER INFORMATION: Oligonucleotide primer

<400> SEQUENCE: 31
ggattcgaat gaactcgttg                                                20

<210> SEQ ID NO 32
<211> LENGTH: 21
<212> TYPE: DNA
<213> ORGANISM: Artificial
<220> FEATURE:
<223> OTHER INFORMATION: Oligonucleotide primer

<400> SEQUENCE: 32
ccaagtatct aaccattctt c                                              21

<210> SEQ ID NO 33
<211> LENGTH: 20
<212> TYPE: DNA
<213> ORGANISM: Artificial
<220> FEATURE:
<223> OTHER INFORMATION: Oligonucleotide primer

<400> SEQUENCE: 33
aggtcgtgtg agttcttatg                                                20

<210> SEQ ID NO 34
<211> LENGTH: 20
<212> TYPE: DNA
<213> ORGANISM: Artificial
<220> FEATURE:
<223> OTHER INFORMATION: Oligonucleotide primer

<400> SEQUENCE: 34
cactggtaaa tctcgctctc                                                20

<210> SEQ ID NO 35
<211> LENGTH: 20
<212> TYPE: DNA
<213> ORGANISM: Artificial
<220> FEATURE:
<223> OTHER INFORMATION: Oligonucleotide primer

<400> SEQUENCE: 35
gttacgttgg aactagaagc                                                20

<210> SEQ ID NO 36
<211> LENGTH: 19
<212> TYPE: DNA
<213> ORGANISM: Artificial
<220> FEATURE:
<223> OTHER INFORMATION: Oligonucleotide primer

<400> SEQUENCE: 36
ctaaaatctg gctctgcac                                                 19
```

```
<210> SEQ ID NO 37
<211> LENGTH: 20
<212> TYPE: DNA
<213> ORGANISM: Artificial
<220> FEATURE:
<223> OTHER INFORMATION: Oligonucleotide primer

<400> SEQUENCE: 37
tgagagacga agagaaagac                                                   20

<210> SEQ ID NO 38
<211> LENGTH: 20
<212> TYPE: DNA
<213> ORGANISM: Artificial
<220> FEATURE:
<223> OTHER INFORMATION: Oligonucleotide primer

<400> SEQUENCE: 38
gttccttcaa ctgattctcg                                                   20

<210> SEQ ID NO 39
<211> LENGTH: 20
<212> TYPE: DNA
<213> ORGANISM: Artificial
<220> FEATURE:
<223> OTHER INFORMATION: Oligonucleotide primer

<400> SEQUENCE: 39
taatggtgtt cgttcacgac                                                   20

<210> SEQ ID NO 40
<211> LENGTH: 20
<212> TYPE: DNA
<213> ORGANISM: Artificial
<220> FEATURE:
<223> OTHER INFORMATION: Oligonucleotide primer

<400> SEQUENCE: 40
ctaacacaaa gcttgcttcg                                                   20

<210> SEQ ID NO 41
<211> LENGTH: 23
<212> TYPE: DNA
<213> ORGANISM: Artificial
<220> FEATURE:
<223> OTHER INFORMATION: Oligonucleotide primer

<400> SEQUENCE: 41
tggaccaggt gtactttcaa tgg                                               23

<210> SEQ ID NO 42
<211> LENGTH: 24
<212> TYPE: DNA
<213> ORGANISM: Artificial
<220> FEATURE:
<223> OTHER INFORMATION: Oligonucleotide primer

<400> SEQUENCE: 42
ccactgtctg caattacgac tttg                                              24

<210> SEQ ID NO 43
<211> LENGTH: 19
<212> TYPE: DNA
<213> ORGANISM: Artificial
<220> FEATURE:
<223> OTHER INFORMATION: Oligonucleotide primer

<400> SEQUENCE: 43
```
agcacggacc gtcaaagtc                                                19

<210> SEQ ID NO 44
<211> LENGTH: 19
<212> TYPE: DNA
<213> ORGANISM: Artificial
<220> FEATURE:
<223> OTHER INFORMATION: Oligonucleotide primer

<400> SEQUENCE: 44
tgagaatgcc tacgtagtg                                                19

<210> SEQ ID NO 45
<211> LENGTH: 18
<212> TYPE: DNA
<213> ORGANISM: Artificial
<220> FEATURE:
<223> OTHER INFORMATION: Oligonucleotide primer

<400> SEQUENCE: 45
gagatgctgg tgctcatc                                                 18

<210> SEQ ID NO 46
<211> LENGTH: 20
<212> TYPE: DNA
<213> ORGANISM: Artificial
<220> FEATURE:
<223> OTHER INFORMATION: Oligonucleotide primer

<400> SEQUENCE: 46
acgtcgtcgc tcgatccaac                                               20

<210> SEQ ID NO 47
<211> LENGTH: 18
<212> TYPE: DNA
<213> ORGANISM: Artificial
<220> FEATURE:
<223> OTHER INFORMATION: Oligonucleotide primer

<400> SEQUENCE: 47
ccagcactaa tcgattcc                                                 18

<210> SEQ ID NO 48
<211> LENGTH: 18
<212> TYPE: DNA
<213> ORGANISM: Artificial
<220> FEATURE:
<223> OTHER INFORMATION: Oligonucleotide primer

<400> SEQUENCE: 48
gagagtggtg atgagtaa                                                 18

<210> SEQ ID NO 49
<211> LENGTH: 19
<212> TYPE: DNA
<213> ORGANISM: Artificial
<220> FEATURE:
<223> OTHER INFORMATION: Oligonucleotide primer

<400> SEQUENCE: 49
catggaaaga ggaagttgc                                                19

<210> SEQ ID NO 50
<211> LENGTH: 19
<212> TYPE: DNA
<213> ORGANISM: Artificial

```
<220> FEATURE:
<223> OTHER INFORMATION: Oligonucleotide primer

<400> SEQUENCE: 50
gaagcaagtg tgagctaac                                                19

<210> SEQ ID NO 51
<211> LENGTH: 19
<212> TYPE: DNA
<213> ORGANISM: Artificial
<220> FEATURE:
<223> OTHER INFORMATION: Oligonucleotide primer

<400> SEQUENCE: 51
acagcagtac acggaatac                                                19

<210> SEQ ID NO 52
<211> LENGTH: 18
<212> TYPE: DNA
<213> ORGANISM: Artificial
<220> FEATURE:
<223> OTHER INFORMATION: Oligonucleotide primer

<400> SEQUENCE: 52
gctagctcaa gtatacct                                                 18

<210> SEQ ID NO 53
<211> LENGTH: 20
<212> TYPE: DNA
<213> ORGANISM: Artificial
<220> FEATURE:
<223> OTHER INFORMATION: Oligonucleotide primer

<400> SEQUENCE: 53
caccaaacta gatacagcac                                               20

<210> SEQ ID NO 54
<211> LENGTH: 19
<212> TYPE: DNA
<213> ORGANISM: Artificial
<220> FEATURE:
<223> OTHER INFORMATION: Oligonucleotide primer

<400> SEQUENCE: 54
tggagaagtc ggaaagttg                                                19

<210> SEQ ID NO 55
<211> LENGTH: 20
<212> TYPE: DNA
<213> ORGANISM: Artificial
<220> FEATURE:
<223> OTHER INFORMATION: Oligonucleotide primer

<400> SEQUENCE: 55
tgaagtcaac accttccaag                                               20

<210> SEQ ID NO 56
<211> LENGTH: 21
<212> TYPE: DNA
<213> ORGANISM: Artificial
<220> FEATURE:
<223> OTHER INFORMATION: Oligonucleotide primer

<400> SEQUENCE: 56
gttgtcggcg atctggtcgt c                                             21
```

```
<210> SEQ ID NO 57
<211> LENGTH: 28
<212> TYPE: DNA
<213> ORGANISM: Artificial
<220> FEATURE:
<223> OTHER INFORMATION: Oligonucleotide primer

<400> SEQUENCE: 57
ccaccgcttc tgtcttaact tggcttct                                    28

<210> SEQ ID NO 58
<211> LENGTH: 28
<212> TYPE: DNA
<213> ORGANISM: Artificial
<220> FEATURE:
<223> OTHER INFORMATION: Oligonucleotide primer

<400> SEQUENCE: 58
ctgaaggaag tagtgaggtg gtgaagga                                    28

<210> SEQ ID NO 59
<211> LENGTH: 29
<212> TYPE: DNA
<213> ORGANISM: Artificial
<220> FEATURE:
<223> OTHER INFORMATION: Oligonucleotide primer

<400> SEQUENCE: 59
tggttcacgt agtgggccat cgccctgat                                   29

<210> SEQ ID NO 60
<211> LENGTH: 19
<212> TYPE: DNA
<213> ORGANISM: Artificial
<220> FEATURE:
<223> OTHER INFORMATION: Oligonucleotide primer

<400> SEQUENCE: 60
ccaagtacag atggtctac                                              19

<210> SEQ ID NO 61
<211> LENGTH: 18
<212> TYPE: DNA
<213> ORGANISM: Artificial
<220> FEATURE:
<223> OTHER INFORMATION: Oligonucleotide primer

<400> SEQUENCE: 61
ggagaaaggc tacaactc                                               18

<210> SEQ ID NO 62
<211> LENGTH: 20
<212> TYPE: DNA
<213> ORGANISM: Artificial
<220> FEATURE:
<223> OTHER INFORMATION: Oligonucleotide primer

<400> SEQUENCE: 62
tgatggatgt tcctgaagag                                             20

<210> SEQ ID NO 63
<211> LENGTH: 30
<212> TYPE: DNA
<213> ORGANISM: Artificial
<220> FEATURE:
<223> OTHER INFORMATION: Oligonucleotide primer

<400> SEQUENCE: 63
```

```
ggatccgttg caggttgcag gtaacagaac                                    30
```

<210> SEQ ID NO 64
<211> LENGTH: 27
<212> TYPE: DNA
<213> ORGANISM: Artificial
<220> FEATURE:
<223> OTHER INFORMATION: Oligonucleotide primer

<400> SEQUENCE: 64

```
gaattcggac actgacggat ggagaac                                       27
```

<210> SEQ ID NO 65
<211> LENGTH: 28
<212> TYPE: DNA
<213> ORGANISM: Artificial
<220> FEATURE:
<223> OTHER INFORMATION: Oligonucleotide primer

<400> SEQUENCE: 65

```
aggatccacc tcgctggtct gagtgatc                                      28
```

<210> SEQ ID NO 66
<211> LENGTH: 26
<212> TYPE: DNA
<213> ORGANISM: Artificial
<220> FEATURE:
<223> OTHER INFORMATION: Oligonucleotide primer

<400> SEQUENCE: 66

```
agaattcgtc acactatcac ttcgtc                                        26
```

<210> SEQ ID NO 67
<211> LENGTH: 22
<212> TYPE: DNA
<213> ORGANISM: Artificial
<220> FEATURE:
<223> OTHER INFORMATION: Oligonucleotide primer

<400> SEQUENCE: 67

```
gacgtcatca agaagcctta cc                                            22
```

<210> SEQ ID NO 68
<211> LENGTH: 23
<212> TYPE: DNA
<213> ORGANISM: Artificial
<220> FEATURE:
<223> OTHER INFORMATION: Oligonucleotide primer

<400> SEQUENCE: 68

```
atgtcatcaa gaagccgtac ctc                                           23
```

<210> SEQ ID NO 69
<211> LENGTH: 35
<212> TYPE: DNA
<213> ORGANISM: Artificial
<220> FEATURE:
<223> OTHER INFORMATION: Oligonucleotide primer

<400> SEQUENCE: 69

```
aaggatccga ctaccacacc cacctccgcc gtctc                              35
```

<210> SEQ ID NO 70
<211> LENGTH: 31
<212> TYPE: DNA
<213> ORGANISM: Artificial

```
<220> FEATURE:
<223> OTHER INFORMATION: Oligonucleotide primer

<400> SEQUENCE: 70
aacccgggat ctggtcgtcg gtgagcgcct c                              31

<210> SEQ ID NO 71
<211> LENGTH: 31
<212> TYPE: DNA
<213> ORGANISM: Artificial
<220> FEATURE:
<223> OTHER INFORMATION: Oligonucleotide primer

<400> SEQUENCE: 71
aaactagtat ctggtcgtcg gtgagcgcct c                              31

<210> SEQ ID NO 72
<211> LENGTH: 19
<212> TYPE: DNA
<213> ORGANISM: Artificial
<220> FEATURE:
<223> OTHER INFORMATION: Oligonucleotide primer

<400> SEQUENCE: 72
actcaccgcg acgtctgtc                                            19

<210> SEQ ID NO 73
<211> LENGTH: 18
<212> TYPE: DNA
<213> ORGANISM: Artificial
<220> FEATURE:
<223> OTHER INFORMATION: Oligonucleotide primer

<400> SEQUENCE: 73
gcgcgtctgc tgctccat                                             18

<210> SEQ ID NO 74
<211> LENGTH: 23
<212> TYPE: DNA
<213> ORGANISM: Artificial
<220> FEATURE:
<223> OTHER INFORMATION: Oligonucleotide primer

<400> SEQUENCE: 74
gttgcaggtt gcagtaacag aac                                       23

<210> SEQ ID NO 75
<211> LENGTH: 21
<212> TYPE: DNA
<213> ORGANISM: Artificial
<220> FEATURE:
<223> OTHER INFORMATION: Oligonucleotide primer

<400> SEQUENCE: 75
gtcgcctcta tcgtgcagtt g                                         21

<210> SEQ ID NO 76
<211> LENGTH: 23
<212> TYPE: DNA
<213> ORGANISM: Artificial
<220> FEATURE:
<223> OTHER INFORMATION: Oligonucleotide primer

<400> SEQUENCE: 76
gctcacgtgg atggtcaagt tcc                                       23
```

<210> SEQ ID NO 77
<211> LENGTH: 24
<212> TYPE: DNA
<213> ORGANISM: Artificial
<220> FEATURE:
<223> OTHER INFORMATION: Oligonucleotide primer

<400> SEQUENCE: 77
ttcccgaacg gcatgaacgt gttg                                          24

<210> SEQ ID NO 78
<211> LENGTH: 23
<212> TYPE: DNA
<213> ORGANISM: Artificial
<220> FEATURE:
<223> OTHER INFORMATION: Oligonucleotide primer

<400> SEQUENCE: 78
tgagcagagc agagcatcaa tcg                                           23

<210> SEQ ID NO 79
<211> LENGTH: 24
<212> TYPE: DNA
<213> ORGANISM: Artificial
<220> FEATURE:
<223> OTHER INFORMATION: Oligonucleotide primer

<400> SEQUENCE: 79
gttgcgagtt tcccttgagt tagg                                          24

<210> SEQ ID NO 80
<211> LENGTH: 25
<212> TYPE: DNA
<213> ORGANISM: Artificial
<220> FEATURE:
<223> OTHER INFORMATION: Oligonucleotide primer

<400> SEQUENCE: 80
caaggtgaga catcaatcaa cttcg                                         25

<210> SEQ ID NO 81
<211> LENGTH: 23
<212> TYPE: DNA
<213> ORGANISM: Artificial
<220> FEATURE:
<223> OTHER INFORMATION: Oligonucleotide primer

<400> SEQUENCE: 81
gcgagttcga gttggtctat tcc                                           23

<210> SEQ ID NO 82
<211> LENGTH: 24
<212> TYPE: DNA
<213> ORGANISM: Artificial
<220> FEATURE:
<223> OTHER INFORMATION: Oligonucleotide primer

<400> SEQUENCE: 82
tgagcagagc agagrcatca atcg                                          24

<210> SEQ ID NO 83
<211> LENGTH: 26
<212> TYPE: DNA
<213> ORGANISM: Artificial
<220> FEATURE:
<223> OTHER INFORMATION: Oligonucleotide primer

<400> SEQUENCE: 83
cgagtttgag ttggtctatt tcgttc                                       26

<210> SEQ ID NO 84
<211> LENGTH: 25
<212> TYPE: DNA
<213> ORGANISM: Artificial
<220> FEATURE:
<223> OTHER INFORMATION: Oligonucleotide primer

<400> SEQUENCE: 84
caccgtaagt cgccgtcatt tcatg                                        25

<210> SEQ ID NO 85
<211> LENGTH: 25
<212> TYPE: DNA
<213> ORGANISM: Artificial
<220> FEATURE:
<223> OTHER INFORMATION: Oligonucleotide primer

<400> SEQUENCE: 85
cgatctcggc gtgctcttcc tgttg                                        25

<210> SEQ ID NO 86
<211> LENGTH: 28
<212> TYPE: DNA
<213> ORGANISM: Artificial
<220> FEATURE:
<223> OTHER INFORMATION: Oligonucleotide primer

<400> SEQUENCE: 86
caagttcctc ggcgacaacc ccgccgtg                                     28

<210> SEQ ID NO 87
<211> LENGTH: 26
<212> TYPE: DNA
<213> ORGANISM: Artificial
<220> FEATURE:
<223> OTHER INFORMATION: Oligonucleotide primer

<400> SEQUENCE: 87
cggcatgctc ttcctgttaa ttgttg                                       26

<210> SEQ ID NO 88
<211> LENGTH: 24
<212> TYPE: DNA
<213> ORGANISM: Artificial
<220> FEATURE:
<223> OTHER INFORMATION: Oligonucleotide primer

<400> SEQUENCE: 88
gttgcaggtt gcaggtaaca gaac                                         24

<210> SEQ ID NO 89
<211> LENGTH: 21
<212> TYPE: DNA
<213> ORGANISM: Artificial
<220> FEATURE:
<223> OTHER INFORMATION: Oligonucleotide primer

<400> SEQUENCE: 89
gtcgcctcta tcgtgcagtt g                                            21

<210> SEQ ID NO 90
<211> LENGTH: 1347
<212> TYPE: DNA
<213> ORGANISM: Oryza sativa

<400> SEQUENCE: 90

```
atgggtgctt ttcttctgtt cgtgtgcgtg ctcgcgcctt tcttgcttgt ctgcgccgtc      60
cgcggccgcc gccggcaggc ggctcgtcgg aagcggcggc gtgcggcctg ccgctgccgc     120
cggggtcgat ggggtggccg tacgtcgggg agacgttcca gctgtactcg tccaagaacc     180
ccaacgtgtt cttcaacaag aagcggaaca agtacggtcc catcttcaag acgcacatcc     240
tgggatgccc ctgcgtgatg gtgtccagcc cggaggcggc gcggttcgtg ctggtgacgc     300
aggcgcacct cttcaagccc accttcccgg cgagcaagga gcggatgctg gtcccagg      360
ccatcttctt ccagcagggc gactaccacg cccacctccg ccgcatcgtc tcccgcgcct     420
tctcccccga cagtacgcgc tgaatgtggc attgctgtcc atcttcgggg aggaggagat     480
gcgctacatc gaggagctga agcagtgcta cctgacgctg gagaaggggt acaactcgat     540
gccggtgaac ctgccgggca ccctgttcca aaggccatg aaggcccgga agaggctggg     600
cgccattgtg gcccacatca tctctgcccg gcgcgagcgg cagcggggga cgacctgct      660
agggtcgttc gtggacggcc gcgaggccct caccgacgcc cagatcgccg acaacgtcat     720
cggcgtcatc ttcgccgccc gcgacaccac cgccagcgtc ctcacctgga tggtcaagtt     780
cctcggcgac cacccgccg tcctcaaggc cgtcaccgta agttcgcctc ctcatatgaa      840
gagcagctgc agattgccaa ggagaaagag gcgtcgggcg agccgctgtc atgggcggac     900
acgcggcgga tgaagatgac gagccgggtc atccaggaga cgatgagggt ggcgtccatc     960
ctctccttca ccttcaggga ggccgtggag acgtggaat accaagggta cctgatcccc    1020
aagggctgga agtgctacc tctgttccgc aacatccacc acaaccccga ccacttcccc     1080
tgcccggaaa agttcgaccc gtcccggttc gagctgttgc aggtggcgcc caagcccaac    1140
acgttcatgc cgttcgggaa cgggacccac tcgtgcccgg caacgagct cgccaagctg     1200
gagatgctcg tgctcttcca ccacctcgca accaagtaca ggtggtccac gtccaagtcc    1260
gagagcggcg tccagttcgg ccccttcgcg ctgccgctca acggcctccc catgagcttc    1320
acccgcaaga acaccgagca ggagtga                                         1347
```

<210> SEQ ID NO 91
<211> LENGTH: 1533
<212> TYPE: DNA
<213> ORGANISM: Oryza sativa

<400> SEQUENCE: 91

```
atggctttct tgctcttctt tgtctttgtg acagctgcag tgctgtgctt cgtcgtcccg      60
gcgttcttgc tgctctgcac gagcgtgcag aggaggagag atgttggaca gggtggaggg    120
cgagattggc agaagaagaa gaagctcagg cttcctccgg gatccatggg ctggccgtac    180
gtcggcgaga cgctccagct ctactcccag gaccccaacg tcttcttcgc ctccaagcag    240
aagaggtacg gcgagatatt caagacgaat ctgctggggt gcccgtgcgt gatgctggcg    300
agcccggagg cggcgaggtt cgtgctggtg tcgcaggcga ggctgttcaa gccgacgtac    360
ccgccgagca aggagcggat gatcgggccg tcggcgctct cttccacca gggcgagtac     420
cacctccgcc tccgccgcct cgtccaggcc gccctcgccc cggactccct ccgcgccctc    480
gtcccggacg tcgacgccgc cgtcgccgcc acgctcgccg cctggtccgg cggccacgtc    540
gccagcacct tccacgccat gaagaagctc tcgttcgacg tcggcgtcgt gaccatcttc    600
ggcggccggc tcggccgccg gcacaggcag gagctgagga cgaactactc cgtcgtggag    660
agaggctaca actgcttccc caaccgcttc ccggggacgc tctaccacaa ggcgatccag    720
```

```
gcgaggaagc ggctgcgcgc gatcctgagc gagatcgtgg cggagcggcg ggcgcgcggc      780
ggcggcggcg gcggcggcgg cgacgacctc ctcggcggcc tcatgcggtc gcgcgacgac      840
ggcaccgccg gcgcggtggc gctgctcacc gacgaccaga tcgccgacaa cgtcgtcggc      900
gtgctgttcg cggcgcagga caccaccgcc agcgtcctca cctggatcct caagtacctc      960
cacgactcgc cgaagcttct cgaagccgtc aaggcggagc agatggcgat ctacgtggcc     1020
aacgagggcg ggaagcggcc gctgacgtgg acgcagacga ggagcatgac actcacgcat     1080
caggttatac tggagagctt gaggatggcg agcataatct ccttcacgtt cagagaggca     1140
gtcgccgacg tggagtacaa aggtttcctg attccaaagg ggtggaaggt gatgcctctg     1200
ttcaggaaca tccatcacaa cccggactac ttccaggatc cacaaaagtt tgatccttct     1260
agattcaagg tggcgccgcg tccaagcacg ttcctgccgt tcgggagcgg cgtgcacgcg     1320
tgcccgggca acgagctggc caagctggag atgctcgtcc tcgtccaccg cctcgtcacc     1380
gcctacaggt gggagatcgt cggggcgagc gacgaggtgg agtacagccc gttcccggtg     1440
ccgaggggcg ggctcaacgc caagctgtgg aagcaggagg cggaggagga catgtacatg     1500
gccatgggca ccatcacagc agcaggtgct tga                                  1533

<210> SEQ ID NO 92
<211> LENGTH: 19
<212> TYPE: DNA
<213> ORGANISM: Artificial
<220> FEATURE:
<223> OTHER INFORMATION: Oligonucleotide primer

<400> SEQUENCE: 92
aagggctgga aagtgcttc                                                    19

<210> SEQ ID NO 93
<211> LENGTH: 19
<212> TYPE: DNA
<213> ORGANISM: Artificial
<220> FEATURE:
<223> OTHER INFORMATION: Oligonucleotide primer

<400> SEQUENCE: 93
cttgcgggtg aaggtcatg                                                    19

<210> SEQ ID NO 94
<211> LENGTH: 300
<212> TYPE: DNA
<213> ORGANISM: Artificial
<220> FEATURE:
<223> OTHER INFORMATION: Probe

<400> SEQUENCE: 94
aagggctgga aagtgcttcc cctgttccgg aacatccacc acaacccga ccacttcccc        60 tcccccgaaa agttcgatcc ttcacgattc gaggtggccc ccaagcccaa cacgttcatg      120
ccgttcggga acgggaccca ctcgtgcccc ggcaacgagc tggccaagct ggagatgctc      180
gtcctctgcc accacctcgc caccaagtac agatggtcta cctccaagtc cgagagcggc      240
gtgcagttcg gcccccttcgc cctgcccatc aacggcctcc ccatgacctt cacccgcaag    300
```